United States Patent
Lewis et al.

(10) Patent No.: US 12,319,965 B2
(45) Date of Patent: Jun. 3, 2025

(54) DIAGNOSTIC AND THERAPEUTIC METHODS FOR THE TREATMENT OF RHEUMATOID ARTHRITIS (RA)

(71) Applicants: Genentech, Inc., South San Francisco, CA (US); Queen Mary University of London, London (GB)

(72) Inventors: Myles Lewis, London (GB); Costantino Pitzalis, London (GB); Nandhini Ramamoorthi, South San Francisco, CA (US); Michael John Townsend, San Jose, CA (US); Jason Hackney, San Carlos, CA (US)

(73) Assignees: Genentech, Inc., South San Francisco, CA (US); Queen Mary University of London, London (GB)

( * ) Notice: Subject to any disclaimer, the term of this patent is extended or adjusted under 35 U.S.C. 154(b) by 1177 days.

(21) Appl. No.: 16/937,535

(22) Filed: Jul. 23, 2020

(65) Prior Publication Data
US 2020/0399703 A1    Dec. 24, 2020

Related U.S. Application Data

(63) Continuation of application No. PCT/US2019/014914, filed on Jan. 24, 2019.
(Continued)

(51) Int. Cl.
C12Q 1/68 (2018.01)
A61K 31/519 (2006.01)
(Continued)

(52) U.S. Cl.
CPC .......... *C12Q 1/6883* (2013.01); *A61K 31/519* (2013.01); *A61P 19/02* (2018.01);
(Continued)

(58) Field of Classification Search
None
See application file for complete search history.

(56) References Cited

U.S. PATENT DOCUMENTS

| 6,607,879 B1 * | 8/2003 | Cocks ............... C12Q 1/6883 |
| | | 435/6.12 |
| 2003/0154032 A1 * | 8/2003 | Pittman ............. C07K 14/4713 |
| | | 702/20 |

(Continued)

FOREIGN PATENT DOCUMENTS

| JP | 2013-503643 A | 2/2013 |
| JP | 2014-512806 A | 5/2014 |

(Continued)

OTHER PUBLICATIONS

Notice of Reasons for Rejection for Japanese Patent Application No. 2020-536548, dated Jul. 25, 2023 (12 pages).
(Continued)

*Primary Examiner* — Aaron A Priest
(74) *Attorney, Agent, or Firm* — Clark & Elbing LLP; Thomas J. Takara

(57) ABSTRACT

The present invention provides prognostic, predictive, and therapeutic methods for the treatment of rheumatoid arthritis (RA). The invention is based, at least in part, on the discovery that the expression level of one or more biomarkers described herein in a sample (e.g., a synovial tissue sample, a synovial fluid sample, or a combination thereof) from an individual having RA can be used in methods of determining whether an individual having RA is likely to exhibit disease progression, identifying an individual having RA who is likely to respond to a treatment including a disease modifying anti-rheumatic drug (DMARD), predicting responsiveness of an individual having RA to a treatment including a DMARD, selecting a therapy for an individual
(Continued)

having RA, and treating an individual having RA, as well as related kits.

17 Claims, 12 Drawing Sheets
(11 of 12 Drawing Sheet(s) Filed in Color)

Specification includes a Sequence Listing.

Related U.S. Application Data

(60) Provisional application No. 62/621,156, filed on Jan. 24, 2018.

(51) Int. Cl.
  *A61P 19/02* (2006.01)
  *C07K 16/28* (2006.01)
  *C12Q 1/6883* (2018.01)

(52) U.S. Cl.
  CPC ...... *C07K 16/2866* (2013.01); *C07K 16/2887* (2013.01); *C12Q 2600/106* (2013.01); *C12Q 2600/118* (2013.01); *C12Q 2600/158* (2013.01)

(56) References Cited

U.S. PATENT DOCUMENTS

| | | | | |
|---|---|---|---|---|
| 2007/0048301 | A1* | 3/2007 | Bodary-Winter | A61P 9/00 435/7.1 |
| 2008/0159999 | A1* | 7/2008 | Stefanidis | A61P 17/00 435/405 |
| 2008/0199853 | A1* | 8/2008 | Wohlgemuth | A61P 11/06 435/6.11 |
| 2010/0145901 | A1* | 6/2010 | Han | A61P 29/00 706/52 |
| 2011/0016543 | A1* | 1/2011 | Weinstein | A01K 67/0276 800/15 |
| 2011/0052488 | A1* | 3/2011 | Dennis, Jr. | C12Q 1/6883 424/1.49 |
| 2017/0051351 | A1* | 2/2017 | Hakonarson | A61P 29/00 |

FOREIGN PATENT DOCUMENTS

| | | | |
|---|---|---|---|
| WO | WO-2011/028945 A1 | 3/2011 | |
| WO | WO-2012/061620 A1 | 5/2012 | |
| WO | WO-2012/118750 A2 | 9/2012 | |
| WO | WO-2018020060 A1 * | 2/2018 | ............. C12N 15/63 |

OTHER PUBLICATIONS

Kelly et al., "Ultrasound-guided synovial biopsy: a safe, well-tolerated and reliable technique for obtaining high-quality synovial tissue from both large and small joints in early arthritis patients," Ann Rheum Dis. 74(3):611-7 (2015) (7 pages).
Humby et al., "Use of ultrasound-guided small joint biopsy to evaluate the histopathological response to rheumatoid arthritis therapy," Athritis Rheumatol. 67(10):2601-10 (2015) (10 pages).
Lee et al., "Meta-analysis of gene expression profiles to predict response to biologic agents in rheumatoid arthritis," Clin Rheumatol. 33(6):775-82 (2014).
Sellam et al., "Use of whole-blood transcriptomic profiling to highlight several pathophysiologic pathways associated with response to rituximab in patients with rheumatoid arthritis: data from a randomized, controlled, open-label trial," Arthritis Rheumatol. 66(8):2015-25 (2014).
Sanayama et al., "Prediction of therapeutic responses to tocilizumab in patients with rheumatoid arthritis: biomarkers identified by analysis of gene expression in peripheral blood mononuclear cells using genome-wide DNA microarray," Arthritis Rheumatol. 66(6):1421-31 (2014).
Invitation to Pay Fees for International Patent Application No. PCT/US2019/014914, dated Apr. 10, 2019 (16 pages).
International Search Report and Written Opinion for International Patent Application No. PCT/US2019/014914, dated Jun. 4, 2019 (21 pages).
International Preliminary Report on Patentability for International Patent Application No. PCT/US2019/014914, dated Jul. 28, 2020 (11 pages).
Notice of Reasons for Rejection for Japanese Patent Application No. 2020-536548 issued Dec. 13, 2022. (10 pages).

* cited by examiner

FIG. 1A
| n=144 | |
|---|---|
| Female n (%) | 96 (66.7) |
| Age (yrs) mean (SD) | 51.9 (15.8) |
| Disease duration (months) mean (SD) | 5.6 (3.2) |
| RF+ n (%) | 93 (64.6) |
| Anti-CCP+ n (%) | 97 (67.4) |
| ESR (mm/hr) mean (SD) | 36.3 (28.4) |
| CRP mg/l mean (SD) | 16.8 (27.5) |
| DAS28-ESR mean (SD) | 5.6 (1.5) |
| HAQ mean (SD) | 1.5 (0.7) |
| SJ mean (SD) | 7.4 (5.6) |
| TJ mean (SD) | 11.7 (7.2) |
| VAS mean (SD) | 64.0 (25.0) |
| Total ShSS mean (SD) | 2.5 (6.4) |
| Erosive (≥1) n % (n=120) | 26 (21.7) |
FIG. 1B
FIG. 1C
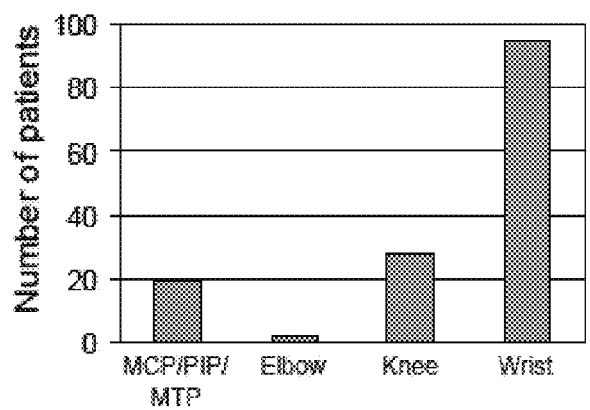

FIG. 2A
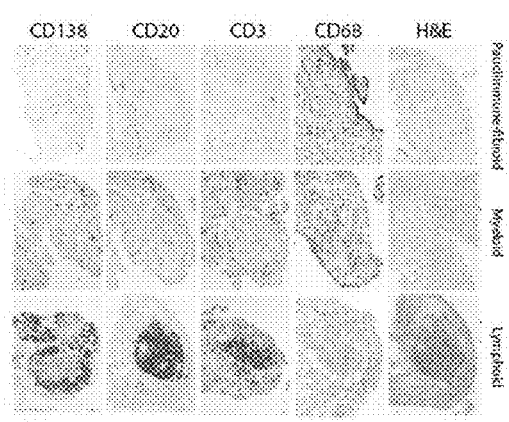
FIG. 2B
FIG. 2C
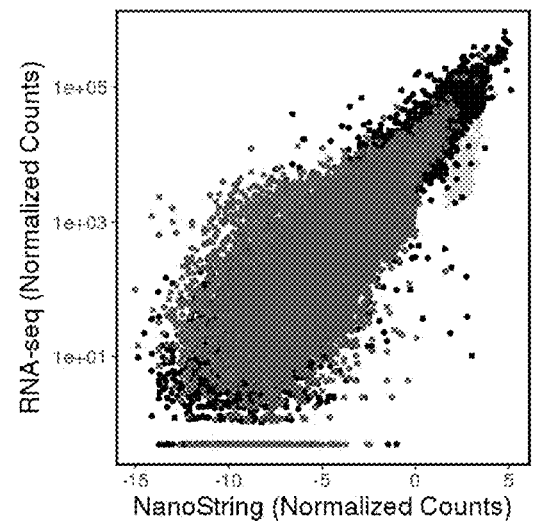
FIG. 2D
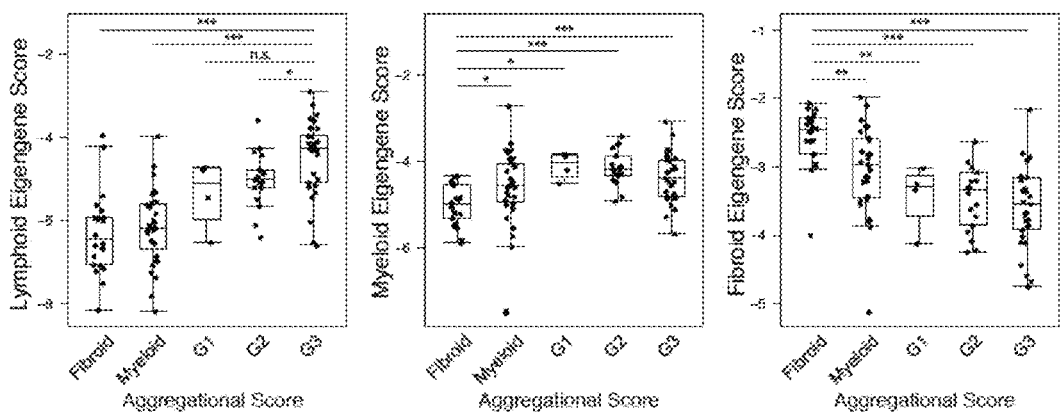

| 12 months (n=89) | | Pauciimune Fibroid/ Myeloid n=55 (61.8%) | Lymphoid n=33 (38.2%) | P value |
|---|---|---|---|---|
| SHSS | Erosions | 0.49 (1.23) | 0.71 (1.7) | 0.759 |
| | JSN | 1.71 (3.88) | 3.62 (4.81) | 0.044 |
| | Total | 2.2 (4.22) | 4.32 (5.98) | 0.068 |
| ΔSHSS | | 0.44 (2.92) | 0.85 (2.22) | 0.042 |
| Progressors/non progressors SHS (≥1) (%) | | 5/50 | 9/25 | 0.029 |

| LASSO without penalising clinical covariates | | LASSO penalising all covariates | |
|---|---|---|---|
| (Intercept) | 3.88 | (Intercept) | 5.14 |
| Disease duration in month | -0.29 | RF | -2.65E-05 |
| RF | -0.027 | SDC1 | 0.59 |
| VAS | -0.071 | CSF2 | 0.19 |
| SJ | -0.41 | DENND1C | 0.049 |
| DAS28-ESR | 1.67 | CD180 | 0.072 |
| Pathotype (Fibroid/Myeloid vs Lymphoid) | -3.3 | UBASH3A | 0.17 |
| US 12 max score ST | -0.15 | CXCL1 | 0.11 |
| US 12 max score PD | 0.27 | MMP10 | 0.011 |
| BLK | 0.012 | | |
| SDC1 | 0.085 | | |
| CSF2 | 0.22 | | |

FIG. 8A
| N=106 | | Paucimmune Fibroid (n=30) (28.3%) | Myeloid (n=33) (31.1%) | Lymphoid (n=43) (40.6%) | P value |
|---|---|---|---|---|---|
| 6 month mean DAS28 (SD) | | -1.6 (1.5) [4] | -2 (3) [11] | -2.4 (1.6) [8] | 0.254 |
| Change in DAS mean (SD) | | 3.2 (2) [4] | 3.7 (1.9) [11] | 3.8 (2) [8] | 0.293 |
| EULAR Responder n(%) | | 25(83.3) | 24(72.7) | 33(76.7) | 0.599 |
| DAS <3.2/>3.2 n(%) | | 19(63.3) | 13(39.4) | 17(39.5) | 0.085 |
| DMARD therapy to 6 months (n=115) n(%) | Non MTX | 6(19.4) | 0(0) | 6(13) | 0.014* |
| | MTX only | 4(12.9) | 2(5.3) | 2(4.3) | |
| | MTX combination | 21(67.7) | 36(94.7) | 38(82.6) | |
*Fisher exact test
FIG. 8B
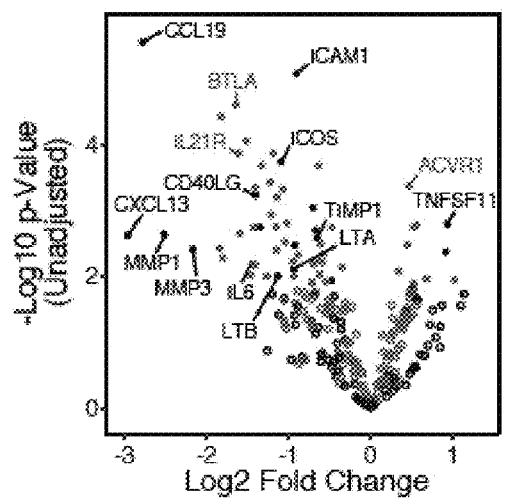
FIG. 8C
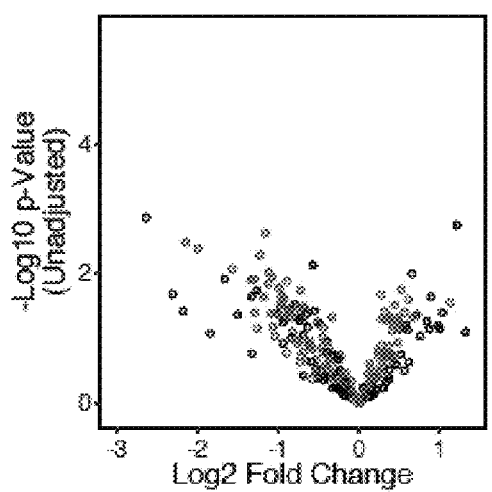

DIAGNOSTIC AND THERAPEUTIC METHODS FOR THE TREATMENT OF RHEUMATOID ARTHRITIS (RA)

SEQUENCE LISTING

The instant application contains a Sequence Listing, which has been submitted electronically in ASCII format and is hereby incorporated by reference in its entirety. Said ASCII copy, created on Jul. 23, 2020, is named 50474-175002_Sequence_Listing_7.23.20_ST25 and is 93,515 bytes in size.

FIELD OF THE INVENTION

The present invention is directed to diagnostic and therapeutic methods for the treatment of rheumatoid arthritis (RA). In particular, the invention provides methods for prognosing disease progression and activity, methods of predicting therapeutic responsiveness, methods of monitoring responsiveness to treatment, methods of selecting a treatment, methods of treatment, and diagnostic kits.

BACKGROUND OF THE INVENTION

Rheumatoid arthritis (RA) is an autoimmune disease of unknown etiology characterized by symmetrical joint involvement, inflammation, synovial lining hyperplasia, and formation of invasive granulation tissue. If uncontrolled, the disease leads to eventual joint destruction accompanied by significant morbidity and increased mortality. The disease is heterogeneous with respect to its clinical and biological presentation, as well as in its response to treatment.

It is generally thought that RA is initiated by a breach of immune tolerance, in particular, to citrullinated self-antigens that can occur years before the onset of clinical symptoms. Multiple cellular players have been identified to contribute to the pathophysiology of RA, including autoreactive T cell and B cell accumulation in the synovium, accompanied by production of autoantibodies directed at a variety of joint antigens, infiltration of inflammatory macrophages into the synovial lining and sublining, and elevated production of cytokines and chemokines that serve to recruit, activate, and sustain synovitis.

Multiple therapeutic approaches have been shown to be highly effective at managing RA symptoms and improving prognosis, including disease modifying anti-rheumatic drugs (DMARDs), such as methotrexate and leflunomide, and biologic therapeutic agents targeting TNFα, IL-6, T cell co-stimulation, B cells, and Janus kinases. However, predicting which individuals would benefit optimally from different therapeutic modalities has been challenging due to heterogeneity of RA.

Thus, there exists an unmet need for improved diagnostic and therapeutic methods for the treatment of individuals having RA.

SUMMARY OF THE INVENTION

The present invention provides diagnostic methods, therapeutic methods, and kits for treating an individual having rheumatoid arthritis (RA).

In a first aspect, the invention features a method of predicting disease progression in an individual having RA, the method comprising determining an expression level of one or more genes set forth in Table 1 in a sample from the individual, wherein a change in the expression level of the one or more genes relative to a reference expression level identifies the individual as one who is more likely to exhibit disease progression. In certain embodiments, the change is an increase, and the one or more genes set forth in Table 1 are selected from one or more genes set forth in Table 2. In certain embodiments, the one or more genes set forth in Table 2 comprise one or more of the following genes: CD180, CSF2, CXCL1, DENND1C, MMP10, SDC1, and UBASH3A. In certain embodiments, the one or more genes set forth in Table 2 comprise two or more of the following genes: CD180, CSF2, CXCL1, DENND1C, MMP10, SDC1, and UBASH3A. In certain embodiments, the one or more genes set forth in Table 2 comprise three or more of the following genes: CD180, CSF2, CXCL1, DENND1C, MMP10, SDC1, and UBASH3A. In certain embodiments, the one or more genes set forth in Table 2 comprise four or more of the following genes: CD180, CSF2, CXCL1, DENND1C, MMP10, SDC1, and UBASH3A. In certain embodiments, the one or more genes set forth in Table 2 comprise five or more of the following genes: CD180, CSF2, CXCL1, DENND1C, MMP10, SDC1, and UBASH3A. In certain embodiments, the one or more genes set forth in Table 2 comprise six or more of the following genes: CD180, CSF2, CXCL1, DENND1C, MMP10, SDC1, and UBASH3A. In certain embodiments, the one or more genes set forth in Table 2 comprise the seven following genes: CD180, CSF2, CXCL1, DENND1C, MMP10, SDC1, and UBASH3A. In certain embodiments, the one or more genes set forth in Table 2 consist of the seven following genes: CD180, CSF2, CXCL1, DENND1C, MMP10, SDC1, and UBASH3A. In certain embodiments, the expression level of the one or more genes set forth in Table 2 is increased in the sample relative to the reference expression level, and the method further comprises administering to the individual a therapeutic agent other than, or in addition to a disease modifying anti-rheumatic drug (DMARD).

In other embodiments, the change is a decrease, and the one or more genes set for in Table 1 are selected from one or more genes set forth in Table 3. In certain embodiments, the expression level of the one or more genes set forth in Table 3 is decreased in the sample relative to the reference expression level, and the method further comprises administering to the individual a therapeutic agent other than, or in addition to, a disease modifying anti-rheumatic drug (DMARD).

In certain embodiments, the disease progression is radiographic progression. In certain embodiments, the radiographic progression is characterized by an increase in ShSS values over a defined time period.

In a second aspect, the invention features a method of treating an individual having RA, the method comprising administering a therapeutic agent other than, or in addition to, a DMARD to the individual, wherein the individual has been identified as one who is more likely to exhibit disease progression by an embodiment of the first aspect.

In a third aspect, the invention features a method of treating an individual having RA, the method comprising: (a) obtaining a sample from the individual; (b) performing a gene expression assay on the sample and detecting (i) an increased expression level of one or more genes set forth in Table 2 in the sample and/or (ii) a decreased level of one or more genes set forth in Table 3 relative to a reference expression level; (c) identifying the individual as having an increased likelihood of benefitting from a therapeutic agent other than, or in addition to, a DMARD; and (d) administering to the individual a therapeutic agent other than, or in addition to, a DMARD.

In a fourth aspect, the invention features a method of treating an individual having RA, the individual being identified as having (i) an increased expression level of one or more genes set forth in Table 2 in a sample from the individual and/or (ii) a decreased expression level of one or more genes set forth in Table 3 in a sample from the individual relative to a reference expression level, the method comprising administering to the individual a therapeutic agent other than, or in addition to, a DMARD.

In a fifth aspect, the invention features a method of treating an individual having RA, the method comprising: (a) determining an expression level of one or more genes set forth in Table 2 or Table 3 in a sample from the individual, wherein (i) the expression level of one or more genes set forth in Table 2 in the sample is determined to be increased and/or (ii) the expression level of the one or more genes set forth in Table 3 is determined to be decreased relative to a reference expression level, and (b) administering to the individual a therapeutic agent other than, or in addition to, a DMARD based on the expression level of the one or more genes set forth in Table 2 or Table 3 determined in step (a).

In certain embodiments of any one of the third, fourth, and fifth aspects, the one or more genes set forth in Table 2 comprise one or more of the following genes: CD180, CSF2, CXCL1, DENND1C, MMP10, SDC1, and UBAS3A.

In certain embodiments of any of the preceding aspects, the expression level of the one or more genes set forth in Table 1 is an average of the expression level of the one or more genes set forth in Table 1. In certain embodiments, the average of the expression level of the one or more genes set forth in Table 1 is an average of a normalized expression level of the one or more genes set forth in Table 1.

In certain embodiments of any of the preceding aspects, the expression level of the one or more genes set forth in Table 1 is a median of the expression level of the one or more genes set forth in Table 1. In certain embodiments, the median of the expression level of the one or more genes set forth in Table 1 is a median of a normalized expression level of the one or more genes set forth in Table 1.

In certain embodiments of any of the preceding aspects, the normalized expression level of the one or more genes set forth in Table 1 is the expression level of the one or more genes set forth in Table 1 normalized to a reference gene. In certain embodiments, the reference gene is ACTB, GAPDH, GUSB, HPRT1, PGK1, RPL19, TUBB, TMEM55B, or a combination thereof.

In certain embodiments of any of the preceding aspects, the reference expression level is a pre-assigned expression level of the one or more genes set forth in Table 1. In certain embodiments, the reference expression level is the expression level of the one or more genes set forth in Table 1 in a reference population of individuals having RA who have not been previously treated with a DMARD, the reference population of individuals consisting of a first subset of individuals who exhibited disease progression and a second subset of individuals who did not exhibit disease progression, wherein the reference expression level significantly separates the first and second subsets of individuals based on a significant difference between the expression level of the one or more genes set forth in Table 1 in the first subset of individuals compared to that of the second subset of individuals. In certain embodiments, the first subset of individuals exhibited disease progression and the second subset of individuals did not exhibit disease progression after about 12 months.

In certain embodiments of the first or fifth aspect, the method further comprises determining one or more clinical covariates of the individual.

In certain embodiments of the second or fifth aspect, one or more clinical covariates has been determined for the individual.

In certain embodiments of any of the preceding aspects, the one or more clinical covariates are one or more of: disease activity score 28-erythrocyte sedimentation rate (DAS28-ESR), disease activity score 28-C reactive protein (DAS28-CRP), rheumatoid factor (RF) titer, disease duration, baseline pathotype, and 12max ultrasound synovial thickening (USST) and ultrasound power Doppler (USPD) scores. In certain embodiments, the clinical covariate is DAS28-ESR. In certain embodiments, the clinical covariate is a RF titer.

In certain embodiments of any of the preceding aspects, the expression level is a nucleic acid expression level. In certain embodiments, the nucleic acid expression level is an mRNA expression level. In certain embodiments, the mRNA expression level is determined by direct digital counting of nucleic acids, RNA-seq, RT-qPCR, qPCR, multiplex qPCR or RT-qPCR, microarray analysis, or a combination thereof. In certain embodiments, the direct digital counting of nucleic acids is by NANOSTRING® NCOUNTER® analysis.

In certain embodiments of any of the preceding aspects, the expression level is a protein expression level. In certain embodiments, the protein expression level is determined by an immunoassay, liquid chromatography-mass spectrometry (LC-MS) technology, nephelometry, aptamer technology, or a combination thereof.

In a sixth aspect, the invention features a method of identifying an individual having RA who may benefit from a treatment comprising a DMARD, the method comprising determining a myeloid eigengene score from a sample from the individual, wherein a myeloid eigengene score from the sample that is at or above a reference myeloid eigengene score identifies the individual as one who may benefit from a treatment comprising a DMARD.

In a seventh aspect, the invention features a method for selecting a therapy for an individual having RA, the method comprising determining a myeloid eigengene score from a sample from the individual, wherein a myeloid eigengene score from the sample that is at or above a reference myeloid eigengene score identifies the individual as one who may benefit from a treatment comprising a DMARD.

In certain embodiments of the sixth or seventh aspect, the method further comprises determining a lymphoid eigengene score from the sample from the individual, wherein a lymphoid eigengene score that is at or above a reference lymphoid eigengene score identifies the individual as one who may benefit from a treatment comprising a DMARD.

In certain embodiments of the sixth or seventh aspect, the myeloid eigengene score from a sample is at or above a reference myeloid eigengene score, and the method further comprises administering to the individual a therapeutically effective amount of a DMARD.

In an eighth aspect, the invention features a method of treating an individual having RA, the method comprising administering a DMARD to the individual, wherein the individual has been identified as one who is more likely to benefit from a treatment comprising a DMARD by an embodiment of the sixth or seventh aspect.

In a ninth aspect, the invention features a method of treating RA in an individual identified as having a myeloid eigengene score from a sample from the individual that is at or above a reference myeloid eigengene score, the method comprising administering to the individual a DMARD. In certain embodiments, prior to the administering, a lymphoid eigengene score from a sample from the individual has been determined to be at or above a reference lymphoid eigengene score.

In a tenth aspect, the invention features a method of treating an individual having RA, the method comprising: (a) obtaining a sample form the individual; (b) performing a gene expression assay on the sample and determining a myeloid eigengene score equal to or increased relative to a reference myeloid eigengene score; (c) identifying the individual as having an increased likelihood of benefitting from a DMARD; and (d) administering to the individual a DMARD. In certain embodiments, prior to the identifying the individual as having an increased likelihood of benefitting from a DMARD, the method further comprises performing a gene expression assay on the sample and determining a lymphoid eigengene score equal to or increased relative to a reference lymphoid eigengene score.

In an eleventh aspect, the invention features a method of treating an individual having RA, the method comprising: (a) determining a myeloid eigengene score from a sample from the individual, wherein the myeloid eigengene score from the sample is determined to be at or above a reference myeloid eigengene score, and (b) administering to the individual a DMARD based on the myeloid eigengene score determined in step (a). In certain embodiments, prior to the administering, the method further comprises determining a lymphoid eigengene score from the sample from the individual, wherein a lymphoid eigengene score in the sample is determined to be at or above a reference lymphoid eigengene score.

In certain embodiments of any of the sixth, seventh, eighth, ninth, tenth, and eleventh aspects, the reference myeloid eigengene score is from a reference population of individuals having RA who have been treated with a DMARD therapy, the population of individuals consisting of a first subset of individuals who responded to the DMARD therapy and a second subset of individuals who did not respond to the DMARD therapy, wherein the reference myeloid eigengene score significantly separates the first and second subsets of individuals, based on a significant difference between the myeloid eigengene score in the first subset of individuals compared to that of the second subset of individuals. In certain embodiments, the first subset of individuals responded to the DMARD therapy and the second subset did not respond to the DMARD therapy after about six months following the initiation of the DMARD therapy.

In certain embodiments of any of the sixth, seventh, eighth, ninth, tenth, and eleventh aspects, the reference lymphoid eigengene score is from a reference population of individuals having RA, the population of individuals consisting of a first subset of individuals who responded to DMARD therapy and a second subset of individuals who did not respond to DMARD therapy, wherein the reference lymphoid eigengene score significantly separates the first and second subsets of individuals, based on a significant difference between the lymphoid eigengene score in the first subset of individuals compared to that of the second subset of individuals.

In certain embodiments of any of the sixth, seventh, eighth, ninth, tenth, and eleventh aspects, the individual has not been previously treated with a DMARD.

In certain embodiments of any of the sixth, seventh, eighth, ninth, tenth, and eleventh aspects, the individual has been previously treated with a DMARD.

In a twelfth aspect, the invention features a method for monitoring the response of an individual having RA to treatment with a DMARD, the method comprising: (a) determining a first myeloid eigengene score from a sample from the individual at a first time point during or after administration of a DMARD, (b) determining a second myeloid eigengene score from a sample from the individual at second time point, and (c) comparing the first myeloid eigengene score with the second myeloid eigengene score, wherein a decrease in the second myeloid eigengene score relative to the first myeloid eigengene score is predictive of an individual who is likely to respond treatment with a DMARD. In certain embodiments, the method further comprises (a) determining a first lymphoid eigengene score from a sample from the individual at a first time point during or after administration of a DMARD, (b) determining a second lymphoid eigengene score from a sample from the individual at second time point, and (c) comparing the first lymphoid eigengene score with the second lymphoid eigengene score, wherein a decrease in the second lymphoid eigengene score relative to the first lymphoid eigengene score is predictive of an individual who is likely to respond treatment with a DMARD. In certain embodiments, the second myeloid eigengene score is decreased relative to the first myeloid eigengene score, and the method further comprises administering an additional dose of a DMARD to the individual. In certain embodiments, the second lymphoid eigengene score is decreased relative to the first lymphoid eigengene score.

In certain embodiments of the twelfth aspect, the individual has been previously treated with a DMARD.

In certain embodiments of the twelfth aspect, the decrease is between about 1.25-fold to about 5-fold. In certain embodiments, the decrease is between about 1.25-fold to about 2-fold. In certain embodiments, the decrease is between about 1.25-fold to about 1.5-fold. In certain embodiments, the decrease is at least about 1.25-fold.

In certain embodiments of any of the preceding aspects, the sample is a synovial sample.

In certain embodiments, the synovial sample is a synovial tissue sample or a synovial fluid sample.

In certain embodiments of any of the preceding aspects, the DMARD is methotrexate, hydroxychloroquine, sulfasalazine, leflunomide, azathioprine, cyclophosphamide, cyclosporine, mycophenolate mofetil, or a combination thereof.

In certain embodiments of any of the first, second, third, fourth, and fifth aspects, the therapeutic agent other than a DMARD is a B cell antagonist, a Janus kinase (JAK) antagonist, a tumor necrosis factor (TNF) antagonist, a decoy TNF receptor, a T cell costimulatory signal antagonist, an IL-1 receptor antagonist, an IL-6 receptor antagonist, or a combination thereof. In certain embodiments, the JAK antagonist is tofacitinib. In certain embodiments, the IL-6 receptor antagonist is tocilizumab. In certain embodiments, the B cell antagonist is rituximab.

BRIEF DESCRIPTION OF THE DRAWINGS

The application file contains at least one drawing executed in color. Copies of this patent or patent application with color drawings will be provided by the Office upon request and payment of the necessary fee.

FIG. 1A is a table showing baseline demographics of the subset of 144 individuals in the PEAC cohort that were enrolled in the study.

FIG. 1B is a representative image of an ultrasound (US)-guided wrist biopsy. The inset grayscale transverse US image of the wrist joint demonstrates the biopsy needle entering the joint space under the extensor tendon complex.

FIG. 1C is a graph indicating the numbers and types of joints sampled.

FIG. 2A is a series of representative images of histological samples acquired from individuals recruited to the Pathobiology of Early Arthritis Cohort (PEAC) showing immune cell infiltration (CD3+, T cells, CD68+ macrophages, CD20+ B cells, and CD138+ plasma cells) and H&E staining per pathotype. All images are at 10× magnification.

FIG. 2B is a table showing mean levels of immune cell infiltration (CD3+, T cells, CD68+ macrophages, CD20+ B cells, and CD138+ plasma cells) per pathotype; asterisk denotes significant differences between groups.

FIG. 2C is a plot of concordance between the NANOSTRING® and RNA-sequencing gene expression in the PEAC cohort data. The overall Spearman rho=0.85 between the two measurements. Individual patients are colored based on gene pathotype assignments (red=lymphoid, purple=myeloid, green=pauciimmune-fibroid, black=additional biology).

FIG. 2D is a series of plots showing lymphoid (left panel), myeloid (center panel), and pauciimmune-fibroid (right panel) eigengene scores against synovial aggregation scores (G1, G2, and G3=grade 1, 2, and 3 aggregates, respectively). Asterisks denote statistical significance as determined by linear regression across groups: *=p<0.05; =p<0.01; *=p<0.001; and n.s.=not significant.

FIG. 8A is a table showing clinical changes in disease activity per pathotype (lymphoid, myeloid, and pauciimmune-fibroid) and treatment regimens according to pathotype.

FIG. 8B is a volcano plot showing changes in gene expression between baseline and six months in individuals with a EULAR response. Individual points are colored by the pathotype in which the gene was originally identified, with RA biology-associated genes colored black.

FIG. 8C is a volcano plot showing changes in gene expression between baseline and six months in individuals with a EULAR non-response. Individual points are colored by the pathotype in which the gene was originally identified, with RA biology-associated genes colored black.

DETAILED DESCRIPTION

I. Definitions

Figure 3A:
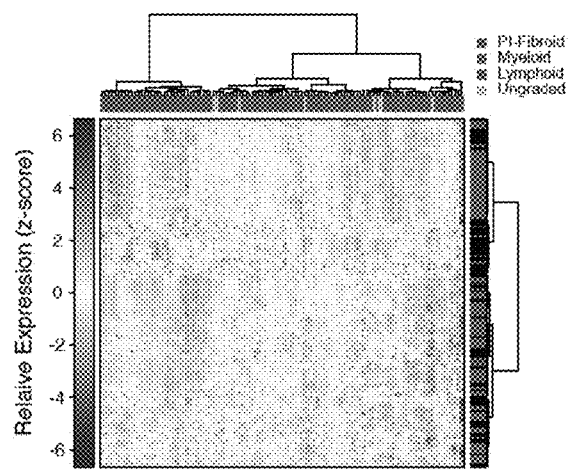
FIG. 3A is a heatmap of NANOSTRING® data. Raw $\log_2$ NANOSTRING® counts for 212 genes and 111 samples from individuals were normalized per probe to give a mean of 0, and standard deviation of 1. Normalized data were clustered by row and column using Euclidean distance and Ward's linkage. Samples are colored according to IHC-determined pathotype, with ungraded samples colored grey. Rows are colored according to the pathotype with which the gene was originally associated, with RA biology-associated genes colored black.

It is to be understood that aspects and embodiments of the invention described herein include "comprising," "consisting," and "consisting essentially of" aspects and embodiments. As used herein, the singular form "a," "an," and "the" includes plural references unless indicated otherwise.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X."

The term "pathotype" as used herein refers to a subtype of RA characterized by certain pathological, histological, and/or clinical features of RA. The pathological, histological, and/or clinical features of RA may be further associated with the expression of one or more particular genes or one or more particular proteins, or a particular pattern of expression of a combination of genes or a combination of proteins. Such pathotypes include, but are not limited to, the lymphoid pathotype (e.g., characterized by B cell-rich aggregates), myeloid pathotype (e.g., characterized by a predominant macrophage infiltrate), and pauciimmune-fibroid pathotype (e.g., characterized by and few infiltrating immune cells, but still expansion of fibroblast lineage cells in the sublining and lining layers). In some embodiments, the pathotype is a lymphoid pathotype and is further characterized by the expression of one or more genes set forth in Table 9. In some embodiments, the pathotype is a myeloid pathotype and is further characterized by the expression of one or more genes set forth in Table 10. In some embodiments, the pathotype is a pauciimmune-fibroid pathotype and is further characterized by the expression of one or more genes set forth in Table 11.

The term "biomarker" as used herein refers to an indicator, e.g., a predictive and/or prognostic indicator, which can be detected in a sample (e.g., a gene) or derived from one or more indicators detected from a sample (e.g., an eigengene score). The biomarker may serve as an indicator of a particular subtype of a disease or disorder (e.g., rheumatoid arthritis) characterized by certain molecular, pathological, histological, and/or clinical features. In some embodiments, a biomarker is a gene. In other embodiments, a biomarker is a collection of genes. Biomarkers include, but are not limited to, polynucleotides (e.g., DNA, and/or RNA), polynucleotide copy number alterations (e.g., DNA copy numbers), polypeptides, polypeptide and polynucleotide modifications (e.g. posttranslational modifications), carbohydrates, and/or glycolipid-based molecular markers.

Such biomarkers include, but are not limited to, CD180, CSF2, CXCL1, DENND1C, MMP10, SDC1, UBASH3A, BLK, BTK, BTLA, CCL19, CD19, CD38, CD40LG, CILP, DENND2D, DKK3, FCRL5, FGF2, FGF9, HLA-DOB, ICOS, JCHAIN, IL36B, IRF4, LOC100505746, LY9, MAP4K1, MMP1, NOG, PIM2, POU2AF1, RHOH, SEL1L3, SIRPG, SLAMF6, SLC31A1, SPIB, TIGIT, TLR10, TMC6, TNF, TNFRSF11B, TNFRSF17, TRAF3PIP3, and XBP1, or a combination thereof. In some embodiments, the biomarker is one or more biomarkers selected from the group consisting of CD180, CSF2, CXCL1, DENND1C, MMP10, SDC1, and UBASH3A. In other embodiments, the biomarker is one or more biomarkers selected from the group consisting of CD180, CSF2, CXCL1, DENND1C, MMP10, SDC1, UBASH3A, BLK, BTK, BTLA, CCL19, CD19, CD38, CD40LG, DENND2D, FCRL5, HLA-DOB, ICOS, JCHAIN, IL36B, IRF4, LOC100505746, LY9, MAP4K1, MMP1, PIM2, POU2AF1, RHOH, SEL1L3, SIRPG, SLAMF6, SLC31A1, SPIB, TIGIT, TLR10, TMC6, TNF, TNFRSF17, TRAF3PIP3, and XBP1. In yet other embodiments, the biomarker is one or more biomarkers selected from the group consisting of CILP, DKK3, FGF2, FGF9, NOG, and TNFRSF11B. Expression of such a biomarker may be determined to be higher or lower in a sample obtained from a patient sensitive or responsive to a treatment (e.g., treatment with a rheumatoid arthritis therapy that includes a DMARD therapy) than a reference level including, e.g., the median expression level of the biomarker in a sample from a group/population of patients, e.g., patients having RA, and being tested for responsiveness to a treatment; the median expression level of the biomarker in a sample from a group/population of patients, e.g., patients having RA, and identified as not responding to a treatment; the level in a sample previously obtained from the individual at a prior time; or the level in a sample from a patient who received prior treatment (e.g., treatment with a DMARD).

The term "CD180" as used herein, refers to any native CD180 antigen from any vertebrate source, including mammals such as primates (e.g., humans) and rodents (e.g., mice and rats), unless otherwise indicated. The term encompasses "full-length," unprocessed CD180 as well as any form of CD180 that results from processing in the cell. The term also encompasses naturally occurring variants of CD180, e.g., splice variants or allelic variants. CD180 is also referred to in the art as lymphocyte antigen 64 (LY64), radioprotective 105 kDa protein (RP105), and Ly78. The nucleic acid sequence of an exemplary human CD180 is shown under NCBI Reference Sequence: NM_005582.2 or in SEQ ID NO: 1. The amino acid sequence of an exemplary protein encoded by human CD180 is shown under UniProt Accession No. Q99467 or in SEQ ID NO: 2.

The term "CSF2" as used herein, refers to any native granulocyte-macrophage colony-stimulating factor from any vertebrate source, including mammals such as primates (e.g., humans) and rodents (e.g., mice and rats), unless otherwise indicated. The term encompasses "full-length," unprocessed CSF2 as well as any form of CSF2 that results from processing in the cell. The term also encompasses naturally occurring variants of CSF2, e.g., splice variants or allelic variants. CSF2 is also referred to in the art as GM-CSF, colony-stimulating factor, CSF, molgramostin, and sargramostim. The nucleic acid sequence of an exemplary human CSF2 is shown under NCBI Reference Sequence: NM_000758.3 or in SEQ ID NO: 3. The amino acid sequence of an exemplary protein encoded by human CSF2 is shown under UniProt Accession No. P04141 or in SEQ ID NO: 4.

The term "CXCL1" as used herein, refers to any native C—X—C motif chemokine 1 from any vertebrate source, including mammals such as primates (e.g., humans) and rodents (e.g., mice and rats), unless otherwise indicated. The term encompasses "full-length," unprocessed CXCL1 as well as any form of CXCL1 that results from processing in the cell. The term also encompasses naturally occurring variants of CXCL1, e.g., splice variants or allelic variants. CXCL1 is also referred to in the art as chemokine ligand 1, growth-regulated alpha protein, GRO-alpha (1-73), melanoma growth stimulatory activity, MGSA, neutrophil-activating protein 3, and NAP-3. The nucleic acid sequence of an exemplary human CXCL1 is shown under NCBI Reference Sequence: NM_001511.3 or in SEQ ID NO: 5. The amino acid sequence of an exemplary protein encoded by human CXCL1 is shown under UniProt Accession No. P09341 or in SEQ ID NO: 6.

The term "DENND1C" as used herein, refers to any native DENN domain-containing protein 1C from any vertebrate source, including mammals such as primates (e.g., humans) and rodents (e.g., mice and rats), unless otherwise indicated. The term encompasses "full-length," unprocessed DENND1C as well as any form of DENND1C that results from processing in the cell. The term also encompasses naturally occurring variants of DENND1C, e.g., splice variants or allelic variants. DENND1C is also referred to in the art as connecdenn 3 and protein FAM31C. The nucleic acid sequence of an exemplary human DENND1C is shown under NCBI Reference Sequence: NM_001290331.1 or in SEQ ID NO: 7. The amino acid sequence of an exemplary protein encoded by human DENND1C is shown under UniProt Accession No. Q8IV53 or in SEQ ID NO: 8.

The term "MMP10" as used herein, refers to any native matrix metallopeptidase 10 from any vertebrate source, including mammals such as primates (e.g., humans) and rodents (e.g., mice and rats), unless otherwise indicated. The term encompasses "full-length," unprocessed MMP10 as well as any form of MMP10 that results from processing in the cell. The term also encompasses naturally occurring variants of MMP10, e.g., splice variants or allelic variants. MMP10 is also referred to in the art as stromelysin-2, SL-2, and transin-2. The nucleic acid sequence of an exemplary human MMP10 is shown under NCBI Reference Sequence: NM_002425.2 or in SEQ ID NO: 9. The amino acid sequence of an exemplary protein encoded by human MMP10 is shown under UniProt Accession No. P09238 or in SEQ ID NO: 10.

The term "SDC1" as used herein, refers to any native syndecan 1 from any vertebrate source, including mammals such as primates (e.g., humans) and rodents (e.g., mice and rats), unless otherwise indicated. The term encompasses "full-length," unprocessed SDC1 as well as any form of SDC1 results from processing in the cell. The term also encompasses naturally occurring variants of SDC1, e.g., splice variants or allelic variants. SDC1 is also referred to in the art as SYND1 and CD138. The nucleic acid sequence of an exemplary human SDC1 is shown under NCBI Reference Sequence: NM_001006946.1 or in SEQ ID NO: 11. The amino acid sequence of an exemplary protein encoded by human SDC1 is shown under UniProt Accession No. P18827 or in SEQ ID NO: 12.

The term "UBASH3A" as used herein, refers to any native ubiquitin associated and SH3 domain containing protein A from any vertebrate source, including mammals such as primates (e.g., humans) and rodents (e.g., mice and rats), unless otherwise indicated. The term encompasses "full-length," unprocessed UBASH3A as any form of UBASH3A from processing in the cell. The term also encompasses naturally occurring variants of UBASH3A, e.g., splice variants or allelic variants. UBASH3A is also referred to in the art as Cbl-interacting protein 4, CLIP4, suppressor of T cell receptor signaling 2, STS-2, T cell ubiquitin ligand 1, and TULA-1. The nucleic acid sequence of an exemplary human UBASH3A is shown under NCBI Reference Sequence: NM_001001895.2 or in SEQ ID NO: 13. The amino acid sequence of an exemplary protein encoded by human UBASH3A is shown under UniProt Accession No. P57075 or in SEQ ID NO: 14.

As used herein, the terms "myeloid eigengene score" and "myeloid eigengene," each of which may be used interchangeably, refer to a numerical value that reflects the degree or amount of pathological, histological, and/or clinical features of an RA of the myeloid pathotype, and which is correlated with the expression level of one or more genes set forth in Table 10 detected in a sample (e.g., a synovial tissue sample, a synovial fluid sample, or a combination thereof) obtained from an individual (e.g., an individual having RA). The myeloid eigengene score may serve as a biomarker (e.g., a predictive and/or prognostic biomaker) of RA of the myeloid pathotype.

As used herein, the terms "lymphoid eigengene score" and "lymphoid eigengene" each of which may be used interchangeably, refer to a numerical value that reflects the degree or amount of pathological, histological, and/or clinical features of an RA of the lymphoid phenotype, and which is correlated with the expression level of one or more genes set forth in Table 9 detected in a sample (e.g., a synovial tissue sample, a synovial fluid sample, or a combination thereof) obtained from an individual (e.g., an individual having RA). The lymphoid eigengene score may serve as a biomarker (e.g., a predictive and/or prognostic biomarker) of RA of the lymphoid phenotype.

As used herein, the terms "pauciimmune-fibroid eigengene score" and "pauciimmune-fibroid eigengene" each of which may be used interchangeably, refer to a numerical value that reflects the degree or amount of pathological, histological, and/or clinical features of an RA of the pauciimmune-fibroid pathotype, and which is correlated with the expression level of one or more genes set forth in Table 11 detected in a sample (e.g., a synovial tissue sample, a synovial fluid sample, or a combination thereof) obtained from an individual (e.g., an individual having RA). The pauciimmune-fibroid eigengene score may serve as a biomarker (e.g., a predictive and/or prognostic biomaker) of RA of the pauciimmune-fibroid pathotype.

The term "detecting" is used herein in the broadest sense to include both qualitative and quantitative measurements of a target molecule. Detecting includes identifying the mere presence of the target molecule in a sample as well as determining whether the target molecule is present in the sample at detectable levels. Detecting may be direct or indirect.

The terms "level of expression" or "expression level" in general are used interchangeably and generally refer to the amount of a biomarker in a biological sample. "Expression" generally refers to the process by which information (e.g., gene-encoded and/or epigenetic information) is converted into the structures present and operating in the cell. Therefore, as used herein, "expression" may refer to transcription into a polynucleotide, translation into a polypeptide, or even polynucleotide and/or polypeptide modifications (e.g., post-translational modification of a polypeptide). Fragments of the transcribed polynucleotide, the translated polypeptide, or polynucleotide and/or polypeptide modifications (e.g., post-translational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs). An expression level for more than one gene of interest may be determined by aggregation methods known to one skilled in the art and also disclosed herein, including, for example, by calculating the median or mean of all the expression levels of the genes of interest. Before aggregation, the expression level of each gene of interest may be normalized by using statistical methods known to one skilled in the art and also disclosed herein, including, for example, normalized to the expression level of one or more housekeeping genes, or normalized to a total library size, or normalized to the median or mean expression level value across all genes measured. In some instances, before aggregation across multiple genes of interest, the normalized expression level of each gene of interest may be standardized by using statistical methods known to one skilled in the art and also disclosed herein, including, for example, by calculating the Z-score of the normalized expression level of each gene of interest.

The term "sample," as used herein, refers to a composition that is obtained or derived from a patient and/or individual of interest that contains a cellular and/or other molecular entity that is to be characterized and/or identified, for example, based on physical, biochemical, chemical, and/or physiological characteristics. Samples include, but are not limited to, synovial tissue samples, synovial fluid samples, tissue samples, primary or cultured cells or cell lines, cell supernatants, cell lysates, platelets, serum, plasma, vitreous fluid, lymph fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, and combinations thereof.

A sample or cell that "expresses" a protein of interest is one in which mRNA encoding the protein, or the protein, including fragments thereof, is determined to be present in the sample or cell.

As used herein, the terms "reference expression level" and "reference level" are used interchangeably to refer to an expression level against which another expression level, e.g., the expression level of one or more genes described herein (e.g., any gene or combination of genes set forth in any one of Tables 1-3) in a sample from an individual is compared, e.g., to make a diagnostic (e.g., predictive and/or prognostic) and/or therapeutic determination. For example, the reference expression level may be derived from expression levels in a reference population (e.g., the median expression level in a reference population, e.g., a population of patients having RA who have not been treated with an RA therapy (e.g., a DMARD (e.g., methotrexate, hydroxychloroquine, sulfasalazine, leflunomide, azathioprine, cyclophosphamide, cyclosporine, or mycophenolate mofetil)), a reference sample, and/or a pre-assigned value (e.g., a cut-off value which was previously determined to significantly (e.g., statistically significantly)) separate a first subset of individuals who exhibited disease progression and a second subset of individuals who did not exhibit disease progression, wherein the reference expression level significantly separates the first and second subsets of individuals based on a significant difference between the expression level in the first subset of individuals compared to that of the second subset of individuals. In some embodiments, the cut-off value may be the median or mean expression level in the reference population. In other embodiments, the reference level may be the top 40%, the top 30%, the top 20%, the top 10%, the top 5%, or the top 1% of the expression level in the reference population. In particular embodiments, the cut-off value may be the median expression level in the reference population. It will be appreciated by one skilled in the art that the numerical value for the reference expression level may vary depending on the indication or disorder (e.g., RA), the methodology used to detect expression levels (e.g., RNA-seq, microarray analysis, or RT-qPCR), and/or the specific combinations of genes examined (e.g., any combination of the genes set forth in Tables 1-3).

As used herein, the terms "reference myeloid eigengene score" and "reference myeloid eigengene" are used interchangeably to refer to a myeloid eigengene score against which another myeloid eigengene score is compared, e.g., to make a diagnostic (e.g., predictive and/or prognostic) and/or therapeutic determination. For example, the reference myeloid eigengene score may be a myeloid eigengene score in a reference sample, a reference population, and/or a pre-determined value. In some instances, the reference myeloid eigengene score is a cut-off value that significantly separates a first subset of individuals who have been treated with an RA therapy (e.g., a DMARD therapy, e.g., therapy including methotrexate) in a reference population and a second subset of individuals who been treated with an RA therapy (e.g., a DMARD therapy, e.g., therapy including methotrexate) in the same reference population based on a significant difference between an individual's responsiveness to treatment with the RA therapy, wherein the cut-off value significantly separates the first subset of individuals who responded to the RA therapy from the second subset of individuals who did not respond to the RA therapy. In some instances, the cut-off value may be the median or mean myeloid eigengene score in the reference population. In other instances, the reference myeloid eigengene score may be the top 40%, the top 30%, the top 20%, the top 10%, the top 5%, or the top 1% of the myeloid eigengene score value in the reference population. It will be appreciated by one skilled in the art that the value for the reference myeloid eigengene score may vary depending on the methodology used to detect expression levels of genes comprising the score (e.g., direct digital counting of nucleic acids (e.g., NANOSTRING® NCOUNTER®), RNA-seq, microarray analysis, or RT-qPCR) and/or the specific combinations of genes examined to derive the reference myeloid eigengene score (e.g., any combination of the genes set forth in Table 10).

As used herein, the terms "reference lymphoid eigengene score" and "reference lymphoid eigengene" are used interchangeably to refer to a lymphoid eigengene score against which another lymphoid eigengene score is compared, e.g., to make a diagnostic (e.g., predictive and/or prognostic) and/or therapeutic determination. For example, the reference lymphoid eigengene score may be a lymphoid eigengene score in a reference sample, a reference population, and/or a pre-determined value. In some instances, the reference lymphoid eigengene score is a cut-off value that significantly separates a first subset of individuals who have been treated with an RA therapy (e.g., a DMARD therapy, e.g., therapy including methotrexate) in a reference population and a second subset of individuals who been treated with an RA therapy (e.g., a DMARD therapy, e.g., therapy including methotrexate) in the same reference population based on a significant difference between an individual's responsiveness to treatment with the RA therapy, wherein the cut-off value significantly separates the first subset of individuals who responded to the RA therapy from the second subset of individuals who did not respond to the RA therapy. In some instances, the cut-off value may be the median or mean lymphoid eigengene score in the reference population. In other instances, the reference lymphoid eigengene score may be the top 40%, the top 30%, the top 20%, the top 10%, the top 5%, or the top 1% of the lymphoid eigengene score value in the reference population. It will be appreciated by one skilled in the art that the value for the reference lymphoid eigengene score may vary depending on the methodology used to detect expression levels of genes comprising the score (e.g., direct digital counting of nucleic acids (e.g., NANOSTRING® NCOUNTER®), RNA-seq, microarray analysis, or RT-qPCR), and/or the specific combinations of genes examined to derive the reference lymphoid eigengene score (e.g., any combination of the genes set forth in Table 9).

Expression "above" a level (e.g., above a reference level), "increased," "increased expression," "increased expression level," "increased levels," "elevated," "elevated expression," "elevated expression levels," or "elevated levels" refers to an increased expression, increased levels of a biomarker or an increased eigengene score in an individual relative to the expression level of the biomarker or eigengene score in a control (e.g., an individual or individuals who are not suffering from the disease or disorder (e.g., RA), an internal control (e.g., a housekeeping biomarker), the level of a biomarker or eigengene score in a sample obtained from the individual prior to administration of a therapy (e.g., a DMARD)), or relative to a reference level (e.g., the median expression level of the biomarker or eigengene score in samples from a group/population of patients, e.g., patients having RA who are being tested for responsiveness to an RA therapy that includes a DMARD; the median expression level of the biomarker or eigengene score in samples from a group/population of patients, e.g., patients having RA who have been identified as not responding to a DMARD; or the level in a sample previously obtained from the individual at a prior time).

Expression "below" a level (e.g., below a reference level), "decreased," "decreased expression," "decreased expression level," "decreased levels," "reduced," "reduced expression," "reduced expression levels," or "reduced levels" refers to decreased expression, decreased levels, of a biomarker or a decreased eigengene score in an individual relative to the expression level of the biomarker or eigengene score in a control (e.g., an individual or individuals who are not suffering from the disease or disorder (e.g., RA), an internal control (e.g., a housekeeping biomarker), or the level of a biomarker or eigengene score in a sample obtained prior to administration of a therapy (e.g., a DMARD), or relative to a reference level (e.g., the median expression level of the biomarker or eigengene score in samples from a group/population of patients, e.g., patients having RA who are being tested for responsiveness to an RA therapy that includes a DMARD (e.g., methotrexate, hydroxychloroquine, sulfasalazine, leflunomide, azathioprine, cyclophosphamide, cyclosporine, or mycophenolate mofetil); the median expression level of the biomarker or eigengene score in samples from a group/population of patients, e.g., patients having RA who have been identified as not responding to an RA therapy that includes a DMARD; or the level in a sample previously obtained from the individual at a prior time). In some embodiments, reduced expression is little or no expression.

A "reference sample," "reference cell," "reference tissue," "control sample," "control cell," or "control tissue," as used herein, refers to a sample, cell, tissue, or standard that is used for comparison purposes. In one embodiment, a reference sample, reference cell, reference tissue, control sample, control cell, or control tissue is obtained from a healthy and/or non-diseased part of the body (e.g., tissue or cells) of the same patient or individual. For example, a reference sample, reference cell, reference tissue, control sample, control cell, or control tissue may be healthy and/or non-diseased cells or tissue adjacent to the diseased cells or tissue (e.g., cells or tissue adjacent to an affected joint). In another embodiment, a reference sample is obtained from an untreated tissue and/or cell of the body of the same patient or individual. In yet another embodiment, a reference sample, reference cell, reference tissue, control sample, control cell, or control tissue is obtained from a healthy and/or non-diseased part of the body (e.g., tissues or cells) of an individual who is not the patient or individual. In even another embodiment, a reference sample, reference cell, reference tissue, control sample, control cell, or control tissue is obtained from an untreated tissue and/or cell of the body of an individual who is not the patient or individual. In another embodiment, a reference sample, reference cell, reference tissue, control sample, control cell, or control tissue is obtained from a patient prior to administration of a therapy (e.g., an RA therapy that includes a DMARD (e.g., methotrexate, hydroxychloroquine, sulfasalazine, leflunomide, azathioprine, cyclophosphamide, cyclosporine, or mycophenolate mofetil) and/or a biologic therapeutic agent (e.g., a B cell antagonist (e.g., rituximab), a Janus kinase (JAK) antagonist (e.g., tofacitinib), a tumor necrosis factor (TNF) antagonist, a decoy TNF receptor, a T cell costimulatory signal antagonist, an IL-1 receptor antagonist, or an IL-6 receptor antagonist (tocilizumab)).

The term "housekeeping biomarker" refers to a biomarker or group of biomarkers (e.g., polynucleotides and/or polypeptides) which are typically similarly present in all cell types. In some embodiments, the housekeeping biomarker is a "housekeeping gene." A "housekeeping gene" refers herein to a gene or group of genes which encode proteins whose activities are essential for the maintenance of cell function and which are typically similarly present in all cell types. Exemplary housekeeping genes may include, but are not limited to, ACTB, GAPDH, GUSB, HPRT1, PGK1, RPL19, TUBB, and TMEM55B.

The term "ACTB" as used herein, refers to any native beta-actin from any vertebrate source, including mammals such as primates (e.g., humans) and rodents (e.g., mice and rats), unless otherwise indicated. The term encompasses "full-length," unprocessed ACTB as well as any form of ACTB that results from processing in the cell. The term also encompasses naturally occurring variants of ACTB, e.g., splice variants of ACTB, e.g., splice variants or allelic variants. ACTB is also referred to in the art as beta (R)-actin, actin beta, PS1TP5-binding protein 1, beta cytoskeletal actin, PS1TP5BP1, BRWS1, and actin, cytoplasmic 1. The nucleic acid sequence of an exemplary human ACTB is shown under NCBI Reference Sequence: NM_002046.6 or in SEQ ID NO: 15. The amino acid sequence of the exemplary protein encoded by human ACTB is shown under UniProt Accession No. P60709-1 or in SEQ ID NO: 16.

The term "GAPDH" as used herein, refers to any native glyceraldehyde-3-phosphate dehydrogenase from any vertebrate source, including mammals such as primates (e.g., humans) and rodents (e.g., mice and rats), unless otherwise indicated. The term encompasses "full-length," unprocessed GAPDH as well as any form of GAPDH that results from processing in the cell. The term also encompasses naturally occurring variants of GAPDH, e.g., splice variants of GAPDH, e.g., splice variants or allelic variants. GAPDH is also referred to in the art as GAPD, EC 1.2.1.12, Epididymis Secretory Sperm Binding Protein Li 162eP, Aging-Associated Gene 9 Protein, HEL-S-162eP, HEL-S-162eP, EC 1.2.1, G3PD, G3PDH, and peptidyl-cysteine S-nitrosylase GAPDH. The nucleic acid sequence of an exemplary human GAPDH is shown under NCBI Reference Sequence: NM_002046.6 or in SEQ ID NO: 17. The amino acid sequence of the exemplary protein encoded by human GAPDH is shown under UniProt Accession No. P04406 or in SEQ ID NO: 18.

The term "GUSB" as used herein, refers to any native glucuronidase beta from any vertebrate source, including mammals such as primates (e.g., humans) and rodents (e.g., mice and rats), unless otherwise indicated. The term encompasses "full-length," unprocessed GUSB as well as any form of GUSB that results from processing in the cell. The term also encompasses naturally occurring variants of GUSB, e.g., splice variants of GUSB, e.g., splice variants or allelic variants. GUSB is also referred to in the art as EC 3.2.1.31, beta-G1, beta-D-glucuronidase, beta-glucuronidase, MPS7, BG, and glucuronidase, beta. The nucleic acid sequence of an exemplary human GUSB is shown under NCBI Reference Sequence: NM_000181.3 or in SEQ ID NO: 19. The amino acid sequence of the exemplary protein encoded by human GUSB is shown under UniProt Accession No. P08236 or in SEQ ID NO: 20.

The term "HPRT1" as used herein, refers to any native hypoxanthine phosphoribosyltransferase 1 from any vertebrate source, including mammals such as primates (e.g., humans) and rodents (e.g., mice and rats), unless otherwise indicated. The term encompasses "full-length," unprocessed HPRT1 as well as any form of HPRT1 that results from processing in the cell. The term also encompasses naturally occurring variants of HPRT1, e.g., splice variants of HPRT1, e.g., splice variants or allelic variants. HPRT1 is also referred to in the art as EC 2.4.2.8, HGPRTase, HGPRT, HPRT, hypoxanthine-guanine phosphoribosyltransferase 1, hypoxanthine-guanine phosphoribosyltransferase, and testicular tissue Protein Li 89. The nucleic acid sequence of an exemplary human HPRT1 is shown under NCBI Reference Sequence: NM_000194.2 or in SEQ ID NO: 21. The amino acid sequence of the exemplary protein encoded by human HPRT1 is shown under UniProt Accession No. P00492 or in SEQ ID NO: 22.

The term "PGK1" as used herein, refers to any native phosphoglycerate kinase 1 from any vertebrate source, including mammals such as primates (e.g., humans) and rodents (e.g., mice and rats), unless otherwise indicated. The term encompasses "full-length," unprocessed PGK1 as well as any form of PGK1 that results from processing in the cell. The term also encompasses naturally occurring variants of PGK1, e.g., splice variants of PGK1, e.g., splice variants or allelic variants. PGK1 is also referred to in the art as cell migration-inducing gene 10 protein, primer recognition protein 2, EC 2.7.2.3, PRP 2, PGKA, epididymis secretory sperm binding protein Li 68p, HEL-S-68p, and MIG10. The nucleic acid sequence of an exemplary human PGK1 is shown under NCBI Reference Sequence: NM_000291.3 or in SEQ ID NO: 23. The amino acid sequence of the exemplary protein encoded by human PGK1 is shown under UniProt Accession No. P00558 or in SEQ ID NO: 24.

The term "RPL19" as used herein, refers to any native ribosomal protein L19 from any vertebrate source, including mammals such as primates (e.g., humans) and rodents (e.g., mice and rats), unless otherwise indicated. The term encompasses "full-length," unprocessed RPL19 as well as any form of RPL19 that results from processing in the cell. The term also encompasses naturally occurring variants of RPL19, e.g., splice variants of RPL19, e.g., splice variants or allelic variants. RPL19 is also referred to in the art as large ribosomal subunit protein EL19, large ribosomal subunit protein EL19, ribosomal protein L19, cytosolic, N-terminus truncated, and L19. The nucleic acid sequence of an exemplary human RPL19 is shown under NCBI Reference Sequence: NM_000981.3 or in SEQ ID NO: 25. The amino acid sequence of the exemplary protein encoded by human RPL19 is shown under UniProt Accession No. P84098 or in SEQ ID NO: 26.

The term "TUBB" as used herein, refers to any native tubulin beta class I from any vertebrate source, including mammals such as primates (e.g., humans) and rodents (e.g., mice and rats), unless otherwise indicated. The term encompasses "full-length," unprocessed TUBB as well as any form of TUBB that results from processing in the cell. The term also encompasses naturally occurring variants of TUBB, e.g., splice variants of TUBB, e.g., splice variants or allelic variants. TUBB is also referred to in the art as tubulin, beta polypeptide, tubulin beta-5 chain, TUBB5, class I beta-tubulin, tubulin beta-1 chain, tubulin beta chain, beta Ib tubulin, beta1-tubulin, tubulin, beta, OK/SW-CI.56, CDCBM6, CSCSC1, TUBB1, and M40. The nucleic acid sequence of an exemplary human TUBB is shown under NCBI Reference Sequence: NM_001293212.1 or in SEQ ID NO: 27. The amino acid sequence of the exemplary protein encoded by human TUBB is shown under UniProt Accession No. P07437 or in SEQ ID NO: 28.

The term "TMEM55B" as used herein, refers to any native transmembrane protein 55B from any vertebrate source, including mammals such as primates (e.g., humans) and rodents (e.g., mice and rats), unless otherwise indicated. The term encompasses "full-length," unprocessed TMEM55B as well as any form of TMEM55B that results from processing in the cell. The term also encompasses naturally occurring variants of TMEM55B, e.g., splice variants of TMEM55B, e.g., splice variants or allelic variants. TMEM55B is also referred to in the art as phosphatidylinositol-4,5-bisphosphate 4-phosphatase 1, PIP4P1, type I phosphatidylinositol-4,5-bisphosphate 4-phosphatase, type I PtdIns-4,5-P(2) 4-phosphatase, type 1 PtdIns-4,5-P2 4-Ptase, PtdIns-4,5-P2 4-Ptase I, EC 3.1.3.78, C14orf9, type 1 phosphatidylinositol 4,5-bisphosphate 4-phosphatase, PtdIns-4,5-P(2) 4-phosphatase type I, and chromosome 14 open reading frame 9. The nucleic acid sequence of an exemplary human TMEM55B is shown under NCBI Reference Sequence: NM_001100814.2 or in SEQ ID NO: 29. The amino acid sequence of the exemplary protein encoded by human TMEM55B is shown under UniProt Accession No. Q86T03 or in SEQ ID NO: 30.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of polypeptide analysis or protocol, one may use the results of the polypeptide expression analysis or protocol to determine whether a specific therapeutic regimen should be performed. With respect to the embodiment of polynucleotide analysis or protocol, one may use the results of the polynucleotide expression analysis or protocol to determine whether a specific therapeutic regimen should be performed.

"Amplification," as used herein, generally refers to the process of producing multiple copies of a desired sequence. "Multiple copies" mean at least two copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The technique of "polymerase chain reaction" or "PCR" as used herein, generally refers to a procedure wherein minute amounts of a specific piece of nucleic acid, RNA and/or DNA, are amplified as described, for example, in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage, or plasmid sequences, etc. See generally Mullis et al., *Cold Spring Harbor Symp. Quant. Biol.* 51:263 (1987) and Erlich, ed., *PCR Technology*, (Stockton Press, N Y, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

The term "multiplex-PCR" refers to a single PCR reaction carried out on nucleic acid obtained from a single source (e.g., an individual) using more than one primer set for the purpose of amplifying two or more DNA sequences in a single reaction.

"Quantitative real-time polymerase chain reaction" or "qRT-PCR" refers to a form of PCR wherein the amount of PCR product is measured at each step in a PCR reaction. This technique has been described in various publications including, for example, Cronin et al., *Am. J. Pathol.* 164(1): 35-42 (2004) and Ma et al., *Cancer Cell* 5:607-616 (2004).

The term "microarray" refers to an ordered arrangement of hybridizable array elements, preferably polynucleotide probes, on a substrate.

The term "RNAseq," also called "RNA-seq" or "Whole Transcriptome Shotgun Sequencing (WTSS)," refers to the use of high-throughput sequencing technologies to sequence and/or quantify cDNA to obtain information about a sample's RNA content. Publications describing RNAseq include: Wang et al. *Nature Reviews Genetics* 10(1):57-63, 2009; Ryan et al. *Bio Techniques* 45(1):81-94, 2008; and Maher et al. *Nature* 458(7234):97-101, 2009.

"Polynucleotide" or "nucleic acid," as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The terms "polynucleotide" and "nucleic acid" specifically includes mRNA and cDNAs.

A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally-occurring nucleotides with an analog, internucleotide modifications such as, for example, those with uncharged linkages (e.g., methyl phosphonates, phosphotriesters, phosphoamidates, carbamates, and the like) and with charged linkages (e.g., phosphorothioates, phosphorodithioates, and the like), those containing pendant moieties, such as, for example, proteins (e.g., nucleases, toxins, antibodies, signal peptides, poly-L-lysine, and the like), those with intercalators (e.g., acridine, psoralen, and the like), those containing chelators (e.g., metals, radioactive metals, boron, oxidative metals, and the like), those containing alkylators, those with modified linkages (e.g., alpha anomeric nucleic acids), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro-, or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, single-stranded polynucleotides that are, but not necessarily, less than about 250 nucleotides in length. Oligonucleotides may be synthetic. The terms "oligonucleotide" and "polynucleotide" are not mutually exclusive. The description above for polynucleotides is equally and fully applicable to oligonucleotides.

The term "primer" or "probe" as used interchangeably herein, refers to a single-stranded polynucleotide that is capable of hybridizing to a nucleic acid and allowing polymerization of a complementary nucleic acid, generally by providing a free 3'-OH group.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells.

The term "diagnosis" is used herein to refer to the identification or classification of a molecular or pathological state, disease or condition (e.g., RA). For example, "diagnosis" may refer to the classification of a particular pathotype of RA, for instance, by histopathological criteria, or by molecular features (e.g., a subtype characterized by expression of one or a combination of biomarkers (e.g., particular genes or proteins encoded by said genes)).

As used herein, the terms "individual," "patient," and "subject" are used interchangeably and refer to any single animal, more preferably a mammal (including such non-human animals as, for example, cats, dogs, horses, rabbits, zoo animals, cows, pigs, sheep, and non-human primates) for which treatment is desired. In particular embodiments, the patient herein is a human. The patient may be an "RA patient," i.e., one who is suffering from RA, or at risk for suffering from RA, or suffering from one or more symptoms of RA.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, treatment is with an RA therapy that includes a DMARD (e.g., methotrexate, hydroxychloroquine, sulfasalazine, leflunomide, azathioprine, cyclophosphamide, cyclosporine, or mycophenolate mofetil) and/or a biologic therapeutic agent (e.g., a B cell antagonist (e.g., rituximab), a Janus kinase (JAK) antagonist (e.g., tofacitinib), tumor necrosis factor (TNF) antagonist, a decoy TNF receptor, a T cell costimulatory signal antagonist, an IL-1 receptor antagonist, or an IL-6 receptor antagonist (e.g., tocilizumab)) are used to delay development of a disease or to slow the progression of a disease or disorder (e.g., RA).

As used herein, "administering" is meant a method of giving a dosage of a compound (e.g., a DMARD (e.g., methotrexate, hydroxychloroquine, sulfasalazine, leflunomide, azathioprine, cyclophosphamide, cyclosporine, or mycophenolate mofetil) and/or a biologic therapeutic agent (e.g., a B cell antagonist (e.g., rituximab), a Janus kinase (JAK) antagonist (e.g., tofacitinib), tumor necrosis factor (TNF) antagonist, a decoy TNF receptor, a T cell costimulatory signal antagonist, an IL-1 receptor antagonist, or an IL-6 receptor antagonist (e.g., tocilizumab)) to an individual. The compositions utilized in the methods described herein can be administered, for example, orally, subcutaneously, intramuscularly, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subconjunctivally, intravesicularly, mucosally, intrapericardially, intraumbilically, intraocularly, intraorbitally, intravitreally (e.g., by intravitreal injection), by eye drop, topically, transdermally, parenterally, by inhalation, by injection, by implantation, by infusion, by continuous infusion, by localized perfusion bathing target cells directly, by catheter, by lavage, in creams, or in lipid compositions. In some instances, the compositions utilized in the methods described herein can be administered orally. In some instances, the compositions utilized in the methods described herein can be administered subcutaneously. The compositions utilized in the methods described herein can also be administered systemically or locally. The method of administration can vary depending on various factors (e.g., the compound or composition being administered and the severity of the condition, disease, or disorder (e.g., RA) being treated).

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

By "reduce or inhibit" is meant the ability to cause an overall decrease of 20%, 30%, 40%, 50%, 60%, 70%, 75%, 80%, 85%, 90%, 95%, or greater. Reduce or inhibit can refer, for example, to the symptoms of the disorder (e.g., RA) being treated.

A "therapeutically effective amount" or "effective amount" refers to an amount of a therapeutic agent to treat or prevent a disease or disorder (e.g., RA) in a mammal. In the case of RA, the therapeutically effective amount of the therapeutic agent may reduce the potential for rheumatoid arthritis, reduce the occurrence of the rheumatoid arthritis, and/or a reduce the severity of rheumatoid arthritis, preferably, to an extent that the individual no longer suffers discomfort and/or altered function due to it. For example, a therapeutically effective amount can refer to the amount necessary of a therapy, when administered to a subject, to prevent rheumatoid arthritis from occurring and/or to cure or to alleviate rheumatoid arthritis symptoms, signs, or causes. A therapeutically effective amount also refers to the amount of a therapeutic necessary to mitigate or decrease at least one disease activity index and/or clinical symptom, and/or inhibit, delay, or reverse the progression of the condition and/or prevent or delay of the onset of a disease or illness. For an RA therapy, efficacy in vivo can, for example, be determined by using the ACR and/or European League Against Rheumatism (EULAR) clinical response parameters in the patients with RA, or by assaying a molecular determinant of the degree of RA in the patient.

The term "antagonist" is used in the broadest sense, and includes any molecule that partially or fully blocks, inhibits, or neutralizes a biological activity of a native polypeptide. In a similar manner, the term "agonist" is used in the broadest sense and includes any molecule that mimics a biological activity of a native polypeptide. Suitable agonist or antagonist molecules specifically include agonist or antagonist antibodies or antibody fragments, fragments or amino acid sequence variants of native polypeptides, small molecules inhibitors, and the like. Methods for identifying agonists or antagonists of a polypeptide may comprise contacting a polypeptide with a candidate agonist or antagonist molecule and measuring a detectable change in one or more biological activities normally associated with the polypeptide.

A "B cell antagonist" as used herein is any molecule that decreases, blocks, inhibits, abrogates, or interferes with signal transduction resulting from the interaction of a B cell with one or more of its interaction partners. In some embodiments, a B cell antagonist is a molecule that upon binding to a B cell surface marker, destroys or depletes B cells in a mammal and/or interferes with one or more B cell functions, e.g., by reducing or preventing a humoral response elicited by the B cell. The antagonist in certain instances is able to deplete B cells (i.e. reduce circulating B cell levels) in a mammal treated therewith. Such depletion may be achieved via various mechanisms such as ADCC and/or CDC, inhibition of B cell proliferation, and/or induction of B cell death (e.g. via apoptosis). In some embodiments, a "B cell antagonist" is a molecule that inhibits the binding of CD20 to its binding partners. In some embodiments, the B cell antagonist inhibits the activation of CD20. In some embodiments, the B cell antagonist includes an anti-CD20 antibody (e.g., rituximab), antigen-binding fragments thereof, an immunoadhesin, a fusion protein, an oligopeptide, and other molecules that decrease, block, inhibit, abrogate, or interfere with signal transduction resulting from the interaction of CD20 with one or more of its interaction partners. In some embodiments, the B cell antagonist is a polypeptide, a small molecule, or a nucleic acid. In some embodiments, the B cell antagonist (e.g., the B cell binding antagonist) inhibits CD20. In a particular embodiment, a B cell antagonist has a binding affinity (dissociation constant) to a B cell, or a molecule expressed on the surface thereof, of about 1,000 nM or less. In another embodiment, a B cell antagonist has a binding affinity to a B cell, or a molecule expressed on the surface thereof, of about 100 nM or less. In another embodiment, a B cell antagonist has a binding affinity to a B cell, or a molecule expressed on the surface thereof, of about 50 nM or less. In another embodiment, a B cell antagonist has a binding affinity to a B cell, or a molecule expressed on the surface thereof, of about 10 nM or less. In another embodiment, a B cell antagonist has a binding affinity to a B cell, or a molecule expressed on the surface thereof, of about 1 nM or less. In a particular embodiment, a B cell antagonist inhibits B cell signaling with an IC50 of 1,000 nM or less. In another embodiment, a B cell antagonist inhibits B cell signaling with an IC50 of 500 nM or less. In another embodiment, a B cell antagonist inhibits B cell signaling with an IC50 of 50 nM or less. In another embodiment, a B cell antagonist inhibits B cell signaling with an IC50 of 10 nM or less. In another embodiment, a B cell antagonist inhibits B cell signaling with an IC50 of 1 nM or less.

A "Janus kinase antagonist" or "JAK antagonist," as used interchangeably herein, is any molecule that decreases, blocks, inhibits, abrogates, or interferes with signal transduction resulting from the interaction of a Janus kinase with one or more of its interaction partners. In some embodiments, a Janus kinase antagonist is a molecule that upon binding to a Janus kinase, decreases, blocks, inhibits, abrogates, or interferes with JAK/Signal Transducer and Activator of Transcription (STAT) activation or function in a mammal treated therewith. In some embodiments, the Janus kinase antagonist includes an antibody (e.g., tofacitinib), antigen-binding fragments thereof, an immunoadhesin, a fusion protein, an oligopeptide, and other molecules that decrease, block, inhibit, abrogate, or interfere with signal transduction resulting from the interaction a Janus kinase with one or more of its interaction partners. In some embodiments, the Janus kinase antagonist is a polypeptide, a small molecule, or a nucleic acid. In some embodiments, the Janus kinase antagonist inhibits a Janus kinase. In a particular embodiment, a Janus kinase antagonist has a binding affinity (dissociation constant) to a Janus kinase of about 1,000 nM or less. In another embodiment, a Janus kinase antagonist has a binding affinity to a Janus kinase of about 100 nM or less. In another embodiment, a Janus kinase antagonist has a binding affinity to a Janus kinase of about 50 nM or less. In another embodiment, a Janus kinase antagonist has a binding affinity to a Janus kinase of about 10 nM or less. In another embodiment, a Janus kinase antagonist has a binding affinity to a Janus kinase of about 1 nM or less. In a particular embodiment, a Janus kinase antagonist inhibits Janus kinase signaling with an IC50 of 1,000 nM or less. In another embodiment, a Janus kinase antagonist inhibits Janus kinase signaling with an IC50 of 500 nM or less. In another embodiment, a Janus kinase antagonist inhibits Janus kinase signaling with an IC50 of 50 nM or less. In another embodiment, a Janus kinase antagonist Janus kinase signaling with an IC50 of 10 nM or less. In another embodiment, a Janus kinase antagonist inhibits Janus kinase signaling with an IC50 of 1 nM or less.

A "tumor necrosis factor antagonist" or "TNF antagonist," as used interchangeable herein, is any molecule that decreases, blocks, inhibits, abrogates, or interferes with signal transduction resulting from the interaction of a TNF with one or more of its interaction partners. In some embodiments, a TNF antagonist is a molecule that upon binding to a TNF, decreases, blocks, inhibits, abrogates, or interferes with TNF activation or function in a mammal treated therewith. In some embodiments, the TNF antagonist includes an antibody, antigen-binding fragments thereof, an immunoadhesin, a fusion protein, an oligopeptide, and other molecules that decrease, block, inhibit, abrogate, or interfere with signal transduction resulting from the interaction a TNF with one or more of its interaction partners. In some embodiments, the TNF antagonist is a polypeptide, a small molecule, or a nucleic acid. In some embodiments, the TNF antagonist inhibits TNF. In a particular embodiment, a TNF antagonist has a binding affinity (dissociation constant) to a TNF of about 1,000 nM or less. In another embodiment, a TNF antagonist has a binding affinity to a TNF of about 100 nM or less. In another embodiment, a TNF antagonist has a binding affinity to a TNF of about 50 nM or less. In another embodiment, a TNF has a binding affinity to a TNF of about 10 nM or less. In another embodiment, a TNF antagonist has a binding affinity to a TNF of about 1 nM or less. In a particular embodiment, a TNF antagonist inhibits TNF signaling with an IC50 of 1,000 nM or less. In another embodiment, a TNF antagonist inhibits TNF signaling with an IC50 of 500 nM or less. In another embodiment, a TNF antagonist TNF signaling with an IC50 of 50 nM or less. In another embodiment, a TNF antagonist TNF signaling with an IC50 of 10 nM or less. In another embodiment, a TNF antagonist inhibits TNF signaling with an IC50 of 1 nM or less.

A "decoy tumor necrosis factor receptor" or "decoy TNF receptor," as used interchangeable herein, is any molecule that decreases, blocks, inhibits, abrogates, or interferes with signal transduction resulting from the interaction of a TNF with one or more of its interaction partners. In some embodiments, a decoy TNF receptor is a molecule that upon binding to a TNF, decreases, blocks, inhibits, abrogates, or interferes with TNF activation or function in a mammal treated therewith. In some embodiments, the decoy TNF receptor includes an antibody, antigen-binding fragments thereof, an immunoadhesin, a fusion protein, an oligopeptide, and other molecules that decrease, block, inhibit, abrogate, or interfere with signal transduction resulting from the interaction a TNF with one or more of its interaction partners. In some embodiments, the decoy TNF receptor is a polypeptide, a small molecule, or a nucleic acid. In some embodiments, the decoy TNF receptor inhibits TNF. In a particular embodiment, a decoy TNF receptor has a binding affinity (dissociation constant) to a TNF of about 1,000 nM or less. In another embodiment, a decoy TNF receptor has a binding affinity to a TNF of about 100 nM or less. In another embodiment, a decoy TNF receptor has a binding affinity to a TNF of about 50 nM or less. In another embodiment, a decoy TNF receptor has a binding affinity to a TNF of about 10 nM or less. In another embodiment, a decoy TNF receptor has a binding affinity to a TNF of about 1 nM or less. In a particular embodiment, a decoy TNF receptor inhibits TNF signaling with an IC50 of 1,000 nM or less. In another embodiment, a decoy TNF receptor inhibits TNF signaling with an IC50 of 500 nM or less. In another embodiment, a decoy TNF receptor TNF signaling with an IC50 of 50 nM or less. In another embodiment, a decoy TNF receptor TNF signaling with an IC50 of 10 nM or less. In another embodiment, a decoy TNF receptor inhibits TNF signaling with an IC50 of 1 nM or less.

A "T cell costimulatory signal antagonist" as used herein is any molecule that decreases, blocks, inhibits, abrogates, or interferes with signal transduction resulting from the interaction of a T cell with one or more of its interaction partners. In some embodiments, a T cell costimulatory signal antagonist is a molecule that upon binding to a T cell, decreases, blocks, inhibits, abrogates, or interferes with the T cell. In some embodiments, a "T cell costimulatory signal antagonist" is a molecule that inhibits the binding of CD80 and CD86 to its binding partners. In some embodiments, the T cell costimulatory signal antagonist inhibits the activation of a T cell. In some embodiments, the T cell costimulatory signal antagonist includes an antibody, antigen-binding fragments thereof, an immunoadhesin, a fusion protein, an oligopeptide, and other molecules that decrease, block, inhibit, abrogate, or interfere with signal transduction resulting from the interaction of a T cell with one or more of its interaction partners. In some embodiments, the T cell costimulatory signal antagonist is a polypeptide, a small molecule, or a nucleic acid. In some embodiments, the T cell costimulatory signal antagonist inhibits a T cell. In a particular embodiment, a T cell costimulatory signal antagonist has a binding affinity (dissociation constant) to a T cell, or a molecule expressed on the surface thereof, of about 1,000 nM or less. In another embodiment, a T cell costimulatory signal antagonist has a binding affinity to a T cell, or a molecule expressed on the surface thereof, of about 100 nM or less. In another embodiment, a T cell costimulatory signal antagonist has a binding affinity to a T cell of about 50 nM or less. In another embodiment, a T cell costimulatory signal antagonist has a binding affinity to a T cell, or a molecule expressed on the surface thereof, of about 10 nM or less. In another embodiment, a T cell costimulatory signal antagonist has a binding affinity to a T cell, or a molecule expressed on the surface thereof, of about 1 nM or less. In a particular embodiment, a T cell costimulatory signal antagonist inhibits T cell signaling with an IC50 of 1,000 nM or less. In another embodiment, a T cell costimulatory signal antagonist inhibits T cell signaling with an IC50 of 500 nM or less. In another embodiment, a T cell costimulatory signal antagonist inhibits T cell signaling with an IC50 of 50 nM or less. In another embodiment, a T cell costimulatory signal antagonist inhibits T cell signaling with an IC50 of 10 nM or less. In another embodiment, a T cell costimulatory signal antagonist inhibits T cell signaling with an IC50 of 1 nM or less.

An "IL-1 receptor antagonist," "interleukin 1 receptor antagonist," or "IL-1R antagonist" as used interchangeably herein is any molecule that decreases, blocks, inhibits, abrogates, or interferes with signal transduction resulting from the interaction of IL-1 receptor with one or more of its interaction partners. In some embodiments, an IL-1 receptor antagonist is a molecule that upon binding to an IL-1 receptor, decreases, blocks, inhibits, abrogates, or interferes with IL-1R activation or function in a mammal treated therewith. In some embodiments, the IL-1 receptor antagonist includes an antibody, antigen-binding fragments thereof, an immunoadhesin, a fusion protein, an oligopeptide, and other molecules that decrease, block, inhibit, abrogate, or interfere with signal transduction resulting from the interaction of IL-1 receptor with one or more of its interaction partners. In some embodiments, the IL-1 receptor antagonist is a polypeptide, a small molecule, or a nucleic acid. In some embodiments, the IL-1 receptor antagonist (e.g., the IL-1 receptor binding antagonist) inhibits IL-1. In a particular embodiment, an IL-1R inhibitor has a binding affinity (dissociation constant) to IL-1R of about 1,000 nM or less. In another embodiment, an IL-1R antagonist has a binding affinity to IL-1R of about 100 nM or less. In another embodiment, an IL-1R antagonist has a binding affinity to IL-1R of about 50 nM or less. In another embodiment, an IL-1R antagonist has a binding affinity to IL-1R of about 10 nM or less. In another embodiment, an IL-1R antagonist has a binding affinity to IL-1R of about 1 nM or less. In a particular embodiment, an IL-1R antagonist inhibits IL-1R signaling with an IC50 of 1,000 nM or less. In another embodiment, an IL-1R antagonist inhibits IL-1R signaling with an IC50 of 500 nM or less. In another embodiment, an IL-1R antagonist inhibits IL-1R signaling with an IC50 of 50 nM or less. In another embodiment, an IL-1R antagonist inhibits IL-1R signaling with an IC50 of 10 nM or less. In another embodiment, an IL-1R antagonist inhibits IL-1R signaling with an IC50 of 1 nM or less.

An "IL-6 receptor antagonist," "interleukin 6 receptor antagonist," or "IL-6R antagonist," as used interchangeably herein, is any molecule that decreases, blocks, inhibits, abrogates, or interferes with signal transduction resulting from the interaction of IL-6 receptor with one or more of its interaction partners. In some embodiments, an IL-6 receptor antagonist is a molecule that upon binding to an IL-6 receptor, decreases, blocks, inhibits, abrogates, or interferes with IL-6R activation or function in a mammal treated therewith. In some embodiments, the IL-6 receptor antagonist includes an antibody (e.g., tocilizumab), antigen-binding fragments thereof, an immunoadhesin, a fusion protein, an oligopeptide, and other molecules that decrease, block, inhibit, abrogate, or interfere with signal transduction resulting from the interaction of IL-6 receptor with one or more of its interaction partners. In some embodiments, the IL-6 receptor antagonist is a polypeptide, a small molecule, or a nucleic acid. In some embodiments, the IL-6 receptor antagonist (e.g., the IL-6 receptor binding antagonist) inhibits IL-6. In a particular embodiment, an IL-6R antagonist has a binding affinity (dissociation constant) to IL-6R of about 1,000 nM or less. In another embodiment, an IL-6R antagonist has a binding affinity to IL-6R of about 100 nM or less. In another embodiment, an IL-6R antagonist has a binding affinity to IL-6R of about 50 nM or less. In another embodiment, an IL-6R antagonist has a binding affinity to IL-6R of about 10 nM or less. In another embodiment, an IL-6R antagonist has a binding affinity to IL-6R of about 1 nM or less. In a particular embodiment, an IL-6R antagonist inhibits IL-6R signaling with an IC50 of 1,000 nM or less. In another embodiment, an IL-6R antagonist inhibits IL-6R signaling with an IC50 of 500 nM or less. In another embodiment, an IL-6R antagonist inhibits IL-6R signaling with an IC50 of 50 nM or less. In another embodiment, an IL-6R antagonist inhibits IL-6R signaling with an IC50 of 10 nM or less. In another embodiment, an IL-6R antagonist inhibits IL-6R signaling with an IC50 of 1 nM or less.

The term "antibody" herein is used in the broadest sense and specifically covers monoclonal antibodies, polyclonal antibodies, half-antibodies, multispecific antibodies (e.g., bispecific antibodies) formed from at least two intact antibodies, and antibody fragments so long as they exhibit the desired biological activity. The term "immunoglobulin" (Ig) is used interchangeably with antibody herein.

A "blocking" antibody or an antibody "antagonist" is one which inhibits or reduces biological activity of the antigen it binds. For example, an IL-6 receptor antagonist antibody binds IL-6 receptor and decreases, blocks, inhibits, abrogates, or interferes with signal transduction resulting from the interaction of IL-6 receptor with IL-6. Preferred blocking antibodies or antagonist antibodies completely inhibit the biological activity of the antigen.

An "article of manufacture" is any manufacture (e.g., a package or container) or kit comprising at least one reagent, e.g., a medicament for treatment of a disease or disorder (e.g., RA), or a probe for specifically detecting a biomarker (e.g., one or more of CD180, CSF2, CXCL1, DENND1C, MMP10, SDC1, and UBASH3A) described herein. In certain embodiments, the manufacture or kit is promoted, distributed, or sold as a unit for performing the methods described herein.

The term "package insert" is used to refer to instructions customarily included in commercial packages of therapeutic products, that contain information about the indications, usage, dosage, administration, combination therapy, contraindications, and/or warnings concerning the use of such therapeutic products.

A "sterile" formulation is aseptic or free from all living microorganisms and their spores.

The phrase "based on" when used herein means that the information about one or more biomarkers is used to inform a treatment decision, information provided on a package insert, or marketing/promotional guidance.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

"Disease progression" or "progression" as used interchangeably herein, refers to radiographic progression and/or increased disease activity. Radiographic progression can be defined, for example, by an increase in ShSS (e.g., an increase in ShSS over a defined time period). For example, the time period may be, at a minimum, one year after initial examination.

"Disease activity" or "rheumatoid arthritis disease activity" as used herein, refer to the severity or intensity of rheumatoid arthritis and can be determined by, for example, ACR and/or EULAR clinical indices including, but not limited to, DAS28-ESR, DAS28-CRP, levels of ESR, CRP, ACPA titer, RF titer, swollen joint counts, VAS, assessment of joint damage (e.g., by x-ray, Ultrasound Synovial Thickening (USST) assessment, or Ultrasound Power Doppler scores (USPD)), or a combination thereof. A DAS28-ESR of <3.2 is indicative of low disease activity, while a DAS28-ESR of 3.2-5.1 is indicative of moderate disease activity, and a DAS28-ESR of >5.1 is indicative of the most severe disease activity. RF titer seropositivity indicates high disease activity, while RF seronegativity indicates low disease activity. An ESR level of greater than 28 mm/Hr, a CRP level of greater than 1 mg/dL, a positive ACPA titer, swollen joint counts of at least one, and/or the presence of erosion or joint space narrowing by X-ray are abnormal and indicative of disease activity.

"Responsiveness" or "effective response" can be assessed using any endpoint indicating a benefit to the individual and includes, without limitation, (i) inhibition, to some extent, of disease progression, including slowing down and complete arrest; (ii) reduction in the number of disease episodes and/or symptoms; (iii) reduction in lesional size; (iv) inhibition (i.e., reduction, slowing down or complete stopping) of disease cell infiltration into adjacent peripheral organs and/or tissues; (v) inhibition (i.e. reduction, slowing down or complete stopping) of disease spread; (vi) decrease of autoimmune response, which may, but does not have to, result in the regression or ablation of the disease lesion; (vii) relief, to some extent, of one or more symptoms associated with the disorder; (viii) increase in the length of disease-free presentation following treatment; and/or (ix) decreased mortality at a given point of time following treatment.

II. Methods

Provided herein are methods and assays for diagnosing a patient having rheumatoid arthritis (RA); identifying an individual having RA who is likely to exhibit disease progression; identifying an individual having RA who may benefit from a treatment including a therapeutic agent other than, or in addition to, a disease modifying anti-rheumatic drug (DMARD); identifying an individual having RA who may benefit from a treatment including a DMARD; determining whether an individual having RA is likely to respond to treatment with an RA therapy that includes a DMARD; selecting a therapy for an individual having RA; treating an individual having RA based on a diagnostic method of the invention; optimizing therapeutic efficacy of an RA therapy; and monitoring therapeutic efficacy of an RA therapy. The methods and assays described herein are based on the finding that the expression level of at least one or more biomarkers described herein in a sample (e.g., a synovial tissue sample, a synovial fluid sample, or a combination thereof) from an individual having RA can be used to predict the therapeutic efficacy of an RA therapy, for example, a DMARD (i.e., a DMARD), or a therapy including a biologic therapeutic agent (i.e., a biologic therapeutic agent), alone or in combination with a DMARD. Any of the methods and assays may further include determining a myeloid, lymphoid, and/or pauciimmune-fibroid eigengene score. Any of the methods and assays provided herein may further include administering a DMARD (e.g., a DMARD described in Section II-B below) to the individual. Accordingly, provided herein are also methods and assays of evaluating the expression of one or more biomarkers in a sample from an individual. Any of the methods provided herein may include administering an RA therapy other than, or in additional to, a DMARD (e.g., an RA therapy other than, or in additional to, a DMARD described in Section II-B, below) to the individual. Any of the methods may further include administering an effective amount of an additional therapeutic agent, as described herein, to the individual.

A. Diagnostic Methods and Assays (i) Prognostic Diagnostic Methods and Assays

The present invention provides methods that may be used to identify an individual having RA who is likely to exhibit disease progression, the methods and assays including determining an expression level of one or more genes set forth in Table 1 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 46 genes set forth in Table 1) in a sample from the individual, wherein a change in the expression level of the one or more genes relative to a reference expression level identifies the individual as one who is more likely to exhibit disease progression.

TABLE 1

| NCBI Gene ID | Gene Name | NCBI Gene ID | Gene Name |
| --- | --- | --- | --- |
| 4064 | CD180 | 27177 | IL36B |
| 1437 | CSF2 | 3662 | IRF4 |
| 2919 | CXCL1 | 100505746 | ITGB2-AS1 |
| 79958 | DENND1C | 4063 | LY9 |
| 4319 | MMP10 | 11184 | MAP4K1 |
| 6382 | SDC1 | 4312 | MMP1 |
| 53347 | UBASH3A | 9241 | NOG |
| 640 | BLK | 11040 | PIM2 |
| 695 | BTK | 5450 | POU2AF1 |
| 151888 | BTLA | 399 | RHOH |
| 6363 | CCL19 | 23231 | SEL1L3 |
| 930 | CD19 | 55423 | SIRPG |
| 952 | CD38 | 114836 | SLAMF6 |
| 959 | CD40LG | 1317 | SLC31A1 |
| 8483 | CILP | 6689 | SPIB |
| 79961 | DENND2D | 201633 | TIGIT |
| 27122 | DKK3 | 81793 | TLR10 |
| 83416 | FCRL5 | 11322 | TMC6 |
| 2247 | FGF2 | 7124 | TNF |
| 2254 | FGF9 | 4982 | TNFRSF11B |
| 3112 | HLA-DOB | 608 | TNFRSF17 |
| 29851 | ICOS | 80342 | TRAF3PIP3 |
| 3512 | JCHAIN | 7494 | XBP1 |

In some instances, the methods and assays provided herein may involve determining an expression level of one or more genes set forth Table 2 (e.g., 1, 2, 3, 4, 5, 6, 7, 8, 9, 10, 11, 12, 13, 14, 15, 16, 17, 18, 19, 20, 21, 21, 22, 23, 24, 25, 26, 27, 28, 29, 30, 31, 32, 33, 34, 35, 36, 37, 38, 39, or 40 genes set forth in Table 2) or Table 3 (e.g., 1, 2, 3, 4, 5, or 6 genes set forth in Table 3) in a sample from an individual, wherein a change in the expression level of the one or more genes set forth in Table 2 or Table 3 relative to a reference expression level identifies the individual as one who is more likely to exhibit disease progression.

TABLE 2

| NCBI Gene ID | Gene Name | NCBI Gene ID | Gene Name |
| --- | --- | --- | --- |
| 640 | BLK | 11184 | MAP4K1 |
| 695 | BTK | 4312 | MMP1 |
| 151888 | BTLA | 4319 | MMP10 |
| 6363 | CCL19 | 11040 | PIM2 |
| 4064 | CD180 | 5450 | POU2AF1 |
| 930 | CD19 | 399 | RHOH |
| 952 | CD38 | 6382 | SDC1 |
| 959 | CD40LG | 23231 | SEL1L3 |
| 1437 | CSF2 | 55423 | SIRPG |
| 2919 | CXCL1 | 114836 | SLAMF6 |
| 79958 | DENND1C | 1317 | SLC31A1 |
| 79961 | DENND2D | 6689 | SPIB |
| 83416 | FCRL5 | 201633 | TIGIT |
| 3112 | HLA-DOB | 81793 | TLR10 |
| 29851 | ICOS | 11322 | TMC6 |
| 3512 | JCHAIN | 7124 | TNF |
| 27177 | IL36B | 608 | TNFRSF17 |
| 3662 | IRF4 | 80342 | TRAF3PIP3 |
| 100505746 | ITGB2-AS1 | 53347 | UBASH3A |
| 4063 | LY9 | 7494 | XBP1 |

TABLE 3

| NCBI Gene ID | Gene Name |
| --- | --- |
| 8483 | CILP |
| 27122 | DKK3 |

TABLE 3-continued

| NCBI Gene ID | Gene Name |
|---|---|
| 2247 | FGF2 |
| 2254 | FGF9 |
| 9241 | NOG |
| 4982 | TNFRSF11B |

In some instances, the methods and assays provided herein may involve determining an expression level of one or more genes set forth in Table 2 (e.g., 1, 2, 3, 4, 5, 6, 7, 8, 9, 10, 11, 12, 13, 14, 15, 16, 17, 18, 19, 20, 21, 21, 22, 23, 24, 25, 26, 27, 28, 29, 30, 31, 32, 33, 34, 35, 36, 37, 38, 39, or 40 genes set forth in Table 2). For example, the method may include determining the expression level of one or more genes set forth in Table 2, wherein an increase in the expression level (e.g., an increase in the expression level of about 10%, 20%, 30%, 40%, 50%, 60%, 70%, 80%, 90%, 95%, 96%, 97%, 98%, or 99% or greater) of the one or more genes set forth in Table 2 relative to a reference expression level identifies the individual as one who is more likely to exhibit disease progression. In certain instances, the increased expression level of the one or more genes set forth in Table 2 (e.g., 1, 2, 3, 4, 5, 6, 7, 8, 9, 10, 11, 12, 13, 14, 15, 16, 17, 18, 19, 20, 21, 21, 22, 23, 24, 25, 26, 27, 28, 29, 30, 31, 32, 33, 34, 35, 36, 37, 38, 39, or 40 genes set forth in Table 2) is an increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference expression level of the one or more genes. In some instances, the increased expression level of the one or more genes set forth in Table 2 (e.g., 1, 2, 3, 4, 5, 6, 7, 8, 9, 10, 11, 12, 13, 14, 15, 16, 17, 18, 19, 20, 21, 21, 22, 23, 24, 25, 26, 27, 28, 29, 30, 31, 32, 33, 34, 35, 36, 37, 38, 39, or 40 genes set forth in Table 2) is an increase of at least about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, or about 1,000-fold or greater relative to a reference expression level of the one or more genes.

In particular instances, the methods and assays may include determining an expression level of one or more genes selected from CD180, CSF2, CXCL1, DENND1C, MMP10, SDC1, and UBASH3A (e.g., 1, 2, 3, 4, 5, 6, or 7 genes selected from CD180, CSF2, CXCL1, DENND1C, MMP10, SDC1, and UBASH3A) in a sample from an individual. For example, the method or assay may include determining the expression level of one or more genes selected from CD180, CSF2, CXCL1, DENND1C, MMP10, SDC1, and UBASH3A, wherein an increase in the expression level (e.g., an increase in the expression level of about 10%, 20%, 30%, 40%, 50%, 60%, 70%, 80%, 90%, 95%, 96%, 97%, 98%, or 99% or greater) of the one or more genes selected from CD180, CSF2, CXCL1, DENND1C, MMP10, SDC1, and UBASH3A relative to a reference expression level identifies the individual as one who is more likely to exhibit disease progression. In certain instances, the increased expression level of the one or more genes selected from CD180, CSF2, CXCL1, DENND1C, MMP10, SDC1, and UBASH3A (e.g., 1, 2, 3, 4, 5, 6, or 7 genes selected from CD180, CSF2, CXCL1, DENND1C, MMP10, SDC1, and UBASH3A) is an increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference expression level of the one or more genes. In some instances, the increased expression level of one or more of CD180, CSF2, CXCL1, DENND1C, MMP10, SDC1, and UBASH3A (e.g., 1, 2, 3, 4, 5, 6, or 7 genes selected from CD180, CSF2, CXCL1, DENND1C, MMP10, SDC1, and UBASH3A) is an increase of at least about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, or about 1,000-fold or greater relative to a reference expression level of the one or more genes.

In particular instances, the method and assays may include determining an expression level of at least two of CD180, CSF2, CXCL1, DENND1C, MMP10, SDC1, and UBASH3A in a sample from an individual that is increased (e.g., an increased expression level of about 10%, 20%, 30%, 40%, 50%, 60%, 70%, 80%, 90%, 95%, 96%, 97%, 98%, or 99% or greater) relative to a reference expression level of the at least two genes identifies the individual as one who is likely to exhibit disease progression. In certain instances, the increased expression level of at least two of the following genes: CD180, CSF2, CXCL1, DENND1C, MMP10, SDC1, and UBASH3A, is an increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference expression level of the at least two genes. In some instances, the increased expression level of at least two of the following genes: CD180, CSF2, CXCL1, DENND1C, MMP10, SDC1, and UBASH3A, is an increase of at least about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, or about 1,000-fold or greater relative to a reference expression level of the at least two genes. In some instances of the diagnostic method, the expression levels of a combination of two genes set forth in Table 1, such as any of the exemplary combinations shown in Table 4, may be determined.

TABLE 4

Two-Gene Combinations of CD180, CSF2, CXCL1, DENND1C, MMP10, SDC1, and UBASH3A

CD180 and CSF2
CD180 and CXCL1
CD180 and DENND1C

TABLE 4-continued

Two-Gene Combinations of CD180, CSF2, CXCL1, DENND1C, MMP10, SDC1, and UBASH3A

CD180 and MMP10
CD180 and SDC1
CD180 and UBASH3A
CSF2 and CXCL1
CSF2 and DENND1C
CSF2 and MMP10
CSF2 and SDC1
CSF2 and UBASH3A
CXCL1 and DENND1C
CXCL1 and MMP10
CXCL1 and SDC1
CXCL1 and UBASH3A
DENND1C and MMP10
DENND1C and SDC1
DENND1C and UBASH3A
MMP10 and SDC1
MMP10 and UBASH3A
SDC1 and UBASH3A In particular instances, the method and assays may include determining an expression level of at least three of CD180, CSF2, CXCL1, DENND1C, MMP10, SDC1, and UBASH3A in a sample from an individual that is increased (e.g., an increased expression level of about 10%, 20%, 30%, 40%, 50%, 60%, 70%, 80%, 90%, 95%, 96%, 97%, 98%, or 99% or greater) relative to a reference expression level of the at least three genes identifies the individual as one who is likely to exhibit disease progression. In certain instances, the increased expression level of at least three of the following genes: CD180, CSF2, CXCL1, DENND1C, MMP10, SDC1, and UBASH3A, is an increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference expression level of the at least three genes. In some instances, the increased expression level of at least three of the following genes: CD180, CSF2, CXCL1, DENND1C, MMP10, SDC1, and UBASH3A, is an increase of at least about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, or about 1,000-fold or greater relative to a reference expression level of the at least three genes. In some instances of the diagnostic method, the expression levels of a combination of three genes set forth in Table 1, such as any of the exemplary combinations shown in Table 5, may be determined.

TABLE 5

Three-Gene Combinations of CD180, CSF2, CXCL1, DENND1C, MMP10, SDC1, and UBASH3A CD180, CSF2, and CXCL1
CD180, CSF2, and DENND1C
CD180, CSF2, and MMP10
CD180, CSF2, and SDC1
CD180, CSF2, and UBASH3A
CD180, CXCL1, and DENND1C
CD180, CXCL1, and MMP10
CD180, CXCL1, and SDC1

TABLE 5-continued

Three-Gene Combinations of CD180, CSF2, CXCL1, DENND1C, MMP10, SDC1, and UBASH3A CD180, CXCL1, and UBASH3A
CD180, DENND1C, and MMP10
CD180, DENND1C, and SDC1
CD180, DENND1C, and UBASH3A
CD180, MMP10, and SDC1
CD180, MMP10, and UBASH3A
CD180, SDC1, and UBASH3A
CSF2, CXCL1 and DENND1C
CSF2, CXCL1, and MMP10
CSF2, CXCL1, and SDC1
CSF2, CXCL1, and UBASH3A
CSF2, DENND1C, and MMP10
CSF2, DENND1C, and SDC1
CSF2, DENND1C, and UBASH3A
CSF2, MMP10, and SDC1
CSF2, MMP10, and UBASH3A
CSF2, SDC1, and UBASH3A
CXCL1, DENND1C, and MMP10
CXCL1, DENND1C and SDC1
CXCL1, DENND1C, and UBASH3A
CXCL1, MMP10, and SDC1
CXCL1, MMP10, and UBASH3A
CXCL1, SDC1, and UBASH3A
DENND1C, MMP10, and SDC1
DENND1C, MMP10, and UBASH3A
DENND1C, SDC1, and UBASH3A
MMP10, SDC1, and UBASH3A In particular instances, the method and assays may include determining an expression level of at least four of CD180, CSF2, CXCL1, DENND1C, MMP10, SDC1, and UBASH3A in a sample from an individual that is increased (e.g., an increased expression level of about 10%, 20%, 30%, 40%, 50%, 60%, 70%, 80%, 90%, 95%, 96%, 97%, 98%, or 99% or greater) relative to a reference expression level of the at least four genes identifies the individual as one who is likely to exhibit disease progression. In certain instances, the increased expression level of at least four of the following genes: CD180, CSF2, CXCL1, DENND1C, MMP10, SDC1, and UBASH3A, is an increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference expression level of the at least four genes. In some instances, the increased expression level of at least four of the following genes: CD180, CSF2, CXCL1, DENND1C, MMP10, SDC1, and UBASH3A, is an increase of at least about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, or about 1,000-fold or greater relative to a reference expression level of the at least four genes. In some instances of the diagnostic methods, the expression levels of a combination of four genes set forth in Table 1, such as any of the exemplary combinations shown in Table 6, may be determined.

TABLE 6

Four-Gene Combinations of CD180, CSF2, CXCL1, DENND1C, MMP10, SDC1, and UBASH3A

CD180, CSF2, CXCL1, and DENND1C
CD180, CSF2, CXCL1, and MMP10
CD180, CSF2, CXCL1, and SDC1
CD180, CSF2, CXCL1, and UBASH3A
CD180, CSF2, DENND1C, and MMP10
CD180, CSF2, DENND1C, and SDC1
CD180, CSF2, DENND1C, and UBASH3A
CD180, CSF2, MMP10, and SDC1
CD180, CSF2, MMP10, and UBASH3A
CD180, CSF2, SDC1, and UBASH3A
CD180, CXCL1, DENND1C, and MMP10
CD180, CXCL1, DENND1C, and SDC1
CD180, CXCL1, DENND1C, and UBASH3A
CD180, CXCL1, MMP10, and SDC1
CD180, CXCL1, MMP10, and UBASH3A
CD180, CXCL1, SDC1, and UBASH3A
CD180, DENND1C, MMP10, and SDC1
CD180, DENND1C, MMP10, and UBASH3A
CD180, DENND1C, SDC1, and UBASH3A
CD180, MMP10, SDC1, and UBASH3A
CSF2, CXCL1, DENND1C, and MMP10
CSF2, CXCL1, DENND1C, and SDC1
CSF2, CXCL1, DENND1C, and UBASH3A
CSF2, CXCL1, MMP10, and SDC1
CSF2, CXCL1, MMP10, and UBASH3A
CSF2, CXCL1, SDC1, and UBASH3A
CSF2, DENND1C, MMP10, and SDC1
CSF2, DENND1C, MMP10, and UBASH3A
CSF2, DENND1C, SDC1, and UBASH3A
CSF2, MMP10, SDC1, and UBASH3A
CXCL1, DENND1C, MMP10, and SDC1
CXCL1, DENND1C, MMP10, and UBASH3A
CXCL1, DENND1C, SDC1, and UBASH3A
CXCL1, MMP10, SDC1, and UBASH3A
DENND1C, MMP10, SDC1, and UBASH3A In particular instances, the method and assays may include determining an expression level of at least five of CD180, CSF2, CXCL1, DENND1C, MMP10, SDC1, and UBASH3A in the sample from an individual that is increased (e.g., an increased expression level of about 10%, 20%, 30%, 40%, 50%, 60%, 70%, 80%, 90%, 95%, 96%, 97%, 98%, or 99% or greater) relative to a reference expression level of the at least five genes identifies the individual as one who is likely to exhibit disease progression. In certain instances, the increased expression level of at least five of the following genes: CD180, CSF2, CXCL1, DENND1C, MMP10, SDC1, and UBASH3A, is an increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference expression level of the at least five genes. In some instances, the increased expression level of at least five of the following genes: CD180, CSF2, CXCL1, DENND1C, MMP10, SDC1, and UBASH3A, is an increase of at least about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, or about 1,000-fold or greater relative to a reference expression level of the at least five genes. In some instances of the diagnostic methods, the expression levels of a combination of five genes set forth in Table 1, such as any of the exemplary combinations shown in Table 7, may be determined.

TABLE 7

Five-Gene Combinations of CD180, CSF2, CXCL1, DENND1C, MMP10, SDC1, and UBASH3A

CD180, CSF2, CXCL1, DENND1C, and MMP10
CD180, CSF2, CXCL1, DENND1C, and SDC1
CD180, CSF2, CXCL1, DENND1C, and UBASH3A
CD180, CSF2, CXCL1, MMP10, and SDC1
CD180, CSF2, CXCL1, MMP10, and UBASH3A
CD180, CSF2, CXCL1, SDC1, and UBASH3A
CD180, CSF2, DENND1C, MMP10, and SDC1
CD180, CSF2, DENND1C, MMP10, and UBASH3A
CD180, CSF2, DENND1C, SDC1, and UBASH3A
CD180, CSF2, MMP10, SDC1, and UBASH3A
CD180, CXCL1, DENND1C, MMP10, and SDC1
CD180, CXCL1, DENND1C, MMP10, and UBASH3A
CD180, CXCL1, DENND1C, SDC1, and UBASH3A
CD180, CXCL1, MMP10, SDC1, and UBASH3A
CD180, DENND1C, MMP10, SDC1, and UBASH3A
CSF2, CXCL1, DENND1C, MMP10, and SDC1
CSF2, CXCL1, DENND1C, MMP10, and UBASH3A
CSF2, CXCL1, DENND1C, SDC1, and UBASH3A
CSF2, CXCL1, MMP10, SDC1, and UBASH3A
CSF2, DENND1C, MMP10, SDC1, and UBASH3A
CXCL1, DENND1C, MMP10, SDC1, and UBASH3A In particular instances, the method and assays may include determining an expression level of at least six of CD180, CSF2, CXCL1, DENND1C, MMP10, SDC1, and UBASH3A in a sample that is increased (e.g., an increased expression level of about 10%, 20%, 30%, 40%, 50%, 60%, 70%, 80%, 90%, 95%, 96%, 97%, 98%, or 99% or greater) relative to a reference expression level of the at least six genes identifies the individual as one who is likely to exhibit disease progression. In certain instances, the increased expression level of at least six of the following genes: CD180, CSF2, CXCL1, DENND1C, MMP10, SDC1, and UBASH3A, is an increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference expression level of the at least six genes. In some instances, the increased expression level of at least six of the following genes: CD180, CSF2, CXCL1, DENND1C, MMP10, SDC1, and UBASH3A, is an increase of at least about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, or about 1,000-fold or greater relative to a reference expression level of the at least six genes. In some instances of the diagnostic methods, the expression levels of a combination of six genes set forth in Table 1, such as any of the exemplary combinations shown in Table 8, may be determined.

TABLE 8

Six-Gene Combinations of CD180, CSF2, CXCL1, DENND1C, MMP10, SDC1, and UBASH3A

CD180, CSF2, CXCL1, DENND1C, MMP10, and SDC1
CD180, CSF2, CXCL1, DENND1C, MMP10, and UBASH3A
CD180, CSF2, CXCL1, DENND1C, SDC1, and UBASH3A
CD180, CSF2, CXCL1, MMP10, SDC1, and UBASH3A
CD180, CSF2, DENND1C, MMP10, SDC1, and UBASH3A
CD180, CXCL1, DENND1C, MMP10, SDC1, and UBASH3A
CSF2, CXCL1, DENND1C, MMP10, SDC1, and UBASH3A In particular instances, the method and assays may include determining an expression level of the seven following genes: CD180, CSF2, CXCL1, DENND1C, MMP10, SDC1, and UBASH3A in a sample that is increased (e.g., an increased expression level of about 10%, 20%, 30%, 40%, 50%, 60%, 70%, 80%, 90%, 95%, 96%, 97%, 98%, or 99% or greater) relative to a reference expression level of the seven genes identifies the individual as one who is likely to exhibit disease progression. In certain instances, the increased expression level of the seven following genes: CD180, CSF2, CXCL1, DENND1C, MMP10, SDC1, and UBASH3A, is an increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference expression level of the seven genes. In some instances, the increased expression level of the seven following genes: CD180, CSF2, CXCL1, DENND1C, MMP10, SDC1, and UBASH3A, is an increase of at least about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, or about 1,000-fold or greater relative to a reference expression level of the seven genes.

In some instances, the methods and assays provided herein may involve determining an expression level of one or more genes set forth in Table 3 (e.g., 1, 2, 3, 4, 5, or 6 genes set forth in Table 3) in a sample from an individual. For example, the method or assay may include determining the expression level of one or more genes set forth in Table 3, wherein a decrease in expression level (e.g., a decrease in the expression level of about 10%, 20%, 30%, 40%, 50%, 60%, 70%, 80%, 90%, 95%, 96%, 97%, 98%, or 99% or greater) of the one or more genes set forth in Table 3 relative to a reference expression level identifies the individual as one who is more likely to exhibit disease progression. In certain instances, the decreased expression level of one or more genes set forth in Table 3 (e.g., 1, 2, 3, 4, 5, or 6 genes set forth in Table 3) is a decrease of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference expression level of the one or more genes. In some instances, the decreased expression level of one or more genes set forth in Table 3 (e.g., 1, 2, 3, 4, 5, or 6 genes set forth in Table 3) is a decrease of at least about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, or about 1,000-fold or greater relative to a reference expression level of the one or more genes.

In any of the prognostic methods and assays described above, the reference expression level may be a reference expression level in a reference population of individuals having RA who have not been previously treated with a DMARD, the population of individuals consisting of a first subset of individuals who exhibited disease progression and a second subset of individuals who did not exhibit disease progression. In some instances, the reference expression level significantly separates each of the first and second subsets of individuals based on a significant difference in the expression level of the one or more genes set forth in Table 1, Table 2, or Table 3 in the first subset of individuals compared to that of the second subset of individuals. In some instances, the first subset of individuals exhibited disease progression, and the second subset of individuals did not exhibit disease progression after about 12 months.

In any of the prognostic methods and assays described above in which the expression level of one or more biomarkers, selected from the biomarkers set forth in Table 1, Table 2, or Table 3, are determined in a sample from an individual and compared to a reference expression level (e.g., a pre-assigned expression level of the one or more genes set forth in Table 1, Table 2, or Table 3), it is to be understood that, in some instances, the expression level of the one or more biomarkers may be an average of the expression level of the one or more biomarkers. In some instances, the expression level of the one or more biomarkers may be a median of the expression level of the one or more biomarkers. In some instances, the expression level the one or more biomarkers may be normalized, e.g., to a reference gene, e.g., a housekeeping gene. In some instances, the reference gene is ACTB, GAPDH, GUSB, HPRT1, PGK1, RPL19, TUBB, or TMEM55B. In some instances, the expression level of the one or more biomarkers may be an average of a normalized expression level of the one or more biomarkers. In some instances, the expression level of the one or more biomarkers may be a median of a normalized expression level of the one or more biomarkers.

In any of the prognostic methods and assays described above in which the expression level of more than one biomarker, selected from the genes set forth in Table 1, Table 2, or Table 3, is determined in a sample from an individual and compared to a reference expression level (e.g., a pre-assigned expression level of the one or more genes set forth in Table 1, Table 2, or Table 3), it is to be understood that, in some instances, the expression level of each individual biomarker in the sample is compared to a reference expression level for each individual biomarker. For example, if the expression level of CD180 and CXCL1 are determined in a sample from an individual and compared to reference expression levels for CD180 and CXCL1, in some instances, the expression level of CD180 in the sample from the individual is compared to the reference expression level for CD180, and the expression level of CXCL1 in the sample from the individual is compared to the reference expression level for CXCL1. In other instances, an expression level for more than one gene of interest may be determined by aggregation methods known to one skilled in the art and also disclosed herein, including, for example, by calculating the median or mean of all the expression levels of the genes of interest. Before aggregation, the expression level of each gene of interest may be normalized by using statistical methods known to one skilled in the art and also disclosed herein, including, for example, normalized to the expression level of one or more housekeeping genes, or normalized to a total library size, or normalized to the median or mean expression level value across all genes measured. In some instances, before aggregation across multiple genes of interest, the normalized expression level of each gene of interest may be standardized by using statistical methods known to one skilled in the art and also disclosed herein, including, for example, by calculating the Z-score of the normalized expression level of each gene of interest.

In any of the prognostic methods and assays described above, the disease progression may be radiographic progression. The radiographic progression may be characterized by an increase in ShSS (e.g., an increase in ShSS over a defined time period).

The present invention also provides methods and assays that may be used to identify an individual having RA who may be more likely to exhibit disease activity that involves determining a myeloid eigengene score from a sample from the individual, wherein a myeloid eigengene score from the sample that is at or above a reference myeloid eigengene score identifies the individual as one who may be more likely to exhibit disease activity. In some instances, the methods and assays provided herein may further involve determining a lymphoid eigengene score from the sample from the individual, wherein a lymphoid eigengene score from the sample that is at or above a reference lymphoid eigengene score identifies the individual as one who may be more likely to exhibit disease activity.

The present invention provides methods and assays that may be used to identify an individual having RA who may be less likely to exhibit disease activity that involves determining a pauciimmune-fibroid eigengene score from a sample from the individual, wherein a pauciimmune-fibroid eigengene score from the sample that is at or above a reference pauciimmune-fibroid eigengene score identifies the individual as one who may be less likely to exhibit disease activity.

In any of the prognostic methods and assays described above, the reference myeloid eigengene score may be a reference myeloid eigengene score in a reference population of individuals having RA, the population of individuals consisting of a first subset of individuals who exhibited disease activity and a second subset of individuals who did not exhibit disease activity. In some instances, the reference myeloid eigengene score level significantly separates each of the first and second subsets of individuals based on a significant difference in the myeloid eigengene score in the first subset of individuals compared to that of the second subset of individuals.

In any of the prognostic methods and assays described above, the reference lymphoid eigengene score may be a reference lymphoid eigengene score in a reference population of individuals having RA, the population of individuals consisting of a first subset of individuals who exhibited disease activity and a second subset of individuals who did not exhibit disease activity. In some instances, the reference lymphoid eigengene score level significantly separates each of the first and second subsets of individuals based on a significant difference in the lymphoid eigengene score in the first subset of individuals compared to that of the second subset of individuals.

In any of the prognostic methods and assays described above, the reference pauciimmune-fibroid eigengene score may be a reference pauciimmune-fibroid eigengene score in a reference population of individuals having RA, the population of individuals consisting of a first subset of individuals who exhibited disease activity and a second subset of individuals who did not exhibit disease activity. In some instances, the reference pauciimmune-fibroid eigengene score level significantly separates each of the first and second subsets of individuals based on a significant difference in the pauciimmune-fibroid eigengene score in the first subset of pauciimmune-fibroid compared to that of the second subset of individuals.

In any of the prognostic methods and assays described above, the severity of disease activity may be assessed by evaluating, for example, ACR and/or EULAR clinical indices including, but not limited to, DAS28-ESR, DAS28-CRP, levels of ESR, CRP, ACPA titer, assessment of joint damage (e.g., by x-ray, Ultrasound Synovial Thickening (USST) assessment, or Ultrasound Power Doppler (USPD) scores), or a combination thereof.

In any of the prognostic methods and assays described above, the methods and assays may further include determining one or more clinical covariates (e.g., baseline RF titer, disease duration, DAS28-ESR, DAS28-CRP, baseline pathotype, and 12 max USST and USPD scores) of the individual.

In any of the prognostic methods and assays described above, the methods and assays may further include administering to the individual a therapeutic agent other than, or in addition to, a disease modifying anti-rheumatic drug (DMARD) (e.g., as described in Section II-B, below). In particular instances, when the change in expression level of the one or more genes set forth in Table 1 or Table 2 relative to a reference expression level is an increase, the method further includes administering to the individual a therapeutic agent other than, or in addition to, a disease modifying anti-rheumatic drug (DMARD). In particular instances, when the change in expression level of the one or more genes set forth in Table 3 relative to a reference expression level is a decrease, the method further includes administering to the individual a therapeutic agent other than, or in addition to, a disease modifying anti-rheumatic drug (DMARD).

In some instances of any of the preceding methods and assays described above, the RA therapeutic agent may be a DMARD (e.g., as described in Section II-B below). In some instances of any of the preceding methods described above, the RA therapeutic agent may be a therapeutic agent other than a DMARD (e.g., as described in Section II-B below).

In some instances, the individual has not been previously treated with a DMARD. In other instances, the individual has been previously treated with a DMARD.

(ii) Predictive Diagnostic Methods and Assays

The present invention provides methods and assays of identifying an individual having RA who may benefit from a treatment with an RA therapy that includes a DMARD (e.g., methotrexate) that involves determining a myeloid eigengene score from a sample from the individual, wherein a myeloid eigengene score from the sample that is at or above a reference myeloid eigengene score (e.g., above or an increase in the myeloid eigengene score of about 10%, 20%, 30%, 40%, 50%, 60%, 70%, 80%, 90%, 95%, 96%, 97%, 98%, or 99% or greater) identifies the individual as one who may benefit from a treatment with a DMARD. In some instances, the methods and assays provided herein may further involve determining a lymphoid eigengene score from the sample from the individual, wherein a lymphoid eigengene score from the sample that is at or above a reference lymphoid eigengene score (e.g., above or an increase in the lymphoid eigengene score of about 10%, 20%, 30%, 40%, 50%, 60%, 70%, 80%, 90%, 95%, 96%, 97%, 98%, or 99% or greater) identifies the individual as one who may benefit from a treatment with a DMARD.

The present invention also provides methods and assays for selecting a therapy for an individual having RA, the method or assay including determining a myeloid eigengene score from a sample from the individual, wherein a myeloid eigengene score from the sample that is at or above a reference myeloid eigengene score (e.g., above or an increase in the myeloid eigengene score of about 10%, 20%, 30%, 40%, 50%, 60%, 70%, 80%, 90%, 95%, 96%, 97%, 98%, or 99% or greater) identifies the individual as one who may benefit from a treatment comprising a DMARD (e.g., methotrexate). In some instances a myeloid eigengene score that is above a reference myeloid eigengene score, or an elevated or increased myeloid eigengene score, refers to an overall increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference myeloid eigengene score. In some instances, an elevated myeloid eigengene score refers to an overall increase of the myeloid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference myeloid eigengene score. In some instances, the methods and assays may further involve determining a lymphoid eigengene score from the sample from the individual, wherein a lymphoid eigengene score from the sample that is at or above a reference lymphoid eigengene score (e.g., above or an increase in the lymphoid eigengene score of about 10%, 20%, 30%, 40%, 50%, 60%, 70%, 80%, 90%, 95%, 96%, 97%, 98%, or 99% or greater) identifies the individual as one who may benefit from a treatment comprising a DMARD. In some instances a lymphoid eigengene score that is above a reference lymphoid eigengene score or an elevated or increased lymphoid eigengene score, refers to an overall increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference lymphoid eigengene score. In some instances, an elevated lymphoid eigengene score refers to an overall increase of the lymphoid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference lymphoid eigengene score.

In any of the predictive methods and assays described above, the reference myeloid eigengene score may be a reference myeloid eigengene score in a reference population of individuals having RA who have been previously treated with a DMARD, the population of individuals consisting of a first subset of individuals who responded to the DMARD therapy and a second subset of individuals who did not respond to the DMARD therapy. In some instances, the reference myeloid eigengene score significantly separates each of the first and second subsets of individuals based on a significant difference in the myeloid eigengene score in the first subset of individuals compared to that of the second subset of individuals. In some instances, the first subset of individuals responded to the DMARD therapy and the second subset did not respond to the DMARD therapy after about six months following the initiation of the DMARD therapy.

In any of the predictive methods and assays described above, the reference lymphoid eigengene score may be a reference lymphoid eigengene score in a reference population of individuals having RA who have been previously treated with a DMARD, the population of individuals consisting of a first subset of individuals who responded to the DMARD therapy and a second subset of individuals who did not respond to the DMARD therapy. In some instances, the reference lymphoid eigengene score significantly separates each of the first and second subsets of individuals based on a significant difference in the lymphoid eigengene score in the first subset of individuals compared to that of the second subset of individuals. In some instances, the first subset of individuals responded to the DMARD therapy and the second subset did not respond to the DMARD therapy after about six months following the initiation of the DMARD therapy.

The present invention provides methods and assays that may be used to monitor the response of an individual having RA to treatment with a DMARD, the method or assay including (i) determining a myeloid eigengene score from a sample from the individual at a first time point during or after administration of a DMARD; (ii) determining a second myeloid eigengene score from a sample from the individual at a second time point; and (iii) comparing the first myeloid eigengene score with a the second myeloid eigengene score, wherein a decrease in the second myeloid eigengene score (e.g., a decrease in the myeloid eigengene score of about 10%, 20%, 30%, 40%, 50%, 60%, 70%, 80%, 90%, 95%, 96%, 97%, 98%, or 99% or greater) relative to the first myeloid eigengene score is predictive of an individual who is likely to respond to treatment with a DMARD. The methods and assays may further involve (i) determining a lymphoid eigengene score from a sample from the individual at a first time point during or after administration of a DMARD; (ii) determining a second lymphoid eigengene score from a sample from the individual at a second time point; and (iii) comparing the first lymphoid eigengene score with a the second lymphoid eigengene score, wherein a decrease in the second lymphoid eigengene score (e.g., a decrease in the lymphoid eigengene score of about 10%, 20%, 30%, 40%, 50%, 60%, 70%, 80%, 90%, 95%, 96%, 97%, 98%, or 99% or greater) relative to the first lymphoid eigengene score is further predictive of an individual who is likely to respond to treatment with a DMARD. In some instances, a reduced or decreased myeloid eigengene score, refers to an overall decrease of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference myeloid eigengene score. In some instances, a reduced myeloid eigengene score refers to an overall decrease of the myeloid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference myeloid eigengene score. In some instances, a reduced or decreased lymphoid eigengene score, refers to an overall decrease of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference lymphoid eigengene score. In some instances, a reduced lymphoid eigengene score refers to an overall decrease of the lymphoid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference lymphoid eigengene score.

In some instances, the second myeloid eigengene score is decreased relative to the first myeloid eigengene score, and the method or assay further involves administering and additional dose of a DMARD to the individual. In some instances, the second lymphoid eigengene score is decreased relative to the first lymphoid eigengene score, and the method or assay further involves administering and additional dose of a DMARD to the individual.

In some instances, the second myeloid eigengene score is decreased relative to the first myeloid eigengene score, the second lymphoid eigengene score is decreased relative to the first lymphoid eigengene score, and the method or assay further involves administering and additional dose of a DMARD to the individual.

In some instances of any of the preceding methods or assays involving determining a myeloid eigengene score and/or lymphoid eigengene score, the individual has been previously treated with a DMARD. In other instances, the individual has not been previously treated with a DMARD.

iii. Exemplary Approaches for Determination of Biomarker Expression Levels

The methods and assays provided herein may include determining an expression level of one or more genes in a sample (e.g., a synovial tissue sample, a synovial fluid sample, or a combination thereof) from an individual. The sample from the individual may be an archival sample, a fresh sample, or a frozen sample. The expression level of the one or more genes can be determined qualitatively and/or quantitatively based on any suitable criterion known in the art, including, but not limited to, the measurement of DNA, mRNA, cDNA, proteins, protein fragments, and/or gene copy number levels in an individual. Methodologies for measuring such biomarkers are known in the art and understood by the skilled artisan, including, but not limited to, whole genome sequencing, polymerase chain reaction (PCR) including quantitative real time PCR (qRT-PCR) and other amplification type detection methods, such as, for example, branched DNA, SISBA, TMA and the like, RNASeq, microarray analysis, gene expression profiling, whole-genome sequencing (WGS), and/or serial analysis of gene expression ("SAGE"), direct digital counting of nucleic acids (e.g., Nanostring nCounter), immunohistochemistry ("IHC"), Western blot analysis, immunoprecipitation, molecular binding assays, ELISA, ELIFA, fluorescence activated cell sorting ("FACS"), MassARRAY, proteomics, biochemical enzymatic activity assays, in situ hybridization (ISH), fluorescence in situ hybridization (FISH), Southern analysis, Northern analysis, as well as any one of the wide variety of assays that can be performed by protein, gene, and/or tissue array analysis. Typical protocols for evaluating the status of genes and gene products are found, for example, in Ausubel et al. eds. (Current Protocols In Molecular Biology, 1995), Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

In some instances of any of the preceding methods and assays, the expression level of a biomarker may be a nucleic acid expression level (e.g., a DNA expression level or an RNA expression level (e.g., an mRNA expression level)). Any suitable method of determining a nucleic acid expression level may be used. In some instances, the nucleic acid expression level is determined using direct digital counting of nucleic acids (e.g., Nanostring nCounter), RNAseq, RT-qPCR, qPCR, multiplex qPCR or RT-qPCR, microarray analysis, SAGE, MassARRAY technique, ISH, or a combination thereof.

Methods for the evaluation of mRNAs in cells are well known and include, for example, serial analysis of gene expression (SAGE), whole genome sequencing (WGS), hybridization assays using complementary DNA probes (such as in situ hybridization using labeled riboprobes specific for the one or more genes, Northern blot and related techniques) and various nucleic acid amplification assays (such as RT-PCR (e.g., qRT-PCR) using complementary primers specific for one or more of the genes, and other amplification type detection methods, such as, for example, branched DNA, SISBA, TMA and the like). In addition, such methods can include one or more steps that allow one to determine the levels of target mRNA in a biological sample (e.g., by simultaneously examining the levels a comparative control mRNA sequence of a "housekeeping" gene such as an actin family member). Optionally, the sequence of the amplified target cDNA can be determined. Optional methods include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes whose expression correlates with increased or reduced clinical benefit of treatment comprising an immunotherapy and a suppressive stromal antagonist may be arrayed on a solid support. Hybridization of a labeled probe with a particular array member indicates that the sample from which the probe was derived expresses that gene.

In other instances of any of the preceding methods, the expression level of a biomarker may be a protein expression level. In certain instances, the method comprises contacting the sample with antibodies that specifically bind to a biomarker described herein under conditions permissive for binding of the biomarker, and detecting whether a complex is formed between the antibodies and biomarker.

Any method of measuring protein expression levels known in the art or provided herein may be used. For example, in some instances, a protein expression level of a biomarker is determined using a method selected from, but not limited to western blot, enzyme-linked immunosorbent assay (ELISA), immunoprecipitation, immunohistochemistry (IHC), flow cytometry (e.g., fluorescence-activated cell sorting (FACS™)), immunofluorescence, radioimmunoassay, dot blotting, immunodetection methods, HPLC, surface plasmon resonance, optical spectroscopy, mass spectrometry, liquid chromatography-mass spectrometry (LC-MS), nephelometry, aptamer technology, and HPLC.

In certain instances, the presence and/or expression level/amount of a biomarker protein in a sample is examined using IHC and staining protocols. IHC staining of tissue sections has been shown to be a reliable method of determining or detecting the presence of proteins in a sample. In some instances of any of the methods, assays and/or kits, the biomarker is one or more of the protein expression products of the genes set forth in Table 1. In one instance, an expression level of biomarker is determined using a method comprising: (a) performing IHC analysis of a sample (such as a synovial tissue sample obtained from an individual) with an antibody; and (b) determining expression level of a biomarker in the sample. In some instances, IHC staining intensity is determined relative to a reference. In some instances, the reference is a reference value. In some instances, the reference is a reference sample (e.g., a control cell line staining sample, a tissue sample from non-RA affected individual, or a synovial tissue sample that is determined to be negative for the biomarker of interest).

IHC may be performed in combination with additional techniques such as morphological staining and/or in situ hybridization (e.g., ISH). Two general methods of IHC are available; direct and indirect assays. According to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for IHC typically will be labeled with a detectable moiety. Numerous labels are available which can be generally grouped into the following categories: (a) radioisotopes, such as $^{35}S$, $^{14}C$, $^{125}I$, $^{3}H$, and $^{131}I$; (b) colloidal gold particles; (c) fluorescent labels including, but are not limited to, rare earth chelates (europium chelates), Texas Red, rhodamine, fluorescein, dansyl, lissamine, umbelliferone, phycocrytherin, phycocyanin, or commercially-available fluorophores such as SPECTRUM ORANGE7 and SPECTRUM GREEN7 and/or derivatives of any one or more of the above; (d) various enzyme-substrate labels are available and U.S. Pat. No. 4,275,149 provides a review of some of these. Examples of enzymatic labels include luciferases (e.g., firefly luciferase and bacterial luciferase; see, e.g., U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Examples of enzyme-substrate combinations include, for example, horseradish peroxidase (HRPO) with hydrogen peroxidase as a substrate; alkaline phosphatase (AP) with para-Nitrophenyl phosphate as chromogenic substrate; and β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase). For a general review of these, see, for example, U.S. Pat. Nos. 4,275,149 and 4,318,980.

Specimens may be prepared, for example, manually, or using an automated staining instrument (e.g., a Ventana BenchMark XT or Benchmark ULTRA instrument). Specimens thus prepared may be mounted and coverslipped. Slide evaluation is then determined, for example, using a microscope, and staining intensity criteria, routinely used in the art, may be employed. In some instances, the presence of a biomarker is detected by IHC in >0% of the sample, in at least 1% of the sample, in at least 5% of the sample, in at least 10% of the sample, in at least 15% of the sample, in at least 15% of the sample, in at least 20% of the sample, in at least 25% of the sample, in at least 30% of the sample, in at least 35% of the sample, in at least 40% of the sample, in at least 45% of the sample, in at least 50% of the sample, in at least 55% of the sample, in at least 60% of the sample, in at least 65% of the sample, in at least 70% of the sample, in at least 75% of the sample, in at least 80% of the sample, in at least 85% of the sample, in at least 90% of the sample, in at least 95% of the sample, or more. Samples may be scored using any method known in the art, for example, by a pathologist or automated image analysis.

In some instances of any of the methods and assays, the biomarker is detected by immunohistochemistry using a diagnostic antibody (e.g., a primary diagnostic antibody). In some instances, the diagnostic antibody specifically binds human antigen. In some instances, the diagnostic antibody is a non-human antibody. In some instances, the diagnostic antibody is a rat, mouse, or rabbit antibody. In some instances, the diagnostic antibody is a rabbit antibody. In some instances, the diagnostic antibody is a monoclonal antibody. In some instances, the diagnostic antibody is directly labeled. In other instances, the diagnostic antibody is indirectly labeled (e.g., by a secondary antibody).

In some instances of any of the preceding methods and assays the sample is obtained from the individual prior to (e.g., minutes, hours, days, weeks (e.g., 1, 2, 3, 4, 5, 6, or 7 weeks), months, or years prior to) administration of an RA therapy. In some instances of any of the preceding methods, the sample from the individual is obtained about 2 to about 10 weeks (e.g., 2, 3, 4, 5, 6, 7, 8, 9, or 10 weeks) following administration of an RA therapy. In some instances, the sample from the individual is obtained about 4 to about 6 weeks following administration of an RA therapy.

In some instances of any of the preceding methods and assays, the expression level or number of a biomarker is detected in a synovial tissue sample, a synovial fluid sample, a primary or cultured cells or cell line, a cell supernatant, a cell lysate, platelets, serum, plasma, vitreous fluid, lymph fluid, follicular fluid, seminal fluid, amniotic fluid, milk, whole blood, blood-derived cells, urine, cerebro-spinal fluid, saliva, sputum, tears, perspiration, mucus, tissue culture medium, tissue extracts such as homogenized tissue, cellular extracts, or any combination thereof. In some instances, the sample is a tissue sample (e.g., a synovial tissue sample), a cell sample, a whole blood sample, a plasma sample, a serum sample, or a combination thereof. In some instances, the sample is a synovial tissue sample wherein, the synovial tissue sample includes resident cells, synovium-infiltrating immune cells, or a combination thereof. In some instances, the synovial tissue sample is a formalin-fixed and paraffin-embedded (FFPE) sample, an archival sample, a fresh sample, or a frozen sample.

For example, in some instances for any of the preceding methods and assays, the expression level of a biomarker in a sample (e.g., a synovial tissue sample) is detected in synovium-infiltrating immune cells, synovial cells, PBMCs, or combinations thereof using known techniques (e.g., flow cytometry or IHC). Synovium-infiltrating immune cells include, but are not limited to T lymphocytes, B lymphocytes (including plasma cells), or other bone marrow-lineage cells including granulocytes (e.g., mast cells), monocytes, macrophages, dendritic cells, and natural killer (NK) cells. In some instances, the staining for a biomarker is detected as membrane staining, cytoplasmic staining, or combinations thereof. In other instances, the absence of a biomarker is detected as absent or no staining in the sample, relative to a reference sample.

In certain instances, a reference sample, reference cell, reference tissue, control sample, control cell, or control tissue is a single sample or combined multiple samples from the same patient or individual that are obtained at one or more different time points than when the test sample is obtained. For example, a reference sample, reference cell, reference tissue, control sample, control cell, or control tissue is obtained at an earlier time point from the same patient or individual than when the test sample is obtained. Such reference sample, reference cell, reference tissue, control sample, control cell, or control tissue may be useful if the reference sample is obtained during initial diagnosis of RA and the test sample is later obtained when the disease has progressed.

In certain instances, a reference sample, reference cell, reference tissue, control sample, control cell, or control tissue is a combined multiple samples from one or more healthy individuals who are not the patient. In certain instances, a reference sample, reference cell, reference tissue, control sample, control cell, or control tissue is a combined multiple samples from one or more individuals with a disease or disorder (e.g., RA) who are not the patient or individual. In certain instances, a reference sample, reference cell, reference tissue, control sample, control cell, or control tissue is pooled RNA samples from normal tissues or pooled plasma or serum samples from one or more individuals who are not the patient. In certain instances, a reference sample, reference cell, reference tissue, control sample, control cell, or control tissue is pooled RNA samples from synovial tissues, synovial fluids, or pooled plasma or serum samples from one or more individuals with a disease or disorder (e.g., RA) who are not the patient.

B. Therapeutic Methods

The present invention also provides methods for treating an individual having RA. Accordingly, in some instances, the methods of the invention include administering to the individual an RA therapeutic agent. Any of the RA therapeutic agents described herein, or known in the art may be used in connection with the methods.

Provided herein is a method of treating an individual having RA that includes (i) determining the expression level of one or more of the genes set forth in Table 1 (e.g., 1, 2, 3, 4, 5, 6, 7, 8, 9, 10, 11, 12, 13, 14, 15, 16, 17, 18, 19, 20, 21, 21, 22, 23, 24, 25, 26, 27, 28, 29, 30, 31, 32, 33, 34, 35, 36, 37, 38, 39, 40, 41, 42, 43, 44, 45, or 46 genes set forth in Table 1) in a sample from the individual, wherein the expression level of the one or more of the genes set forth in Table 1 is determined to be changed relative to a reference expression level, and (ii) administering an effective amount of an RA therapy (e.g., a therapeutic agent other than, or in addition to, a DMARD) to the individual based on the expression level of the one or more genes determined in step (i). In some instances, the change is an increase. In other instances, the change is a decrease.

Provided herein is a method of treating an individual having RA that includes (i) determining the expression level of one or more of the genes set forth in Table 2 (e.g., 1, 2, 3, 4, 5, 6, 7, 8, 9, 10, 11, 12, 13, 14, 15, 16, 17, 18, 19, 20, 21, 21, 22, 23, 24, 25, 26, 27, 28, 29, 30, 31, 32, 33, 34, 35, 36, 37, 38, 39, or 40 genes set forth in Table 2) in a sample from the individual, wherein the expression level of the one or more of the genes set forth in Table 2 is determined to be increased (e.g., an increased expression level of about 10%, 20%, 30%, 40%, 50%, 60%, 70%, 80%, 90%, 95%, 96%, 97%, 98%, or 99% or greater) relative to a reference expression level, and (ii) administering an effective amount of an RA therapy (e.g., a therapeutic agent other than, or in addition to, a DMARD) to the individual based on the expression level of the one or more genes determined in step (i). In certain instances, the increased expression level of one or more genes set forth in Table 2 (e.g., 1, 2, 3, 4, 5, 6, 7, 8, 9, 10, 11, 12, 13, 14, 15, 16, 17, 18, 19, 20, 21, 21, 22, 23, 24, 25, 26, 27, 28, 29, 30, 31, 32, 33, 34, 35, 36, 37, 38, 39, or 40 genes set forth in Table 2) is an increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference expression level of the one or more genes. In some instances, the increased expression level of the one or more genes set forth in Table 2 (e.g., 1, 2, 3, 4, 5, 6, 7, 8, 9, 10, 11, 12, 13, 14, 15, 16, 17, 18, 19, 20, 21, 21, 22, 23, 24, 25, 26, 27, 28, 29, 30, 31, 32, 33, 34, 35, 36, 37, 38, 39, or 40 genes set forth in Table 2) is an increase of at least about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, or about 1,000-fold or greater relative to a reference expression level of the one or more genes.

Provided herein is a method of treating an individual having RA that includes (i) determining the expression level of one or more of the genes set forth in Table 3 (e.g., 1, 2, 3, 4, 5, or 6 genes set forth in Table 3) in a sample from the individual, wherein the expression level of the one or more of the genes set forth in Table 3 is determined to be decreased (e.g., a decreased expression level of about 10%, 20%, 30%, 40%, 50%, 60%, 70%, 80%, 90%, 95%, 96%, 97%, 98%, or 99% or greater) relative to a reference expression level, and (ii) administering an effective amount of an RA therapy (e.g., a therapeutic agent other than, or in addition to, a DMARD) to the individual based on the expression level of the one or more genes determined in step (i). In certain instances, the decreased expression level of the one or more genes set forth in Table 3 (e.g., 1, 2, 3, 4, 5, or 6 genes set forth in Table 3) is a decrease of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference expression level of the one or more genes. In some instances, the decreased expression level of the one or more genes set forth in Table 3 (e.g., 1, 2, 3, 4, 5, or 6 genes set forth in Table 3) is a decrease of at least about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, or about 1,000-fold or greater relative to a reference expression level of the one or more genes.

Also provided is a method of treating an individual having RA that includes administering an effective amount of an RA therapy (e.g., a therapeutic agent other than, or in addition to, a DMARD) to the individual, wherein the individual has been identified as one who is more likely to exhibit disease progression by one or more of the predictive diagnostic methods described in Section II-A, above.

The invention also provides a method of treating an individual having RA that includes (i) obtaining a sample from the individual, (ii) performing a gene expression assay on the sample and detecting (a) an increased expression level (e.g., an increased expression level of about 10%, 20%, 30%, 40%, 50%, 60%, 70%, 80%, 90%, 95%, 96%, 97%, 98%, or 99% or greater) of one or more genes set forth in Table 2 (e.g., 1, 2, 3, 4, 5, 6, 7, 8, 9, 10, 11, 12, 13, 14, 15, 16, 17, 18, 19, 20, 21, 21, 22, 23, 24, 25, 26, 27, 28, 29, 30, 31, 32, 33, 34, 35, 36, 37, 38, 39, or 40 genes set forth in Table 2) in the sample and/or (b) a decreased level (e.g., a decreased expression level of about 10%, 20%, 30%, 40%, 50%, 60%, 70%, 80%, 90%, 95%, 96%, 97%, 98%, or 99% or greater) of one or more genes set forth in Table 3 (e.g., 1, 2, 3, 4, 5, or 6 genes set forth in Table 3) in the sample relative to a reference expression level, (iii) identifying the individual as having an increased likelihood of benefitting from a therapeutic agent other than, or in addition to, a DMARD, and (iv) administering to the individual a therapeutic agent other than, or in addition to, a DMARD. In some instances, the increased expression level of the one or more genes set forth in Table 2 (e.g., 1, 2, 3, 4, 5, 6, 7, 8, 9, 10, 11, 12, 13, 14, 15, 16, 17, 18, 19, 20, 21, 21, 22, 23, 24, 25, 26, 27, 28, 29, 30, 31, 32, 33, 34, 35, 36, 37, 38, 39, or 40 genes set forth in Table 2) is an increase of at least about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, or about 1,000-fold or greater relative to a reference expression level of the one or more genes. In certain instances, the decreased expression level of the one or more genes set forth in Table 3 (e.g., 1, 2, 3, 4, 5, or 6 genes set forth in Table 3) is a decrease of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference expression level of the one or more genes. In some instances, the decreased expression level of the one or more genes set forth in Table 3 (e.g., 1, 2, 3, 4, 5, or 6 genes set forth in Table 3) is a decrease of at least about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, or about 1,000-fold or greater relative to a reference expression level of the one or more genes.

The invention also provides a method of treating RA in an individual identified as having an increased expression level (e.g., an increased expression level of about 10%, 20%, 30%, 40%, 50%, 60%, 70%, 80%, 90%, 95%, 96%, 97%, 98%, or 99% or greater) of one or more genes set forth in Table 2 (e.g., 1, 2, 3, 4, 5, 6, 7, 8, 9, 10, 11, 12, 13, 14, 15, 16, 17, 18, 19, 20, 21, 21, 22, 23, 24, 25, 26, 27, 28, 29, 30, 31, 32, 33, 34, 35, 36, 37, 38, 39, or 40 genes set forth in Table 2) relative to a reference expression level of the one or more genes, wherein the method includes administering an effective amount of an RA therapy (e.g., a therapeutic agent other than, or in addition to, a DMARD) to the individual. In certain instances, the increased expression level of the one or more genes set forth in Table 2 (e.g., 1, 2, 3, 4, 5, 6, 7, 8, 9, 10, 11, 12, 13, 14, 15, 16, 17, 18, 19, 20, 21, 21, 22, 23, 24, 25, 26, 27, 28, 29, 30, 31, 32, 33, 34, 35, 36, 37, 38, 39, or 40 genes set forth in Table 2) is an increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference expression level of the one or more genes, and the method includes administering an effective amount of an RA therapy (e.g., a therapeutic agent other than, or in addition to, a DMARD) to the individual. In some instances, the increased expression level of the one or more genes set forth in Table 2 (e.g., 1, 2, 3, 4, 5, 6, 7, 8, 9, 10, 11, 12, 13, 14, 15, 16, 17, 18, 19, 20, 21, 21, 22, 23, 24, 25, 26, 27, 28, 29, 30, 31, 32, 33, 34, 35, 36, 37, 38, 39, or 40 genes set forth in Table 2) is an increase of at least about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, or about 1,000-fold or greater relative to a reference expression level of the one or more genes, and the method includes administering an effective amount of an RA therapy (e.g., a therapeutic agent other than, or in addition to, a DMARD) to the individual.

In another instance, the invention provides a method of treating RA in an individual having been identified as having an expression level in a sample from the individual of one or more genes selected from CD180, CSF2, CXCL1, DENND1C, MMP10, SDC1, and UBASH3A (e.g., 1, 2, 3, 4, 5, 6, or 7 genes selected from CD180, CSF2, CXCL1, DENND1C, MMP10, SDC1, and UBASH3A) that is at or above a reference expression level of the one or more genes (e.g., above or an increase in the expression level of about 10%, 20%, 30%, 40%, 50%, 60%, 70%, 80%, 90%, 95%, 96%, 97%, 98%, or 99% or greater), the method including administering to the individual an RA therapy (e.g., a therapeutic agent other than, or in addition to, a DMARD). In certain instances, the increased expression level of one or more genes selected from CD180, CSF2, CXCL1, DENND1C, MMP10, SDC1, and UBASH3A (e.g., 1, 2, 3, 4, 5, 6, or 7 genes selected from CD180, CSF2, CXCL1, DENND1C, MMP10, SDC1, and UBASH3A) is an increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference expression level of the one or more genes. In some instances, the increased expression level of one or more genes selected from CD180, CSF2, CXCL1, DENND1C, MMP10, SDC1, and UBASH3A (e.g., 1, 2, 3, 4, 5, 6, or 7 genes selected from CD180, CSF2, CXCL1, DENND1C, MMP10, SDC1, and UBASH3A) is an increase of at least about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, or about 1,000-fold or greater relative to a reference expression level of the one or more genes.

In another instance, the invention provides a method of treating RA in an individual having been identified as having an expression level in a sample from the individual of at least two, at least three, at least four, at least five, at least six, or all seven of the following genes in a sample from the individual: CD180, CSF2, CXCL1, DENND1C, MMP10, SDC1, and UBASH3A, that is at or above a reference expression level (e.g., above or an increase in the expression level of about 10%, 20%, 30%, 40%, 50%, 60%, 70%, 80%, 90%, 95%, 96%, 97%, 98%, or 99% or greater) of the at least two, at least three, at least four, at least five, at least six, or all seven genes, the method including administering to the individual an RA therapy (e.g., a therapeutic agent other than, or in addition to, a DMARD). In certain instances, the increased expression level of at least two, at least three, at least four, at least five, at least six, or all seven genes selected from CD180, CSF2, CXCL1, DENND1C, MMP10, SDC1, and UBASH3A is an increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference expression level of at least two, at least three, at least four, at least five, at least six, or all seven genes. In some instances, the increased expression level of at least two, at least three, at least four, at least five, at least six, or all seven genes selected from CD180, CSF2, CXCL1, DENND1C, MMP10, SDC1, and UBASH3A is an increase of at least about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, or about 1,000-fold or greater relative to a reference expression level of the at least two, at least three, at least four, at least five, at least six, or all seven genes.

In another instance, the invention provides a method of treating RA in an individual having been identified as having an expression level in a sample from the individual of one or more genes set forth in Table 3 (e.g., 1, 2, 3, 4, 5, or 6) that is at or below a reference expression level (e.g., below or a decrease in the expression level of about 10%, 20%, 30%, 40%, 50%, 60%, 70%, 80%, 90%, 95%, 96%, 97%, 98%, or 99% or greater) of the one or more genes, the method including administering to the individual an RA therapy (e.g., a therapeutic agent other than, or in addition to, a DMARD). In certain instances, the decreased expression level of one or more genes set forth in Table 3 (e.g., 1, 2, 3, 4, 5, or 6 genes set forth in Table 3) is a decrease of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference expression level of the one or more genes. In some instances, the decreased expression level of one or more genes set forth in Table 3 (e.g., 1, 2, 3, 4, 5, or 6 genes set forth in Table 3) is a decrease of at least about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, or about 1,000-fold or greater relative to a reference expression level of the one or more genes.

In any of the therapeutic methods described above, the methods may further include determining one or more clinical covariates (e.g., baseline RF titer, disease duration, DAS28-ESR, DAS28-CRP, baseline pathotype, and 12 max USST and USPD scores) of the individual.

In any of the therapeutic methods described above, the reference expression level may be a reference expression level in a reference population of individuals having RA who have not been previously treated with a DMARD, the population of individuals consisting of a first subset of individuals who exhibited disease progression and a second subset of individuals who did not exhibit disease progression. In some instances, the reference expression level significantly separates each of the first and second subsets of individuals based on a significant difference in the expression level of the one or more genes set forth in Table 1, Table 2, or Table 3 in the first subset of individuals compared to that of the second subset of individuals. In some instances, the first subset of individuals exhibited disease progression and the second subset of individuals did not exhibit disease progression after about 12 months.

In any of the therapeutic methods described above in which the expression level of more than one biomarker selected from the genes set forth in Table 1, Table 2, or Table 3 is determined in a sample from an individual and compared to a reference expression level (e.g. a pre-assigned expression level of the one or more genes set forth in Table 1, Table 2, or Table 3), it is to be understood that, in some instances, the expression level of each individual biomarker in the sample is compared to a reference expression level for each individual biomarker. For example, if the expression level of CD180 and CXCL1 are determined in a sample from an individual and compared to reference expression levels for CD180 and CXCL1, in some instances, the expression level of CD180 in the sample from the individual is compared to the reference expression level for CD180, and the expression level of CXCL1 in the sample from the individual is compared to the reference expression level for CXCL1. In other instances, an expression level for more than one gene of interest may be determined by aggregation methods known to one skilled in the art and also disclosed herein, including, for example, by calculating the median or mean of all the expression levels of the genes of interest. Before aggregation, the expression level of each gene of interest may be normalized by using statistical methods known to one skilled in the art and also disclosed herein, including, for example, normalized to the expression level of one or more housekeeping genes, or normalized to a total library size, or normalized to the median or mean expression level value across all genes measured. In some instances, before aggregation across multiple genes of interest, the normalized expression level of each gene of interest may be standardized by using statistical methods known to one skilled in the art and also disclosed herein, including, for example, by calculating the Z-score of the normalized expression level of each gene of interest.

In any of the therapeutic methods described above in which the expression level of one or more biomarkers, selected from the biomarkers set forth in Table 1, Table 2, or Table 3, is determined in a sample from an individual and compared to a reference expression level (e.g., a pre-assigned expression level of the one or more genes set forth in Table 1, Table 2, or Table 3), it is to be understood that, in some instances, the expression level of one or more genes may be an average of the expression level of the one or more genes. In some instances, the expression level of the one or more genes may be a median of the expression level of the one or more genes. In some instances, the expression level the one or more genes may be normalized, e.g., to a reference gene, e.g., a housekeeping gene. In some instances, the reference gene is ACTB, GAPDH, GUSB, HPRT1, PGK1, RPL19, TUBB, or TMEM55B. In some instances, the expression level of the one or more genes may be an average of a normalized expression level of the one or more genes. In some instances, the expression level of the one or more genes may be a median of a normalized expression level of the one or more genes.

The present invention provides methods that may be used to treat an individual having RA with an RA therapy (e.g., RA therapy that includes a DMARD, such as methotrexate) that involves (i) obtaining a sample form the individual, (ii) performing a gene expression assay on the sample and determining a myeloid eigengene score equal to or increased relative to a reference myeloid eigengene score (e.g., an increased myeloid eigengene score of about 10%, 20%, 30%, 40%, 50%, 60%, 70%, 80%, 90%, 95%, 96%, 97%, 98%, or 99% or greater), (iii) identifying the individual as having an increased likelihood of benefitting from an RA therapy (e.g., RA therapy that includes a DMARD, such as methotrexate), and (iv) administering to the individual an RA therapy (e.g., RA therapy that includes a DMARD, such as methotrexate). In some instances, an increased myeloid eigengene score, refers to an overall increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference myeloid eigengene score. In some instances, an increased myeloid eigengene score refers to an overall increase of the myeloid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference myeloid eigengene score. In some instances, the methods may further include, prior to the identifying the individual as having an increased likelihood of benefitting from an RA therapy (e.g., RA therapy that includes a DMARD, such as methotrexate), performing a gene expression assay on the sample and determining a lymphoid eigengene score equal to or increased relative to a reference lymphoid eigengene score (e.g., an increased lymphoid eigengene score of about 10%, 20%, 30%, 40%, 50%, 60%, 70%, 80%, 90%, 95%, 96%, 97%, 98%, or 99% or greater). In some instances, an increased lymphoid eigengene score, refers to an overall increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference lymphoid eigengene score. In some instances, an increased lymphoid eigengene score refers to an overall increase of the lymphoid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference lymphoid eigengene score.

The present invention provides methods that may be used to treat an individual having RA with an RA therapy (e.g., RA therapy that includes a DMARD, such as methotrexate) that involves (i) determining the myeloid eigengene score from a sample from the individual, wherein a myeloid eigengene score from the sample is determined to be at or above a reference myeloid eigengene score (e.g., above or an increase in the myeloid eigengene score of about 10%, 20%, 30%, 40%, 50%, 60%, 70%, 80%, 90%, 95%, 96%, 97%, 98%, or 99% or greater), and (ii) administering an effective amount of an RA therapy (e.g., RA therapy that includes a DMARD, such as methotrexate) to the individual based on the myeloid eigengene score of step (i). In some instances, an elevated or increased myeloid eigengene score, refers to an overall increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference myeloid eigengene score. In some instances, an elevated myeloid eigengene score refers to an overall increase of the myeloid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference myeloid eigengene score. In some instances, the methods may further involve, prior to the administering of an RA therapy (e.g., RA therapy that includes a DMARD, such as methotrexate), determining a lymphoid eigengene score from the sample from the individual, wherein a lymphoid eigengene score from the sample is determined to be at or above a reference lymphoid eigengene score (e.g., above or an increase in the lymphoid eigengene score of about 10%, 20%, 30%, 40%, 50%, 60%, 70%, 80%, 90%, 95%, 96%, 97%, 98%, or 99% or greater). In some instances, an elevated or increased lymphoid eigengene score, refers to an overall increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference lymphoid eigengene score. In some instances, an elevated lymphoid eigengene score refers to an overall increase of the lymphoid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference lymphoid eigengene score.

Also provided is a method of treating an individual having RA that includes administering an effective amount of an RA therapy (e.g., RA therapy that includes a DMARD, such as methotrexate) to the individual, wherein the individual has been identified as one who is more likely to benefit from an RA therapy (e.g., RA therapy that includes a DMARD, such as methotrexate) by one or more of the predictive diagnostic methods described in Section II-A, above. Accordingly, in some instances, the individual has been identified as one who is more likely to benefit from an RA treatment (e.g., RA therapy that includes a DMARD, such as methotrexate) based on a myeloid eigengene score from a sample from the individual that has been determined to be at or above a reference myeloid eigengene score (e.g., above or an increase in the myeloid eigengene score of about 10%, 20%, 30%, 40%, 50%, 60%, 70%, 80%, 90%, 95%, 96%, 97%, 98%, or 99% or greater). In some instances, an elevated or increased myeloid eigengene score, refers to an overall increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference myeloid eigengene score. In some instances, an elevated myeloid eigengene score refers to an overall increase of the myeloid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference myeloid eigengene score. In some instances, prior to administering an RA therapy (e.g., RA therapy that includes a DMARD, such as methotrexate) to the individual, the individual has been identified as one who is more likely to benefit from an RA therapy (e.g., RA therapy that includes a DMARD, such as methotrexate) based further on a lymphoid eigengene score from a sample from the individual that has been determined to be at or above a reference lymphoid eigengene score (e.g., above or an increase in the lymphoid eigengene score of about 10%, 20%, 30%, 40%, 50%, 60%, 70%, 80%, 90%, 95%, 96%, 97%, 98%, or 99% or greater). In some instances, an elevated or increased lymphoid eigengene score, refers to an overall increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference lymphoid eigengene score. In some instances, an elevated lymphoid eigengene score refers to an overall increase of the lymphoid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference lymphoid eigengene score.

Also provided is a method of treating an individual having RA that includes administering an effective amount of an RA therapy (e.g., RA therapy that includes a DMARD, such as methotrexate) to the individual, wherein the individual has been identified as having a myeloid eigengene score from a sample from the individual that is at or above a reference myeloid eigengene score by one or more of the predictive diagnostic methods described in Section II-A, above. Accordingly, in some instances, the individual has been identified as having a myeloid eigengene score from a sample from the individual that is at or above a reference myeloid eigengene score (e.g., above or an increase in the myeloid eigengene score of about 10%, 20%, 30%, 40%, 50%, 60%, 70%, 80%, 90%, 95%, 96%, 97%, 98%, or 99% or greater). In some instances, an elevated or increased myeloid eigengene score, refers to an overall increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference myeloid eigengene score. In some instances, an elevated myeloid eigengene score refers to an overall increase of the myeloid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference myeloid eigengene score. In some instances, prior to administering an RA therapy (e.g., RA therapy that includes a DMARD, such as methotrexate) to the individual, the individual has been identified as having a lymphoid eigengene score from a sample from the individual that is at or above a reference lymphoid eigengene score (e.g., above or an increase in the lymphoid eigengene score of about 10%, 20%, 30%, 40%, 50%, 60%, 70%, 80%, 90%, 95%, 96%, 97%, 98%, or 99% or greater). In some instances, an elevated or increased lymphoid eigengene score, refers to an overall increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference lymphoid eigengene score. In some instances, an elevated lymphoid eigengene score refers to an overall increase of the lymphoid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference lymphoid eigengene score.

In particular instances, the methods provided herein may be used to optimize therapeutic efficacy of an RA therapy (e.g., RA therapy that includes a DMARD, such as methotrexate), the method including monitoring a myeloid eigengene score from a sample from the individual during treatment (e.g., over a treatment period) with the RA therapy. Monitoring may include, for example, obtaining and comparing myeloid eigengene scores from samples from the individual collected at time intervals before and/or after administration of the RA therapy (e.g., RA therapy that includes a DMARD, such as methotrexate). In some instances, a myeloid eigengene score may be obtained from a sample from the individual that was collected at least about 1, 2, 3, 4, 5, 6, 7, 8, 9, 10, 11, 12, 13, 14, 15, 16, 17, 18, 19, 20, 21, 22, 23, or 24 hours; about 1, 2, 3, 4, 5, 6, 7 days; about 1, 2, 3, or 4 weeks; or about 1, 2, 3, 4, 5, 6, 7, 8, 9, 10, 11, or 12 months before administration of an RA therapy (e.g., RA therapy that includes a DMARD, such as methotrexate). In some instances, a myeloid eigengene score may be obtained from a sample from the individual that was collected at least about 1, 2, 3, 4, 5, 6, 7, 8, 9, 10, 11, 12, 13, 14, 15, 16, 17, 18, 19, 20, 21, 22, 23, or 24 hours; about 1, 2, 3, 4, 5, 6, 7 days; about 1, 2, 3, or 4 weeks; or about 1, 2, 3, 4, 5, 6, 7, 8, 9, 10, 11, or 12 months after administration of an RA therapy (e.g., RA therapy that includes a DMARD, such as methotrexate). The myeloid eigengene scores from samples from the individual collected before and/or after the administration of the RA therapy (e.g., RA therapy that includes a DMARD, such as methotrexate) may be compared, wherein an increase in a myeloid eigengene score (e.g., an increase in the myeloid eigengene score of about 10%, 20%, 30%, 40%, 50%, 60%, 70%, 80%, 90%, 95%, 96%, 97%, 98%, or 99% or greater) from a sample from the individual collected after treatment relative to a myeloid eigengene score from a sample collected before treatment may indicate a low level of therapeutic efficacy of the RA therapy that was administered, and wherein a decrease in a myeloid eigengene score (e.g., a decrease in the myeloid eigengene score of about 10%, 20%, 30%, 40%, 50%, 60%, 70%, 80%, 90%, 95%, 96%, 97%, 98%, or 99% or greater) from a sample from the individual collected after treatment relative to a myeloid eigengene score from a sample collected before treatment may indicate therapeutic efficacy of the RA therapy (e.g., RA therapy that includes a DMARD, such as methotrexate) that was administered. In some instances, an elevated or increased myeloid eigengene score, refers to an overall increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference myeloid eigengene score. In some instances, an elevated myeloid eigengene score refers to an overall increase of the myeloid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference myeloid eigengene score. In some instances, a reduced or decreased myeloid eigengene score, refers to an overall decrease of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference myeloid eigengene score. In some instances, a reduced myeloid eigengene score refers to an overall decrease of the myeloid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference myeloid eigengene score.

In some instances, the reference myeloid eigengene score may be obtained from the individual prior to treatment with an RA therapy (e.g., RA therapy that includes a DMARD, such as methotrexate). In some instances, the method includes monitoring the myeloid eigengene score from a sample from the individual relative to a pre-treatment myeloid eigengene score during treatment (e.g., over a treatment period) with the RA therapy (e.g., RA therapy that includes a DMARD, such as methotrexate).

In particular instances, the methods provided herein may further include monitoring a lymphoid eigengene score from a sample from the individual during treatment (e.g., over a treatment period) with the RA therapy (e.g., RA therapy that includes a DMARD, such as methotrexate). Monitoring may include, for example, obtaining and comparing lymphoid eigengene scores from samples from the individual collected at time intervals before and/or after administration of the RA therapy (e.g., RA therapy that includes a DMARD, such as methotrexate). In some instances, a lymphoid eigengene score may be obtained from a sample from the individual that was collected at least about 1, 2, 3, 4, 5, 6, 7, 8, 9, 10, 11, 12, 13, 14, 15, 16, 17, 18, 19, 20, 21, 22, 23, or 24 hours; about 1, 2, 3, 4, 5, 6, 7 days; about 1, 2, 3, or 4 weeks; or about 1, 2, 3, 4, 5, 6, 7, 8, 9, 10, 11, or 12 months before administration of an RA therapy (e.g., RA therapy that includes a DMARD, such as methotrexate). In some instances, a lymphoid eigengene score may be obtained from a sample from the individual that was collected at least about 1, 2, 3, 4, 5, 6, 7, 8, 9, 10, 11, 12, 13, 14, 15, 16, 17, 18, 19, 20, 21, 22, 23, or 24 hours; about 1, 2, 3, 4, 5, 6, 7 days; about 1, 2, 3, or 4 weeks; or about 1, 2, 3, 4, 5, 6, 7, 8, 9, 10, 11, or 12 months after administration of an RA therapy (e.g., RA therapy that includes a DMARD, such as methotrexate). The lymphoid eigengene scores from samples from the individual collected before and/or after the administration of the RA therapy (e.g., RA therapy that includes a DMARD, such as methotrexate) may be compared, wherein an increase in lymphoid eigengene score (e.g., an increase in the lymphoid eigengene score of about 10%, 20%, 30%, 40%, 50%, 60%, 70%, 80%, 90%, 95%, 96%, 97%, 98%, or 99% or greater) from a sample from the individual collected after treatment relative to a lymphoid eigengene score from a sample collected before treatment may indicate a low level of therapeutic efficacy of the RA therapy (e.g., RA therapy that includes a DMARD, such as methotrexate) that was administered, and wherein a decrease (e.g., a decrease in the lymphoid eigengene score of about 10%, 20%, 30%, 40%, 50%, 60%, 70%, 80%, 90%, 95%, 96%, 97%, 98%, or 99% or greater) in lymphoid eigengene score from a sample from the individual collected after treatment relative to a lymphoid eigengene score from a sample collected before treatment may indicate therapeutic efficacy of the RA therapy (e.g., RA therapy that includes a DMARD, such as methotrexate) that was administered. In some instances, the reference lymphoid eigengene score may be obtained from the individual prior to treatment with an RA therapy (e.g., RA therapy that includes a DMARD, such as methotrexate). In some instances, the method includes monitoring the lymphoid eigengene score from a sample form the individual relative to a pre-treatment lymphoid eigengene score during treatment (e.g., over a treatment period) with the RA therapy (e.g., RA therapy that includes a DMARD, such as methotrexate). In some instances, an elevated or increased lymphoid eigengene score, refers to an overall increase of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference lymphoid eigengene score. In some instances, an elevated lymphoid eigengene score refers to an overall increase of the lymphoid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference lymphoid eigengene score. In some instances, a reduced or decreased lymphoid eigengene score, refers to an overall decrease of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference lymphoid eigengene score. In some instances, a reduced lymphoid eigengene score refers to an overall decrease of the lymphoid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference lymphoid eigengene score.

In particular instances, the methods may include (i) determining a first myeloid eigengene score from a sample from the individual at a first time point during or after administration of a DMARD; (ii) determining a second myeloid eigengene score from a sample from the individual at a second time point; and (iii) comparing the first myeloid eigengene score with the second myeloid eigengene score, wherein a decrease in the second myeloid eigengene score (e.g., a decrease in the myeloid eigengene score of about 10%, 20%, 30%, 40%, 50%, 60%, 70%, 80%, 90%, 95%, 96%, 97%, 98%, or 99% or greater) relative to the first myeloid eigengene score below a reference eigengene score identifies the individual as one who is likely to respond to treatment with an RA therapy (e.g., RA therapy that includes a DMARD, such as methotrexate). In some instances, the method may further include administering and additional dose of an RA therapeutic agent to the individual. In some instances, a reduced or decreased myeloid eigengene score, refers to an overall decrease of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference myeloid eigengene score. In some instances, a reduced myeloid eigengene score refers to an overall decrease of the myeloid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference myeloid eigengene score.

In some instances, the method may further include prior to the administering of an RA therapy (e.g., RA therapy that includes a DMARD, such as methotrexate) (i) determining a first lymphoid eigengene score from a sample from the individual at a first time point during or after administration of a DMARD; (ii) determining a second lymphoid eigengene score from a sample from the individual at a second time point; and (iii) comparing the first lymphoid eigengene score with the second lymphoid eigengene score, wherein a decrease (e.g., a decrease in the lymphoid eigengene score of about 10%, 20%, 30%, 40%, 50%, 60%, 70%, 80%, 90%, 95%, 96%, 97%, 98%, or 99% or greater) in the second lymphoid eigengene score relative to the first lymphoid eigengene score identifies the individual as one who is likely to respond to treatment with an RA therapy (e.g., RA therapy that includes a DMARD, such as methotrexate). In some instances, a reduced or decreased lymphoid eigengene score, refers to an overall decrease of at least about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× relative to a reference lymphoid eigengene score. In some instances, a reduced lymphoid eigengene score refers to an overall decrease of the lymphoid eigengene score of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater relative to a reference lymphoid eigengene score.

In some instances of any of the therapeutic methods described above, the decrease in the second myeloid eigengene score relative to the first myeloid eigengene score is between about 1.25-fold to about 10-fold. In some instances, the decrease is between about 1.25-fold to about 7.5-fold. In some instances, the decrease is between about 1.25-fold to about 5-fold. In some instances, the decrease is between about 1.25-fold to about 2-fold. In some instances, the decrease is between about 1.25-fold to about 1.5 fold. In some instances, the decrease is at least about 1.25-fold.

In some instances of any of the therapeutic methods described above, the decrease in the second lymphoid eigengene score relative to the first lymphoid eigengene score is between about 1.25-fold to about 10-fold. In some instances, the decrease is between about 1.25-fold to about 7.5-fold. In some instances, the decrease is between about 1.25-fold to about 5-fold. In some instances, the decrease is between about 1.25-fold to about 2-fold. In some instances, the decrease is between about 1.25-fold to about 1.5 fold. In some instances, the decrease is at least about 1.25-fold.

In some instances of any of the therapeutic methods described above, the reference myeloid eigengene score may be a reference myeloid eigengene score in a reference population of individuals having RA who have been previously treated with a DMARD, the population of individuals consisting of a first subset of individuals who exhibited responded to the DMARD therapy and a second subset of individuals who did not respond to the DMARD therapy. In some instances, the reference myeloid eigengene score level significantly separates each of the first and second subsets of individuals based on a significant difference in the myeloid eigengene score in the first subset of individuals compared to that of the second subset of individuals. In some instances, the first subset of individuals responded to the DMARD therapy and the second subset did not respond to the DMARD therapy after about six months following the initiation of the DMARD therapy.

In some instances of any of the therapeutic methods described above, the reference lymphoid eigengene score may be a reference lymphoid eigengene score in a reference population of individuals having RA who have been previously treated with a DMARD, the population of individuals consisting of a first subset of individuals who exhibited responded to the DMARD therapy and a second subset of individuals who did not respond to the DMARD therapy. In some instances, the reference lymphoid eigengene score level significantly separates each of the first and second subsets of individuals based on a significant difference in the lymphoid eigengene score in the first subset of individuals compared to that of the second subset of individuals. In some instances, the first subset of individuals responded to the DMARD therapy and the second subset did not respond to the DMARD therapy after about six months following the initiation of the DMARD therapy.

In some instances of any of the preceding methods, the RA therapeutic agent may be a DMARD.

In some instances of any of the preceding methods, an RA therapeutic agent other than a DMARD may be administered.

In some instances of any of the preceding methods, a DMARD may be administered in conjunction with a therapeutic agent other than a DMARD.

In some instances of any of the preceding methods, a DMARD may include, but is not limited to, methotrexate, hydroxychloroquine, sulfasalazine, lefunomide, azathioprine, cyclophosphamide, cyclosporine, and mycophenolate mofetil.

In some instances of any of the preceding methods, the therapeutic agent other than a DMARD may include, but is not limited to, a B cell antagonist, a JAK antagonist, a TNF antagonist, a decoy TNF receptor, a T cell costimulatory signal antagonist, an IL-1 receptor antagonist, an IL-6 receptor antagonist, or a combination thereof.

In some instances of any of the preceding methods, the B cell antagonist may be, but is not limited to, rituximab (e.g., RITUXAN®).

In some instances of any of the preceding methods, the JAK antagonist may be, but is not limited to, tofacitinib (e.g. XELJANZ®).

In some instances of any of the preceding methods, the TNF antagonist may be, but is not limited to, adalimumab, golimumab, infliximab, certolizumab pegol, or a combination thereof.

In some instances of any of the preceding methods, the TNF decoy receptor may be, but is not limited to, etanercept.

In some instances of any of the preceding methods, the T cell costimulatory signal antagonist may be, but is not limited to, abatacept.

In some instances of any of the preceding methods, the IL-1 receptor antagonist may be, but is not limited to, anakinra.

In some instances of any of the preceding methods, the IL-6 receptor antagonist may be, but is not limited to, tocilizumab (e.g., ACTEMRA®/RoACTEMRA®).

In some instances of any of the preceding methods, the RA therapeutic agents utilized in the methods described herein can be administered, for example, orally, subcutaneously, intramuscularly, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subconjunctivally, intravesicularly, mucosally, intrapericardially, intraumbilically, intraocularly, intraorbitally, intravitreally (e.g., by intravitreal injection), by eye drop, topically, transdermally, parenterally, by inhalation, by injection, by implantation, by infusion, by continuous infusion, by localized perfusion bathing target cells directly, by catheter, by lavage, in creams, or in lipid compositions. In some instances of any of the preceding methods, the RA therapeutic agents utilized in the methods described herein can be administered orally. In some instances of any of the preceding methods, the RA therapeutic agents utilized in the methods described herein can be administered subcutaneously. The RA therapeutic agents utilized in the methods described herein can also be administered systemically or locally. The method of administration can vary depending on various factors (e.g., the RA therapeutic agents being administered and the severity of the condition, disease, or disorder (e.g., RA) being treated).

III. Compositions and Pharmaceutical Formulations

In one aspect, the invention is based, in part, on the discovery that biomarkers of the invention can be used to identify individuals having RA who may benefit from an RA therapy, for example, a DMARD (e.g., a DMARD), or a therapy including a biologic therapeutic agent (e.g., a biologic therapeutic agent), alone or in combination with a DMARD.

In some instances, the individual is less likely to respond to the DMARD alone. In another instance, the invention is based, in part, on the discovery that biomarkers of the invention can be used to monitor and/or assess treatment response for individuals having RA who are treated with RA therapies that include a DMARD. These agents, and combinations thereof, are useful for the treatment of RA, e.g., as part of any of the methods and uses described herein, for example, in Section II above. Any suitable DMARD can be used in the methods and uses described herein.

A. Pharmaceutical Formulations

Therapeutic formulations of the therapeutic agents, e.g., a DMARD and/or a biologic therapeutic agent, used in accordance with the present invention are prepared for storage by mixing the therapeutic agent having the desired degree of purity with optional pharmaceutically acceptable carriers, excipients, or stabilizers in the form of lyophilized formulations or aqueous solutions. For general information concerning formulations, see, e.g., Gilman et al. (eds.) *The Pharmacological Bases of Therapeutics,* 8th Ed., Pergamon Press, 1990; A. Gennaro (ed.), *Remington's Pharmaceutical Sciences,* 18th Edition, Mack Publishing Co., Pennsylvania, 1990; Avis et al. (eds.) *Pharmaceutical Dosage Forms: Parenteral Medications* Dekker, New York, 1993; Lieberman et al. (eds.) *Pharmaceutical Dosage Forms: Tablets* Dekker, New York, 1990; Lieberman et al. (eds.), *Pharmaceutical Dosage Forms: Disperse Systems* Dekker, New York, 1990; and Walters (ed.) *Dermatological and Transdermal Formulations* (Drugs and the Pharmaceutical Sciences), Vol 119, Marcel Dekker, 2002.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

The formulation herein may also contain more than one active compound, preferably those with complementary activities that do not adversely affect each other. The type and effective amounts of such medicaments depend, for example, on the amount and type of therapeutic agent (e.g., a DMARD and/or a biologic therapeutic agent) present in the formulation, and clinical parameters of the patients.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in *Remington's Pharmaceutical Sciences* 16th edition, Osol, A. Ed., 1980.

Sustained-release preparations may be prepared. Suitable examples of sustained-release preparations include semipermeable matrices of solid hydrophobic polymers containing the therapeutic agent, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

IV. Articles of Manufacture and Kits

In another aspect of the invention, a kit or an article of manufacture containing materials useful for the treatment, prevention, diagnosis, and/or monitoring of individuals is provided.

In some instances, such kits or articles of manufacture can be used to identify an individual having RA who may benefit from an RA therapy that includes a therapeutic agent other than or in addition to a DMARD (including, but not limited to, a biologic therapeutic agent alone, or a biologic therapeutic agent and a DMARD). Such articles of manufacture or kits may include (i) reagent(s) for determining the expression level of one or more genes set forth in Table 1, or any combination thereof (e.g., any combination set forth in any one of Tables 2 and 3) in a sample from the individual, and, optionally, (ii) instruction(s) for using the reagent(s) to identify an individual having RA who may benefit from treatment with an RA therapy that includes a therapeutic agent other than, or in addition to, a DMARD. In additional instances, the articles of manufacture or kits may include (i) reagent(s) for determining the expression level of one or more genes set forth in Table 1, or any combination thereof (e.g., any combination set forth in any one of Tables 2 and 3) in a sample from the individual, and, optionally, (ii) instruction(s) for using the reagents to monitor and/or assess the response of an individual having RA to treatment with an RA therapy that includes a therapeutic agent other than, or in addition to, a DMARD (e.g., a biologic therapeutic agent alone, or a biologic therapeutic agent and a DMARD).

In some instances, such kits or articles of manufacture can be used to identify an individual having RA who may benefit from an RA therapy that includes a therapeutic agent other than, or in addition to, a DMARD (including, but not limited to, a biologic therapeutic agent alone, or a biologic therapeutic agent and a DMARD). Such articles of manufacture or kits may include (i) reagent(s) for determining the expression level of one or more genes set forth in Table 1, or any combination thereof (e.g., any combination set forth in any one of Tables 2 and 3) in a sample from the individual and (ii) instruction(s) for using the reagent(s) to identify an individual having RA who may benefit from treatment with an RA therapy that includes a therapeutic agent other than, or in addition to, a DMARD. In additional instances, the articles of manufacture or kits may include (i) reagent(s) for determining the expression level of one or more genes set forth in Table 1, or any combination thereof (e.g., any combination set forth in any one of Tables 2 and 3) in a sample from the individual and (ii) instruction(s) for using the reagents to monitor and/or assess the response of an individual having RA to treatment with an RA therapy that includes a therapeutic agent other than, or in addition to, a DMARD (e.g., a biologic therapeutic agent alone, or a biologic therapeutic agent and a DMARD).

Provided herein is a kit or an article of manufacture for identifying an individual having RA who may benefit from treatment with a therapeutic agent other than, or in addition to, a DMARD (e.g., a biologic therapeutic agent alone, or a biologic therapeutic agent and a DMARD), the kit or article of manufacture including: (i) reagents for determining the expression level of one or more of the genes set forth in Table 1 (e.g., 1, 2, 3, 4, 5, 6, 7, 8, 9, 10, 11, 12, 13, 14, 15, 16, 17, 18, 19, 20, 21, 21, 22, 23, 24, 25, 26, 27, 28, 29, 30, 31, 32, 33, 34, 35, 36, 37, 38, 39, 40, 41, 42, 43, 44, 45, or 46 of the genes set forth in Table 1) in a sample from the individual, and, optionally, (ii) instructions for using the reagents to identify an individual having RA who may benefit from a treatment with an RA therapy comprising a therapeutic agent other than, or in addition to, a DMARD.

For example, provided herein is a kit or an article of manufacture for identifying an individual having RA who may benefit from treatment with an RA therapy (e.g., a biologic therapeutic agent alone, or a biologic therapeutic agent and a DMARD), the kit or article of manufacture including: (i) reagents for determining the expression level of one or more of the following genes in a sample from the individual: CD180, CSF2, CXCL1, DENND1C, MMP10, SDC1, and UBASH3A (e.g., 1, 2, 3, 4, 5, 6, or 7 of CD180, CSF2, CXCL1, DENND1C, MMP10, SDC1, and UBASH3A), and, optionally, (ii) instructions for using the reagents to identify an individual having RA who may benefit from a treatment with an RA therapy comprising a therapeutic agent other than, or in addition to, a DMARD.

In any of the preceding instances, the kit may include reagents for determining the expression level of one or more (e.g., 1, 2, 3, 4, 5, 6, or 7) of CD180, CSF2, CXCL1, DENND1C, MMP10, SDC1, and UBASH3A. In some embodiments, the kit includes reagents for determining the expression level of two of CD180, CSF2, CXCL1, DENND1C, MMP10, SDC1, and UBASH3A, for example, any of the exemplary combinations shown in Table 4. In some embodiments, the kit includes reagents for includes determining the expression level of three of CD180, CSF2, CXCL1, DENND1C, MMP10, SDC1, and UBASH3A, for example, any of the exemplary combinations shown in Table 5. In some embodiments, the kit includes reagents for includes determining the expression level of four of CD180, CSF2, CXCL1, DENND1C, MMP10, SDC1, and UBASH3A, for example, any of the exemplary combinations shown in Table 6. In some embodiments, the kit includes reagents for includes determining the expression level of five of CD180, CSF2, CXCL1, DENND1C, MMP10, SDC1, and UBASH3A, for example, any of the exemplary combinations shown in Table 7. In some embodiments, the kit includes reagents for includes determining the expression level of six of CD180, CSF2, CXCL1, DENND1C, MMP10, SDC1, and UBASH3A, for example, any of the exemplary combinations shown in Table 8. In some embodiments, the kit includes reagents for involves determining the expression level of CD180, CSF2, CXCL1, DENND1C, MMP10, SDC1, and UBASH3A, and, optionally, (ii) instructions for using the reagents to identify an individual having RA who may benefit from a treatment with an RA therapy comprising a therapeutic agent other than, or in addition to, a DMARD.

In some instances, such kits or articles of manufacture can be used to identify an individual having RA who may benefit from an RA therapy that includes a DMARD (including, but not limited to, a DMARD and/or a biologic therapeutic agent). Such articles of manufacture or kits may include (i) reagents for determining the myeloid eigengene, or myeloid eigengene and lymphoid eigengene score(s) in a sample from the individual, and, optionally, (ii) instructions for using the reagents to identify an individual having RA who may benefit from treatment with an RA therapy that includes a DMARD.

In additional instances, the articles of manufacture or kits may include (i) reagents for determining the myeloid eigengene, or myeloid eigengene and lymphoid eigengene score(s) in a sample from the individual, and, optionally, (ii) instructions for using the reagents to monitor and/or assess the response of an individual having RA to treatment with an RA therapy that includes a DMARD (e.g., a DMARD and/or a biologic therapeutic agent).

Provided herein is a kit or an article of manufacture for identifying an individual having RA who may benefit from treatment with an RA therapy (e.g., a biologic therapeutic agent alone, or a biologic therapeutic agent and a DMARD), the kit or article of manufacture including: (i) reagents for determining the expression level of one or more of the genes set forth in Table 1 (e.g., 1, 2, 3, 4, 5, 6, 7, 8, 9, 10, 11, 12, 13, 14, 15, 16, 17, 18, 19, 20, 21, 21, 22, 23, 24, 25, 26, 27, 28, 29, 30, 31, 32, 33, 34, 35, 36, 37, 38, 39, 40, 41, 42, 43, 44, 45, or 46 of the genes set forth in Table 1) in a sample from the individual, and (ii) instructions for using the reagents to identify an individual having RA who may benefit from a treatment with an RA therapy comprising a therapeutic agent other than, or in addition to, a DMARD.

For example, provided herein is a kit or an article of manufacture for identifying an individual having RA who may benefit from treatment with an RA therapy (e.g., a biologic therapeutic agent alone, or a biologic therapeutic agent and a DMARD), the kit or article of manufacture including: (i) reagents for determining the expression level of one or more (e.g., 1, 2, 3, 4, 5, 6, or 7) of the following genes in a sample from the individual: CD180, CSF2, CXCL1, DENND1C, MMP10, SDC1, and UBASH3A, and (ii) instructions for using the reagents to identify an individual having RA who may benefit from a treatment with an RA therapy comprising a therapeutic agent other than, or in addition to, a DMARD.

In any of the preceding instances, the kit may include reagents for determining the expression level of one or more (e.g., 1, 2, 3, 4, 5, 6, or 7) of CD180, CSF2, CXCL1, DENND1C, MMP10, SDC1, and UBASH3A. In some embodiments, the kit includes reagents for determining the expression level of at least two, at least three, at least four, at least five, at least six, or all seven of CD180, CSF2, CXCL1, DENND1C, MMP10, SDC1, and UBASH3A. In some embodiments, the kit includes reagents for includes determining the expression level of two of CD180, CSF2, CXCL1, DENND1C, MMP10, SDC1, and UBASH3A, for example, any of the exemplary combinations shown in Table 4. In some embodiments, the kit includes reagents for includes determining the expression level of three of CD180, CSF2, CXCL1, DENND1C, MMP10, SDC1, and UBASH3A, for example, any of the exemplary combinations shown in Table 5. In some embodiments, the kit includes reagents for includes determining the expression level of four of CD180, CSF2, CXCL1, DENND1C, MMP10, SDC1, and UBASH3A, for example, any of the exemplary combinations shown in Table 6. In some embodiments, the kit includes reagents for includes determining the expression level of five of CD180, CSF2, CXCL1, DENND1C, MMP10, SDC1, and UBASH3A, for example, any of the exemplary combinations shown in Table 7. In some embodiments, the kit includes reagents for includes determining the expression level of six of CD180, CSF2, CXCL1, DENND1C, MMP10, SDC1, and UBASH3A, for example, any of the exemplary combinations shown in Table 8. In some embodiments, the kit includes reagents for involves determining the expression level of CD180, CSF2, CXCL1, DENND1C, MMP10, SDC1, and UBASH3A, and instructions for using the reagents to identify an individual having RA who may benefit from a treatment with an RA therapy comprising a therapeutic agent other than, or in addition to, a DMARD.

In some instances, such kits or articles of manufacture can be used to identify an individual having RA who may benefit from an RA therapy that includes a DMARD (including, but not limited to, a DMARD and/or a biologic therapeutic agent). Such articles of manufacture or kits may include (i) reagents for determining the myeloid eigengene, or myeloid eigengene and lymphoid eigengene score(s) in a sample from the individual, and (ii) instructions for using the reagents to identify an individual having RA who may benefit from treatment with an RA therapy that includes a DMARD.

In additional instances, the articles of manufacture or kits may include (i) reagents for determining the myeloid eigengene, or myeloid eigengene and lymphoid eigengene score(s) in a sample from the individual and, (ii) instructions for using the reagents to monitor and/or assess the response of an individual having RA to treatment with an RA therapy that includes a DMARD (e.g., a DMARD and/or a biologic therapeutic agent).

Provided herein is a kit or an article of manufacture for treating an individual with RA, the kit or article of manufacture including (i) a biologic therapeutic agent alone, or a biologic therapeutic agent and a DMARD, and (ii) instructions for administering to an individual an effective amount of the biologic therapeutic agent alone, or the biologic therapeutic agent and the DMARD to treat or delay the progression of RA in the individual, based on the determination of an increased expression level of one or more of the genes set forth in Table 2 (e.g., 1, 2, 3, 4, 5, 6, 7, 8, 9, 10, 11, 12, 13, 14, 15, 16, 17, 18, 19, 20, 21, 21, 22, 23, 24, 25, 26, 27, 28, 29, 30, 31, 32, 33, 34, 35, 36, 37, 38, 39, or 40 of the genes set forth in Table 2) in a sample from the individual relative to a reference expression level.

Provided herein is a kit or an article of manufacture for treating an individual with RA, the kit or article of manufacture including (i) a biologic therapeutic agent alone, or a biologic therapeutic agent and a DMARD, and (ii) instructions for administering to an individual an effective amount of the biologic therapeutic agent alone, or the biologic therapeutic agent and the DMARD to treat or delay the progression of RA in the individual, based on the determination of an increased expression level of one or more of the following genes in a sample from the individual: CD180, CSF2, CXCL1, DENND1C, MMP10, SDC1, and UBASH3A (e.g., 1, 2, 3, 4, 5, 6, or 7 of CD180, CSF2, CXCL1, DENND1C, MMP10, SDC1, and UBASH3A) in a sample from the individual relative to a reference expression level.

In some embodiments, the kit includes instructions for administering to an individual an effective amount of the biologic therapeutic agent alone, or the biologic therapeutic agent and the DMARD to treat or delay the progression of RA in the individual, based on the determination of an increased expression level of at least two, at least three, at least four, at least five, at least six, or all seven of CD180, CSF2, CXCL1, DENND1C, MMP10, SDC1, and UBASH3A in a sample from the individual relative to a reference expression level.

In some embodiments, the kit includes instructions for administering to an individual an effective amount of the biologic therapeutic agent alone, or the biologic therapeutic agent and the DMARD to treat or delay the progression of RA in the individual, based on the determination of an increased expression level of two of CD180, CSF2, CXCL1, DENND1C, MMP10, SDC1, and UBASH3A, for example, any of the exemplary combinations shown in Table 4 in a sample from the individual relative to a reference expression level.

In some embodiments, the kit includes instructions for administering to an individual an effective amount of the biologic therapeutic agent alone, or the biologic therapeutic agent and the DMARD to treat or delay the progression of RA in the individual, based on the determination of an increased expression level of three of CD180, CSF2, CXCL1, DENND1C, MMP10, SDC1, and UBASH3A, for example, any of the exemplary combinations shown in Table 5 in a sample from the individual relative to a reference expression level.

In some embodiments, the kit includes instructions for administering to an individual an effective amount of the biologic therapeutic agent alone, or the biologic therapeutic agent and the DMARD to treat or delay the progression of RA in the individual, based on the determination of an increased expression level of four of CD180, CSF2, CXCL1, DENND1C, MMP10, SDC1, and UBASH3A, for example, any of the exemplary combinations shown in Table 6 in a sample from the individual relative to a reference expression level.

In some embodiments, the kit includes instructions for administering to an individual an effective amount of the biologic therapeutic agent alone, or the biologic therapeutic agent and the DMARD to treat or delay the progression of RA in the individual, based on the determination of an increased expression level of five of CD180, CSF2, CXCL1, DENND1C, MMP10, SDC1, and UBASH3A, for example, any of the exemplary combinations shown in Table 7 in a sample from the individual relative to a reference expression level.

In some embodiments, the kit includes instructions for administering to an individual an effective amount of the biologic therapeutic agent alone, or the biologic therapeutic agent and the DMARD to treat or delay the progression of RA in the individual, based on the determination of an increased expression level of six of CD180, CSF2, CXCL1, DENND1C, MMP10, SDC1, and UBASH3A, for example, any of the exemplary combinations shown in Table 8 in a sample from the individual relative to a reference expression level.

In some embodiments, the kit includes instructions for administering to an individual an effective amount of the biologic therapeutic agent alone, or the biologic therapeutic agent and the DMARD to treat or delay the progression of RA in the individual, based on the determination of an increased expression level of CD180, CSF2, CXCL1, DENND1C, MMP10, SDC1, and UBASH3A, in a sample from the individual relative to a reference expression level.

Provided herein is a kit or an article of manufacture for treating an individual with RA, the kit or article of manufacture including (i) an RA therapeutic agent (e.g., a biologic therapeutic agent alone, or a biologic therapeutic agent and a DMARD), and (ii) instructions for administering to an individual an effective amount of the biologic therapeutic agent alone, or the biologic therapeutic agent and a DMARD to treat or delay the progression of RA in the individual, based on the determination of a decreased expression level of one or more of the genes set forth in Table 3 (e.g., 1, 2, 3, 4, 5, or 6, of the genes set forth in Table 3) in a sample from the individual relative to a reference expression level.

Provided herein is a kit or an article of manufacture for treating an individual with RA, the kit or article of manufacture including (i) an RA therapeutic agent (e.g., a DMARD and/or a biologic therapeutic agent), and (ii) instructions for administering to an individual an effective amount of the RA therapeutic agent to treat or delay the progression of RA in the individual, based on the determination of an increased myeloid eigengene score in a sample from the individual relative to a reference myeloid eigengene score.

Provided herein is a kit or an article of manufacture for treating an individual with RA, the kit or article of manufacture including (i) an RA therapeutic agent (e.g., a DMARD and/or a biologic therapeutic agent), and (ii) instructions for administering to an individual an effective amount of the RA therapeutic agent to treat or delay the progression of RA in the individual, based on the determination of an increased myeloid eigengene score and an increased lymphoid eigengene score in a sample from the individual relative to a reference myeloid eigengene score and a reference lymphoid eigengene score.

Any of the kits or articles of manufacture described may include a carrier means being compartmentalized to receive in close confinement one or more container means such as vials, tubes, and the like, each of the container means comprising one of the separate elements to be used in the method. Where the article of manufacture or kit utilizes nucleic acid hybridization to detect the target nucleic acid, the kit may also have containers containing nucleotide(s) for amplification of the target nucleic acid sequence and/or a container comprising a reporter-means, such as an enzymatic, florescent, or radioisotope label.

In some instances, the article of manufacture or kit includes the container described above and one or more other containers including materials desirable from a commercial and user standpoint, including buffers, diluents, filters, needles, syringes, and package inserts with instructions for use. A label may be present on the container to indicate that the composition is used for a specific application, and may also indicate directions for either in vivo or in vitro use, such as those described above. For example, the article of manufacture or kit may further include a container including a pharmaceutically-acceptable buffer, such as bacteriostatic water for injection (BWFI), phosphate-buffered saline, Ringer's solution, and dextrose solution.

The kits or articles of manufacture described herein may have a number of instances. In one instance, the kits or articles of manufacture includes a container, a label on said container, and a composition contained within said container, wherein the composition includes one or more polynucleotides that hybridize to a complement of a gene listed herein (e.g., a gene set forth in Table 1, or any combination of genes set forth in Tables 2 and 3) under stringent conditions, and the label on said container indicates that the composition can be used to evaluate the presence of a gene listed herein (e.g., a gene set forth in Table 1, or any combination of genes set forth in Tables 2 and 3) in a sample, and wherein the kit includes instructions for using the polynucleotide(s) for evaluating the presence of the gene RNA or DNA in a particular sample type.

For oligonucleotide-based articles of manufacture or kits, the article of manufacture or kit can include, for example: (1) an oligonucleotide, e.g., a detectably labeled oligonucleotide, which hybridizes to a nucleic acid sequence encoding a protein or (2) a pair of primers useful for amplifying a nucleic acid molecule. The article of manufacture or kit can also include, e.g., a buffering agent, a preservative, or a protein stabilizing agent. The article of manufacture or kit can further include components necessary for detecting the detectable label (e.g., an enzyme or a substrate). The article of manufacture or kit can also contain a control sample or a series of control samples that can be assayed and compared to the test sample. Each component of the article of manufacture or kit can be enclosed within an individual container and all of the various containers can be within a single package, along with instructions for interpreting the results of the assays performed using the kit.

V. Examples

The following are examples of the methods of the invention. It is understood that various other embodiments may be practiced, given the general description provided above.

Example 1. Association Between Immunohistochemistry (IHC) Pathotypes and Gene Expression Levels of Individuals Having Rheumatoid Arthritis (RA)

Ultrasound-guided synovial biopsies were collected from a cohort of 129 individuals enrolled in the Pathobiology of Early Arthritis Cohort (PEAC), a treatment-naïve, early rheumatoid arthritis (RA) patient population with less than 12 months of symptoms duration. Histological analyses and gene expression microarray experiments were performed on isolated synovial tissues to identify pathotype-specific cellular and gene expression markers, evaluate the association between gene expression patterns and the progression of disease, and identify potential biomarkers for prognostic and predictive purposes.

Study Design

144 RA individuals fulfilling 2010 American College of Rheumatology (ACR)/European League Against Rheumatism (EULAR) RA Classification Criteria were enrolled at Barts Health National Health Service (NHS) trust as part of the Medical Research Council (MRC) funded multi-center Pathobiology of Early Arthritis Cohort (PEAC). The study received local ethical approval, and all individuals gave written informed consent. Individuals presented with clinically defined synovitis, but with a duration of symptoms of less than 12 months. Study subject characteristics are summarized in FIG. 1A. Briefly, the average DAS28-ESR score was 5.6 (SD 1.5), approximately 65% were positive for rheumatoid factor and/or anti-citrullinated peptide antibodies (ACPA), and 20% had at least one radiographic erosion. All individuals were naïve to disease-modifying antirheumatic drug (DMARD) and steroid therapy. Upon enrollment and acquisition of demographic and clinical disease parameters, individuals underwent minimally invasive ultrasound (US)-guided synovial biopsy of a clinically active joint (FIG. 1B). The majority of joints biopsied in this cohort were from the wrist (approximately 65%), with additional representation from MCP/PIP/MTP joints (approximately 15%), while the knee and the elbow together comprised approximately 20% (FIG. 1C). Individuals were subsequently commenced on standard DMARD therapy (methotrexate (MTX), sulphasalasine (SSZ), and/or hydroxychloroquine (HCQ)) and/or low-dose steroid (intramuscular or oral). A treat-to-target approach to treatment escalation was followed with an aim of low disease activity: 28 joints-disease activity score (DAS28)<3.2. Individuals failing DMARD therapy were commenced on biologic therapy according to the UK National Institute for Clinical Excellence (NICE) prescribing algorithm for RA individuals if they continued to have a DAS28>5.1 at 6 months. After 6 months of treatment, a second synovial biopsy was performed on the same joint (unless clinically contraindicated), together with assessment of disease activity. Ultrasonography scores were collected at the time of biopsy for both the individual biopsied joint as well as a global joint score. Immediately prior to baseline, US-guided synovial biopsy standard longitudinal images of the $1^{st}$-$5^{th}$ metacarpo-phalangeal (MCP) joints and midline, radial, and ulnar views of both wrist joints were acquired in addition to standard images of the joint undergoing US-guided synovial biopsy. Images subsequently underwent semi-quantitative (SQ) assessment by a blinded assessor (IL) for both synovial thickening (ST) and power doppler activity (PD) according to standard EULAR outcome measures in rheumatology (OMERACT) US synovitis scores (grade 0-3). For each individual, baseline total mean (12max) ST (STUS) and PD (PDUS) scores were calculated by deriving the mean of the total scores for ST and PD for all 12 joints, including maximal score in the wrist. STUS and PDUS were also recorded of the biopsied joint. Anonymized plain radiographs of the hands and feet performed at baseline and at 12-month follow-up were scored in time-sequential order according to the van der Heijde modified Sharp score (ShSS) by a trained reader.

Identification of Synovial Pathotypes Based Upon Histology

To classify individuals into disease pathotypes, synovial biopsy tissue samples were evaluated by immunohistochemical methods. A minimum of six biopsies were paraffin embedded, and 3-μM sections underwent routine hematoxylin and eosin (H&E) staining and were assessed for morphology and sample integrity. Synovial tissue samples collected from 129 of the 144 recruited individuals met sample integrity criteria and were processed for further analyses. In order to determine the degree of immune cell infiltration, sequentially cut sections underwent staining for B cells (CD20), T cells (CD3), macrophages (CD68), and plasma cells (CD138). Sections then underwent SQ scoring (0-4) for CD3, CD20, CD68 lining (CD68l) and sublining (CD68sl), and CD138 number. The presence of CD20+ aggregates within synovial tissue was noted, and aggregates were graded (1-3) according to a previously published scoring system (Humby et al. *PLos Medicine* 6(1):e1, 2009).

Biopsies were then stratified into 1 of 3 synovial pathotypes according to the following criteria: (i) Lymphoid: presence of grade 2-3 CD20+ aggregates, (CD20 2), and/or CD138>2; (ii) Myeloid: CD68 SL≥2, CD20≤1, and/or CD3≥1, CD138≤2; and (iii) Pauciimmune-fibroid: CD68 SL<2 and CD3, CD20, and CD138<1. Representative microphotographs are shown in FIG. 2A. Overall, 39% of individuals had a lymphoid pathotype (n=51) rich in immune cells (T, B, and plasma cells); 34% had a myeloid pathotype (n=44) characterized by prevalence of macrophages and T cells, but few B cells and plasma cells; and 27% had a pauciimmune-fibroid pathotype (n=34) characterized by expansion of fibroblasts, but very few immune cells (FIG. 2B).

Identification of Pathotype-Specific Gene Expression Markers

To identify genes that were differentially expressed among the three major pathotype clusters, total RNA was extracted from the synovial tissue collected from the subset of PEAC individuals. Synovial samples were homogenized in TRIzol Reagent (ThermoFisher Scientific, Life Technologies, Invitrogen Division, UK) using a rotor-stator homogenizer following shearing with a 26-gauge needle. Total RNA was isolated according to the manufacturer's protocol and stored at −80° C. All RNA samples were quantified using spectrophotometric analysis performed on the NanoDrop-ND2000C system (Lab Tech, UK). RNA integrity was determined by RNA Nanochip electrophoresis on the Agilent 2100 Bioanalyzer system (Agilent Technologies, UK). Following confirmation of RNA integrity, 1 μg of total RNA, where available, was used for library preparation using TruSeq RNA Sample Preparation Kit v2 (Illumina). Generated libraries were first amplified with 10 cycles of PCR, the size of the libraries was confirmed using 2200 TapeStation and High Sensitivity D1K screen tape (Agilent Technologies), and their concentration was determined by a qPCR-based method using a library quantification kit (KAPA). The libraries were first multiplexed (five per lane), and then sequenced on Illumina HiSeq2500 (Illumina) to generate 50 million paired-end 75-bp reads.

Processing and analysis of the RNA-sequencing data was performed using the R programming language, along with packages from the Bioconductor Project. Raw RNA-sequencing reads were processed using the HTSeqGenie Bioconductor package (v. 4.0.1). Briefly, reads were aligned to the reference human genome sequence (build 38) using the GSNAP algorithm and the following parameters: -M 2 -n 10 -B 2 -i 1 -N 1 -w 200000 -E 1 -pairmax-ma=200000 -clip-overlap. Uniquely aligned read pairs that fell within exons were counted to give an estimate of expression levels for individual genes. Data were further normalized using the variance stabilizing transformation implemented in the DESeq2 Bioconductor package.

To identify pathotype specific genes, differential expression analysis was performed on the pathotypes classified in a previous microarray study (GEO accession number GSE48780; Dennis et al. Arthritis Research and Therapy. 16(2): R90, 2014). Pairwise comparisons were performed between samples in the pauciimmune-fibroid, myeloid, and lymphoid pathotypes. Genes were selected for a pathotype if they showed differential expression with each of the other two pathotypes at a Benjamini-Hochberg adjusted p-value<0.01. These genes were then queried in the baseline RNA-seq data from a subset of 90 individuals from the PEAC cohort.

For each set of pathotype specific genes, 50 genes were identified that best correlated with the first principal component of the z-score transformed expression data for that gene set. An additional set of 87 genes previously implicated in RA pathobiology were also included. Expression levels determined by NANOSTRING® were concordant with those measured by RNA-sequencing, in samples where both measurements were available (FIG. 2C). Analyses of NANOSTRING® expression data were performed using R version 3.3.2. For differential expression analyses, the limma Bioconductor package was used with default settings. The Benjamini-Hochberg method was used to adjust for multiple testing, and genes were considered to be differentially expressed if they had an adjusted p-value<0.01. Closer examination of the myeloid pathotype markers identified two clusters of genes, with high correlation within each cluster, but only modest correlation between them. The larger cluster was selected, which contained known myeloid cell-expressed markers, including CD86, PILRA, and C5AR1, as a marker gene set for the myeloid pathotype, reducing the myeloid gene set to 26 genes. The final NANOSTRING® dataset included 212 probes: 49 lymphoid-specific genes (Table 9), 26 myeloid-specific genes (Table 10), 50 pauciimmune-fibroid-specific genes (Table 11), and 87 RA biology-associated genes (Table 12).

TABLE 9

Lymphoid-Specific Genes

| NCBI Gene ID | Gene Name |
| --- | --- |
| 973 | CD79A |
| 80342 | TRAF3IP3 |
| 50615 | IL21R |
| 9840 | TESPA1 |
| 11262 | SP140 |
| 50619 | DEF6 |
| 23231 | SEL1L3 |
| 83416 | FCRL5 |
| 3561 | IL2RG |
| 931 | MS4A1 |
| 64098 | PARVG |
| 221188 | ADGRG5 |
| 3932 | LCK |
| 80008 | TMEM156 |
| 114836 | SLAMF6 |
| 3738 | KCNA3 |
| 11040 | PIM2 |
| 923 | CD6 |
| 9938 | ARHGAP25 |
| 4063 | LY9 |
| 916 | CD3E |
| 914 | CD2 |
| 26279 | PLA2G2D |
| 399 | RHOH |
| 147138 | TMC8 |
| 79961 | DENND2D |
| 151888 | BTLA |
| 79958 | DENND1C |

TABLE 9-continued

Lymphoid-Specific Genes

| NCBI Gene ID | Gene Name |
| --- | --- |
| 81793 | TLR10 |
| 100505746 | ITGB2-AS1 |
| 91523 | PCED1B |
| 57823 | SLAMF7 |
| 55423 | SIRPG |
| 4064 | CD180 |
| 374403 | TBC1D10C |
| 54440 | SASH3 |
| 84433 | CARD11 |
| 11322 | TMC6 |
| 53347 | UBASH3A |
| 5133 | PDCD1 |
| 84941 | HSH2D |
| 201633 | TIGIT |
| 9834 | FAM30A |
| 11184 | MAP4K1 |
| 3112 | HLA-DOB |
| 6693 | SPN |
| 81030 | ZBP1 |
| 6689 | SPIB |
| 5450 | POU2AF1 |

TABLE 10

Myeloid-Specific Genes

| NCBI Gene ID | Gene Name |
| --- | --- |
| 54443 | ANLN |
| 3687 | ITGAX |
| 114548 | NLRP3 |
| 126014 | OSCAR |
| 84034 | EMILIN2 |
| 3576 | CXCL8 |
| 4688 | NCF2 |
| 5329 | PLAUR |
| 8843 | HCAR3 |
| 1230 | CCR1 |
| 2921 | CXCL3 |
| 2203 | FBP1 |
| 30817 | ADGRE2 |
| 23601 | CLEC5A |
| 9582 | APOBEC3B |
| 6696 | SPP1 |
| 55357 | TBC1D2 |
| 2710 | GK |
| 29992 | PILRA |
| 942 | CD86 |
| 728 | C5AR1 |
| 6364 | CCL20 |
| 55092 | TMEM51 |
| 58191 | CXCL16 |
| 64127 | NOD2 |
| 53831 | GPR84 |
| 1317 | SLC31A1 |

TABLE 11

Pauciimmune-Fibroid-Specific Genes

| NCBI Gene ID | Gene Name |
| --- | --- |
| 11328 | FKBP9 |
| 10810 | WASF3 |
| 57498 | KIDINS220 |
| 9627 | SNCAIP |
| 8555 | CDC14B |
| 23259 | DDHD2 |
| 84255 | SLC37A3 |
| 200734 | SPRED2 |
| 121227 | LRIG3 |

TABLE 11-continued

Pauciimmune-Fibroid-Specific Genes

| NCBI Gene ID | Gene Name |
|---|---|
| 84632 | AFAP1L2 |
| 57088 | PLSCR4 |
| 4952 | OCRL |
| 23348 | DOCK9 |
| 858 | CAV2 |
| 23270 | TSPYL4 |
| 10129 | FRY |
| 79188 | TMEM43 |
| 256356 | GK5 |
| 26224 | FBXL3 |
| 9639 | ARHGEF10 |
| 56256 | SERTAD4 |
| 8853 | ASAP2 |
| 10186 | LHFPL6 |
| 7289 | TULP3 |
| 90 | ACVR1 |
| 10194 | TSHZ1 |
| 51439 | FAM8A1 |
| 57515 | SERINC1 |
| 260425 | MAGI3 |
| 57161 | PELI2 |
| 342371 | ATXN1L |
| 3096 | HIVEP1 |
| 7220 | TRPC1 |
| 25959 | KANK2 |
| 91404 | SESTD1 |
| 55970 | GNG12 |
| 51421 | AMOTL2 |
| 8613 | PLPP3 |
| 151011 | SEPT10 |
| 5325 | PLAGL1 |
| 54682 | MANSC1 |
| 23328 | SASH1 |
| 79901 | CYBRD1 |
| 10427 | SEC24B |
| 2059 | EPS8 |
| 5311 | PKD2 |
| 79633 | FAT4 |
| 5066 | PAM |
| 8476 | CDC42BPA |
| 5358 | PLS3 |

TABLE 12

RA Biology-Associated Genes

| NCBI Gene ID | Gene Name | NCBI Gene ID | Gene Name |
|---|---|---|---|
| 115650 | TNFRSF13C | 952 | CD38 |
| 7049 | TGFBR3 | 6363 | CCL19 |
| 4312 | MMP1 | 1440 | CSF3 |
| 4599 | MX1 | 4314 | MMP3 |
| 7494 | XBP1 | 4050 | LTB |
| 11009 | IL24 | 608 | TNFRSF17 |
| 7078 | TIMP3 | 4940 | OAS3 |
| 640 | BLK | 4982 | TNFRSF11B |
| 2331 | FMOD | 3553 | IL1B |
| 929 | CD14 | 7481 | WNT11 |
| 3489 | IGFBP6 | 439921 | MXRA7 |
| 3543 | IGLL1 | 5154 | PDGFA |
| 7852 | CXCR4 | 55801 | IL26 |
| 59067 | IL21 | 959 | CD40LG |
| 50616 | IL22 | 4318 | MMP9 |
| 7124 | TNF | 6097 | RORC |
| 5175 | PECAM1 | 8792 | TNFRSF11A |
| 1311 | COMP | 4322 | MMP13 |
| 9235 | IL32 | 9671 | WSCD2 |
| 695 | BTK | 3512 | JCHAIN |
| 27177 | IL36B | 3429 | IFI27 |
| 8600 | TNFSF11 | 3440 | IFNA2 |
| 3598 | IL13RA2 | 53342 | IL17D |
| 29851 | ICOS | 11096 | ADAMTS5 |
| 7076 | TIMP1 | 27122 | DKK3 |
| 3439 | IFNA1 | 10563 | CXCL13 |
| 3383 | ICAM1 | 50604 | IL20 |
| 57379 | AICDA | 930 | CD19 |
| 6280 | S100A9 | 79037 | PVRIG |
| 6382 | SDC1 | 4939 | OAS2 |
| 2247 | FGF2 | 2919 | CXCL1 |
| 3458 | IFNG | 5803 | PTPRZ1 |
| 6279 | S100A8 | 4319 | MMP10 |
| 26585 | GREM1 | 9241 | NOG |
| 9510 | ADAMTS1 | 8483 | CILP |
| 29949 | IL19 | 26525 | IL36RN |
| 1508 | CTSB | 5079 | PAX5 |
| 91543 | RSAD2 | 3624 | INHBA |
| 4049 | LTA | 3569 | IL6 |
| 1435 | CSF1 | 2254 | FGF9 |
| 4938 | OAS1 | 51561 | IL23A |
| 3662 | IRF4 | 3456 | IFNB1 |
| 1437 | CSF2 | 60 | ACTB |
| 3557 | IL1RN | | |

Pathotype-Specific Eigengene Scores Predict Immunohistochemistry (IHC)-Determined Pathotypes Eigengene scores were calculated as previously described (see, e.g., Bueno et al., Nature Genetics. 48(4):407-16, 2016, which is herein incorporated by reference in its entirety).

Gene expression values were collapsed to a single score per sample. A positive correlation was observed between synovial histological grade and the lymphoid or myeloid eigengene scores and, in contrast, a negative correlation between the pauciimune fibroid eigengene score and synovial histological grade (FIG. 2D). A machine learning technique, k-nearest neighbors, was utilized to develop a predictor of IHC-determined pathotype using the pathotype-specific eigengenes. A five-fold cross-validation methodology predicted the IHC pathotype with 64% accuracy (kappa=0.44). In general, the lymphoid pathotype was more readily predicted than myeloid or pauciimmune-fibroid, with most misclassifications occurring between pauciimmune-fibroid and myeloid. This suggests that while molecular phenotyping can approximate the IHC pathotype, each technique yields complementary information about the samples.

Figure 3B:
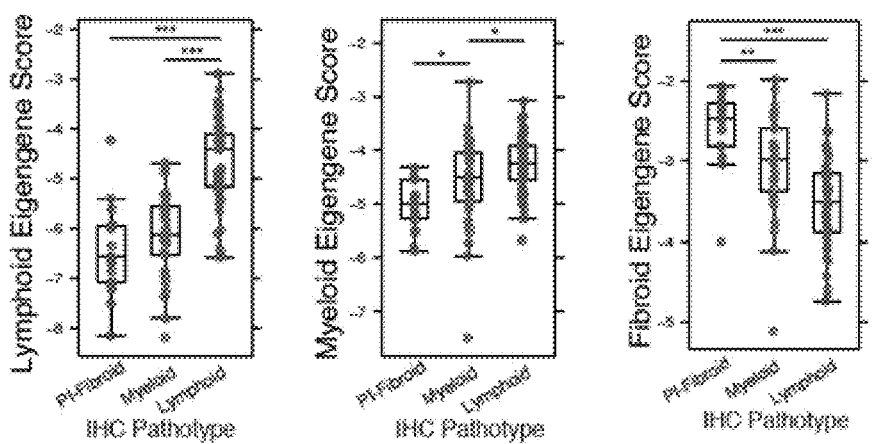
FIG. 3B is a series of plots showing eigengene scores versus IHC-determined pathotypes. Individual eigengene scores are plotted for each sample, grouped and colored by the pathotype as determined by IHC. Asterisks represent statistical significance as determined by linear regression across groups: *=p<0.05; =p<0.01; and *=p<0.001.
Figure 3C:
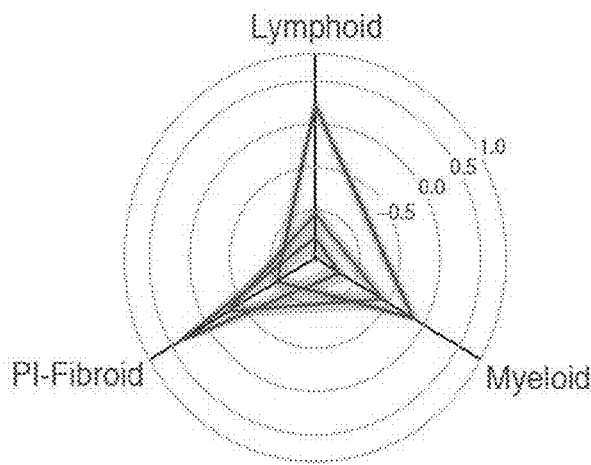
FIG. 3C is a radar plot of standardized eigengene scores. Eigengene values were normalized to give a mean of 0 and standard deviation of 1. Samples were grouped by pathotype, and the mean (solid lines) and standard error of the mean (shaded region) was calculated for the normalized eigengenes. Spokes of the radar plot represent the distance along each normalized eigengene for each sample group.
Figure 3D:
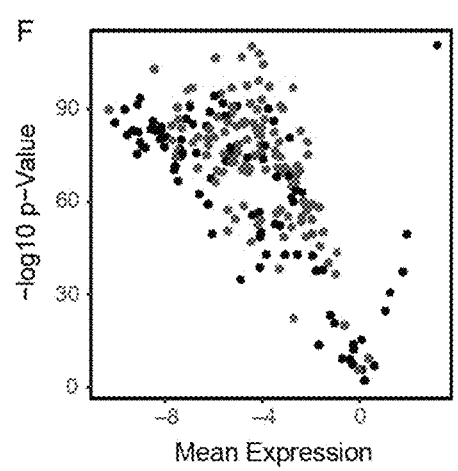
FIG. 3D is a volcano plot of gene expression differences across pathotypes. For each gene, a 1-way ANOVA was performed comparing expression across the three pathotypes. The $-\log_{10}$ p-value from the 1-way ANOVA is plotted against the root mean square of the $\log_2$-fold changes between each pair of eigengenes. Genes are colored according to the pathotype in which it was initially identified, with RA biology-associated genes colored black.

Unsupervised clustering of the NANOSTRING® expression data showed strong grouping of pathotype-defined genes in concordance with their initial pathotype assigned by histology (FIG. 3A). Samples classified as either lymphoid or pauciimmune-fibroid showed highest expression of the lymphoid or pauciimmune-fibroid eigengene score, respectively (FIG. 3B). Samples classified as myeloid had intermediate levels of the myeloid eigengene score, with higher expression than pauciimmune-fibroid samples, but lower expression than lymphoid samples (FIGS. 3B and 3C). Further, the use of a 1-way ANOVA to compare gene expression across the pathotypes revealed that almost every gene measured differed significantly across the three groups; all but 1 of 212 genes had an adjusted p-value<0.01 (FIG. 3D).

Figure 4A:
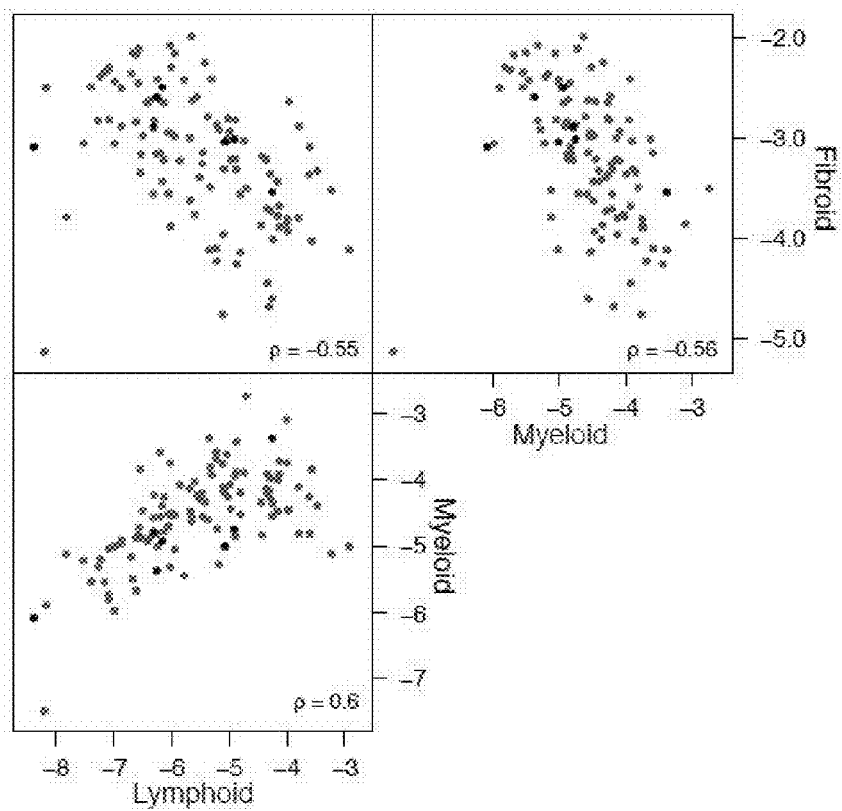
FIG. 4A is a series of plots comparing eigengene scores. Eigengene values for baseline samples are plotted against each other, with samples colored according to IHC-determined pathotype.
Figure 4B:
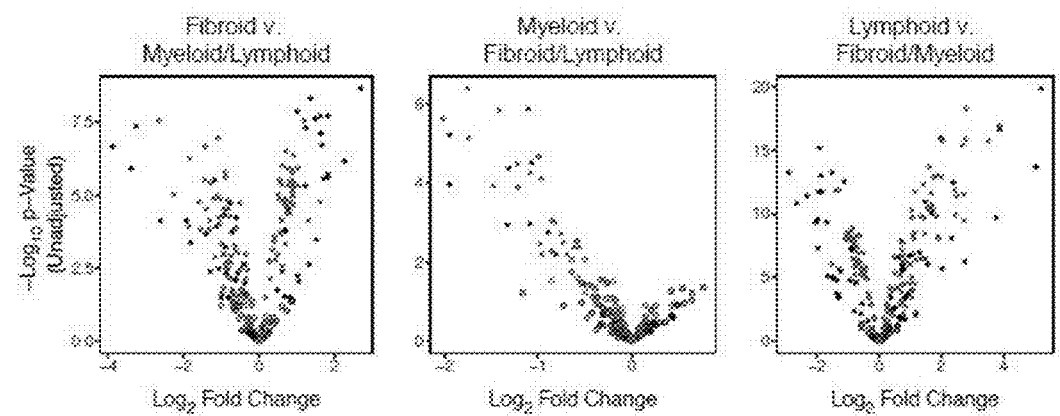
FIG. 4B is a series of volcano plots showing comparisons between the three pathotypes. Each pathotype was compared to the other two using linear regression. The $\log_2$-fold change and $-\log_{10}$ p-values for these comparisons are shown, with genes colored according to the pathotype to which they were initially assigned and RA biology-associated genes colored black. Genes that were significant at a Benjamini-Hochberg adjusted p-value<0.01 are shown as filled dots, while those not meeting this cutoff are shown as open circles.

Pauciimmune-fibroid eigengene scores were inversely correlated with lymphoid and myeloid eigengene scores, while lymphoid and myeloid eigengene scores were positively correlated with each other (FIG. 4A). Comparing myeloid pathotype samples to either lymphoid or pauciimune-fibroid pathotype samples yielded fewer differentially expressed genes, with lower expression of lymphoid-specific genes in these samples relative to the combined lymphoid/pauciimmune-fibroid group (FIG. 4B). This is consistent with the scoring algorithm used to determine the pathotypes: myeloid samples mainly differ from lymphoid samples by a relative lack of B cell staining.

Taken together, these data demonstrate that the pathotype-specific gene sets show strong association with the matched clinically and immunohistochemically determined pathotype.

Figures 5A, 5B:
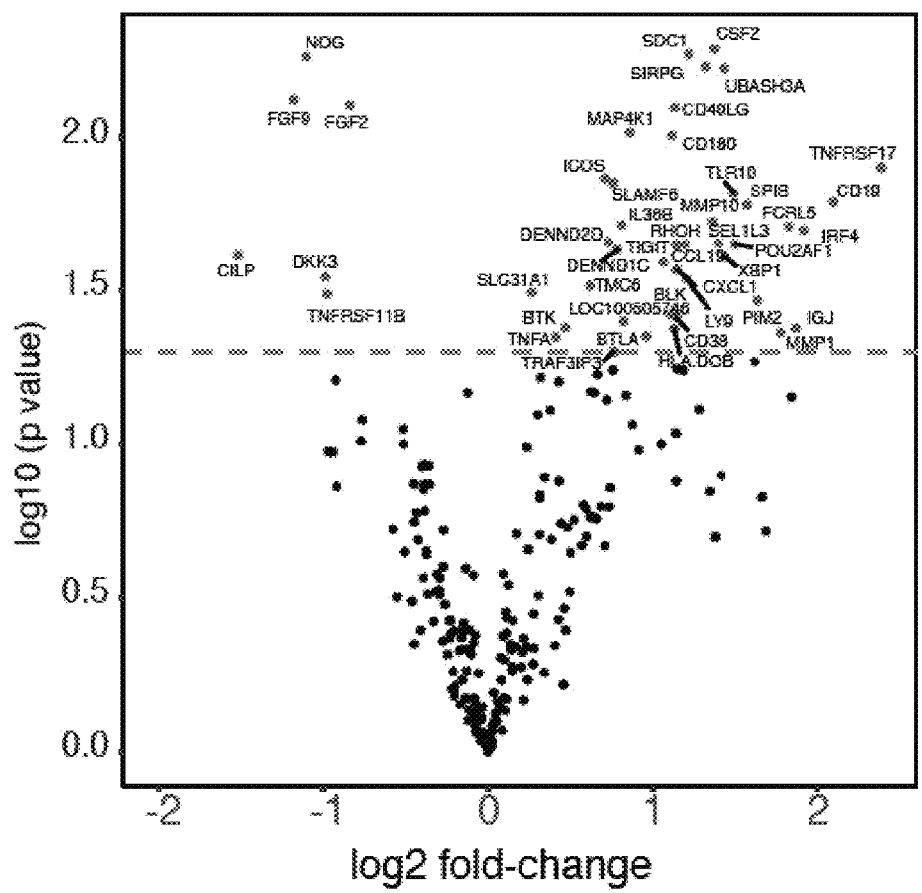
FIG. 5A is a table showing 12-month radiographic outcome of individuals stratified according to pauciimmune-fibroid/myeloid versus lymphoid pathotypes.
FIG. 5B is a volcano plot of pre-treatment genes differentially expressed in individuals who progress radiographically after one year (ShSS 1). P-values were from the two-sample t-test comparing the progressors and non-progressors without adjustment. 46 genes with a p-value<0.05 are highlighted in red and located above the dashed line.

Example 2. Association Between Pathotype, Gene Expression Levels, Clinical Covariates, Disease Activity, and Disease Progression of Individuals Having RA Synovial pathotype and gene expression levels were evaluated for their association with clinical covariates to determine whether they were predictive of disease activity and/or progression in individuals having RA.
Synovial Pathotype and Gene Expression Predict Radiographic Progression Baseline pathotypes or gene expression were assessed for association with ongoing structural damage as measured by the Sharp-van der Heijde radiographic progression scores (ShSS) at 12 months after initial biopsy. Although baseline pathotype was not predictive of 12-month erosion or joint space narrowing, lymphoid individuals showed a significantly higher increase in ShSS and had greater risk of progressive disease (>1 ΔShSS) relative to myeloid and pauciimmune-fibroid individuals (FIG. 5A). Importantly, of the 16 individuals subsequently commenced on biologic therapy between 6 and 12 months of follow-up, a higher proportion fell within the lymphoid (22.8%, 8/35) compared to the myeloid/pauciimmune-fibroid (13.8%, 8/58) groups (Fishers exact test, p=0.27). Thus, despite more intensive treatment regimens (including higher rates of biologic therapeutic agent use), individuals with a lymphoid pathotype were significantly more likely to develop joint damage progression.

Figure 5C:
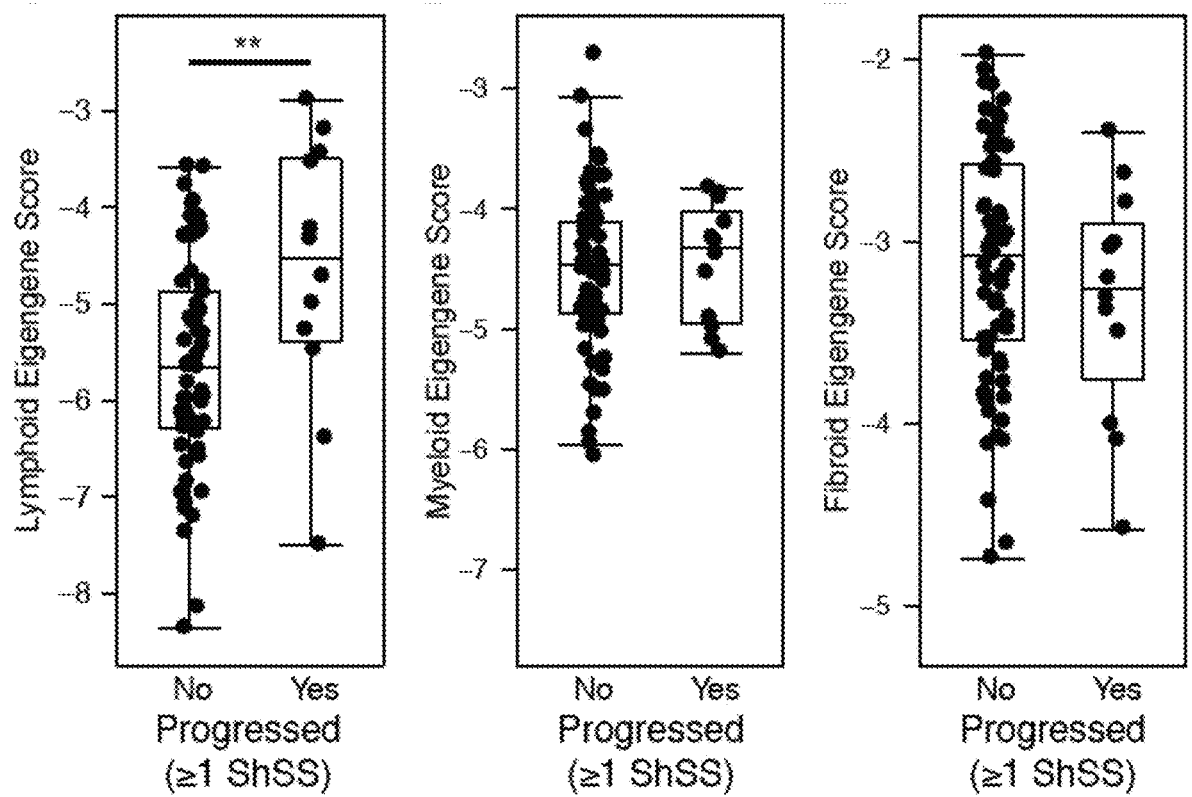
FIG. 5C is a series of plots showing lymphoid (left panel), myeloid (center panel), and pauciimmune-fibroid (right panel) baseline scores against radiographic progression status (ΔShSS≥1) at one year. **=p<0.01 by t-test.
Figure 5D:
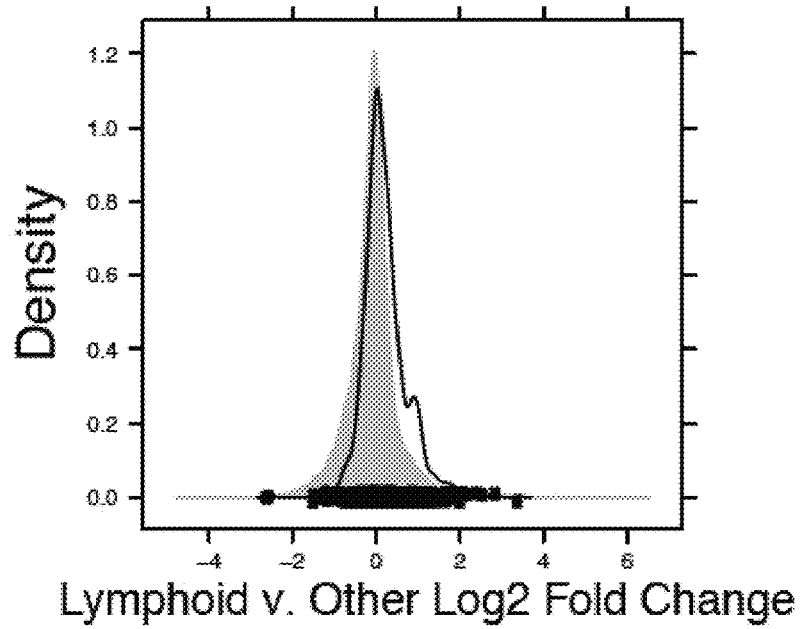
FIG. 5D is a gene set enrichment plot showing that osteoclast-specific genes are more highly expressed in the lymphoid pathotype versus fibroid/myeloid pathotypes. The x-axis shows the log 2 fold change between lymphoid and fibroid/myeloid samples. The density shown in grey shows the distribution of fold changes across all genes assayed; osteoclast-specific genes are shown as black points, with the overall distribution of fold changes shown as a black line.

To examine the genes associated with subsequent radiographic progression, ShSS progressors and non-progressors were compared for pre-treatment gene expression (FIG. 5B). 46 genes with a p-value<0.05 were identified, including the B cell-associated genes CD19, FCRL5, and BCMA. A complete list of these genes is found in Table 1. The pre-treatment lymphoid eigengene score was significantly elevated in individuals who had a 12-month elevation in ShSS score compared to those who did not (FIG. 5C). In contrast, the myeloid and pauciimmune-fibroid eigengene scores were not elevated in progressors compared to non-progressors (FIG. 5C). Further, a gene set previously defined as being expressed in osteoclasts (from a dataset in the Harmonizome database) were most highly expressed in lymphoid patients versus myeloid and fibroid patients. The overall osteoclast gene set was significantly enriched in lymphoid patients versus the others (FIG. 5D), suggesting that the bone resorption mechanism and high B cell infiltration are concurrent in these patients, perhaps as a result of very favorable conditions for osteoclastogenesis in the synovial lining. In contrast, non-progressors had elevated levels at baseline of pauciimmune-fibroid-associated genes including FGF family members (e.g., Noggin) and cartilage intermediate layer protein. Additionally, osteoprotegrin, a decoy receptor for receptor activator of nuclear factor kappa-B ligand (RANKL), and therefore a negative regulator of osteoclastogenesis, was also elevated in non-progressors.

To determine whether baseline clinical and gene expression data could be combined into a model for predicting radiographic progression, two complementary approaches were employed: (1) a logistic regression coupled with backward model selection to identify a minimal set of clinical predictors, and (2) a penalized method based on logistic regression, performed using the glm procedure from the stats package of R, with an L1 regularization penalty (LASSO) to identify genes that improve the clinical model.

Figure 5E:
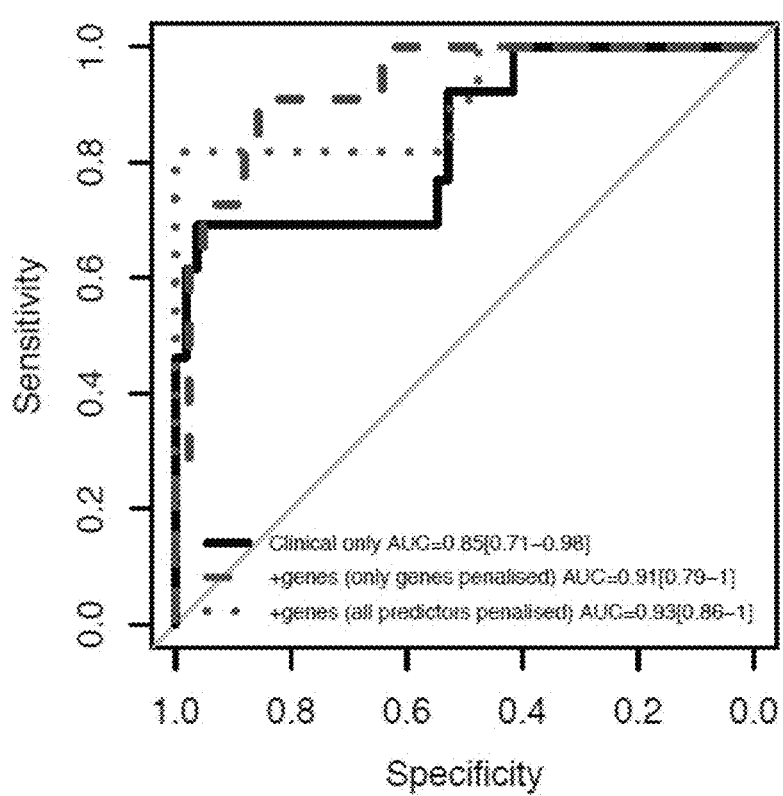
FIG. 5E is a ROC graph showing the identification of clinical and gene expression features predictive of radiographic progression at one year. The 46 genes as listed in Table 1 and selected covariates (eight clinical covariates: baseline RF titer, disease duration, VAS, swollen joint number, DAS28-ESR, baseline pathotype, and 12 max ultrasound synovial thickening (USST) and ultrasound power Doppler (USPD) scores) were entered simultaneously into a logistic model with an L1 regularization penalty (LASSO) in order to determine the optimal sparse prediction model. The model exhibited improved predictive performance with penalized clinical covariates (blue dashed line) compared to without penalizing clinical covariates (red dotted line), and both these models outperform just the clinical measures alone (black line).

Logistic regression, coupled with backward stepwise model selection was applied to baseline clinical parameters against a dependent variable of radiographic progression at 12 months to select which clinical covariate contributed the most to the prediction; 16 baseline clinical covariates were considered as candidates in the regression model. Baseline variables included gender, age, disease duration, ESR, CRP, RF titer, ACPA titer (as continuous variables), VAS, tender and swollen joint number, baseline DAS28-ESR, EULAR response at 6 months (categorical), baseline HAQ, 12 max USST and USPD scores, and baseline pathotype (two categories: Lymphoid v. Pauciimmune-fibroid/Myeloid). Stepwise variable selection yielded a model with 8 clinical variables: baseline RF titer, disease duration, VAS, swollen joint number, DAS28-ESR, baseline pathotype, and 12 max USST and USPD scores. Next, LASSO was applied on these eight clinical covariates and 46 genes identified as being significantly differentially expressed between progressors and non-progressors in order to determine the optimal sparse prediction model. The predictive performance of the models with the genes alone, with the clinical covariates alone, and with the combination of genes and clinical covariates was assessed by computing the area under the receiver operating characteristic curve (AUC). The AUC represents the probability that for any randomly selected pair of individuals with and without a radiographic progression, the individual who had a radiographic progression had a higher predicted risk. A value of 0.50 represents no discrimination, and 1 represents perfect discrimination. Both apparent and internal validations were assessed. The apparent predictive performance of the model evaluated by area under curve (AUC) was 0.85 (95% CI: 0.71-0.98) for clinical covariates alone and 0.91 (% CI CI: 0.79-1.0) for the genes alone (FIG. 5E).

Figures 6A, 6B:
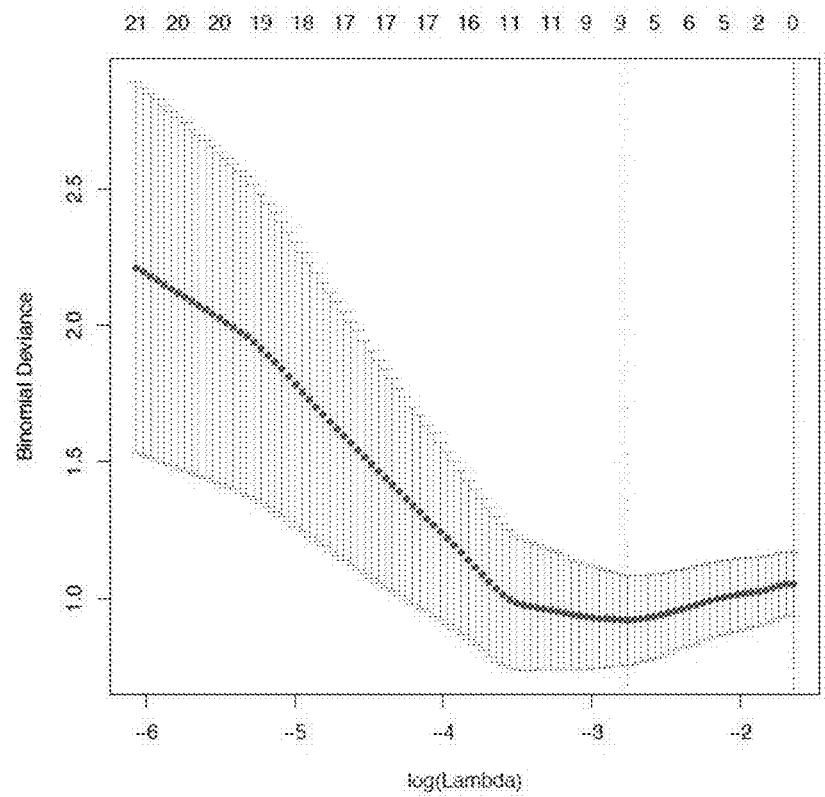
FIG. 6A is a lambda training curve from the final glmnet fitted model. The red dots represent mean binomial deviance using 10-fold cross-validation. The error bars represent standard error of binomial deviance. The vertical dotted lines indicate minimum binomial deviance ($\lambda_{min}$) and a more regularized model for which the binomial deviance error is within one standard error of the minimum binomial deviance ($\lambda_{1se}$). $\lambda_{min}$ was selected, corresponding to nine non-zero coefficients in the final model.
FIG. 6B is a table showing the non-zero coefficients associated with the final variables selected by the LASSO regression.

A model incorporating RF titer and the expression of seven genes (CD180, CSF2, CXCL1, DENND1C, MMP10, SDC1, and UBASH3A) included in Table 2, yielded a predictor of progression with a lambda ratio of 0.0631 (FIG. 6A). This model resulted in an improved apparent prediction performance of the model (AUC 0.93, 95% CI: 0.86-1; FIGS. 5E and 6B). Bootstrap resampling was performed to correct the AUC for potential over-fitting. To perform the bootstrap, a random sample was drawn with replacement from the original sample. First, the model was trained on the bootstrap sample, validated on the original sample, and an AUC statistic was computed. Next, the model was trained and validated on the same bootstrap sample and another AUC statistic was computed. The difference between the two AUC was computed, and the procedure was repeated 500 times. The 500 differences were then averaged to give an estimate of the optimism. The optimism corrected estimate of the AUC was calculated as the apparent AUC minus the estimated optimism. The optimism-corrected AUC was 0.85 for the pure clinical model, 0.91 for the pure gene expression model, and 0.93 for the combined clinical and gene expression model, suggesting that while examining the expression of genes or clinical covariates alone results in a reliable prognostic model, including both clinical covariates and genes (e.g., CD180, CSF2, CXCL1, DENND1C, MMP10, SDC1, and UBASH3A) in the model resulted in a prognostic model with improved discrimination between individuals with and without radiographic progression compared to a prognostic model that only considered clinical covariates or gene expression alone.

Figures 7A, 7B:
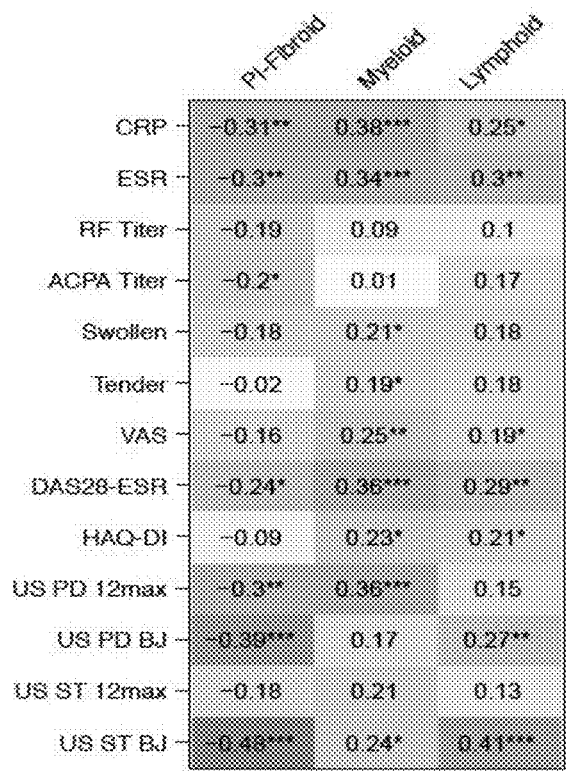
FIG. 7A is a table showing baseline clinical and histological parameters stratified according to the three pathological subtypes (n=129). Asterisks indicates significant differences.
FIG. 7B is a chart showing the correlation analysis of each eigengene score with metrics of clinical disease activity, autoantibodies, acute phase reactants, and ultrasonography. Values represent Spearman correlation coefficients between the clinical variables and the individual eigengene scores. Asterisks represent the significance of the correlation coefficient: *=p<0.05; =p<0.01; and *=p<0.001

Synovial Lymphoid Pathotype and Myeloid Gene Expression Score Correlate with Overall RA Disease Activity Baseline disease activity characteristics across the synovial pathotypes were compared with no significant differences identified in age or disease duration across the groups (FIG. 7A). However, the lymphoid pathotype had the highest levels of ESR, CRP, ACPA titer, swollen joint counts, and DAS28-ESR scores. Assessment of joint damage by X-ray indicated a trend for more severe joint space narrowing in the lymphoid group. Further, ultrasonographic assessment indicated that the lymphoid group had significantly higher levels of synovial thickening and Power Doppler (PD) scores (both within the biopsied joint and overall PD scores), indicating presence of synovitis and supporting the clinical association with active disease. In contrast, the pauciimmune-fibroid group had the lowest levels of acute phase reactants, RF and ACPA positivity, and PD ultrasound scores, despite the presence of active disease, as determined clinically by elevation of DAS28-ESR, swollen joint counts, HAQ and VAS scores, and synovitis determined by ultrasonography.

The expression of each eigengene score was compared to clinical covariates of disease activity, including DAS28-ESR score, ESR, CRP, swollen and tender joint counts, visual analog scale, HAQ DI score, and ultrasonography, both at the biopsied joint and overall, using Spearman's rank sum correlation method (FIG. 7B). The myeloid eigengene score was highly associated with many aspects of disease severity, including ESR and CRP, joint counts, DAS28-ESR score, HAQ DI score, and overall PD ultrasonography score. The lymphoid eigengene score was also correlated with many of these, but at a lower level, and was more associated with ultrasonography (both Power Doppler and synovial thickening measures) at the biopsied joint. As expected based on gene expression correlations, the pauciimmune-fibroid eigengene score was negatively associated with many aspects of disease activity.

Together, these data show that the baseline pathotype or gene expression levels alone, or in combination with clinical covariates, can serve as a prognostic biomarker that is predictive of disease progression in an individual having RA. Consequently, evaluation of baseline pathotype and gene expression levels alone, or in combination with clinical covariates, can be used to identify individuals having RA who may benefit from a treatment including a therapeutic agent (e.g., a biologic therapeutic agent) other than, or in addition to, a DMARD. These results also suggest that the overall disease activity in an individual is most closely related to the expression of myeloid-associated genes in the joint, while elevation of pauciimmune-fibroid genes is associated with lower disease severity across a range of disease activity parameters.

Example 3. Association Between Myeloid and Lymphoid Eigengene Scores and Response to DMARD Therapy As discussed in Example 2, pathotype-specific eigengene scores correlated with disease activity and progression. Pathotype-specific eigengene scores were further evaluated for their association with responsiveness of an individual to DMARD therapy, and to determine whether they could serve as biomarkers to predict and/or monitor responsiveness to DMARD therapy.

Pre-Treatment Pathotypes and Gene Expression Levels Association with Response to DMARD Treatment Individuals in the three distinct histologically-determined pathotypes were compared for their response to DMARD therapy, as determined by a change in DAS28-ESR at six months and the EULAR response criteria. No significant association of baseline pathotype status with therapeutic outcome was observed, although it was notable that the myeloid and lymphoid pathotype individuals were treated more often with a combination of methotrexate and other DMARDs (FIG. 8A), consistent with the treat-to-target approach used for individuals with more aggressive disease. Examination of gene expression differences between baseline and six months in individuals who achieved a EULAR good response indicated that multiple inflammatory pathways were reduced, including genes associated with lymphoid aggregates (e.g., CCL19, BTLA, IL21R, CXCL13, LTA, and LTB) and inflammatory cytokines (e.g., IL6) (FIG. 8B). In contrast, individuals who did not respond showed smaller decreases in inflammatory gene expression (FIG. 8C), indicative of persistent synovitis.

Figure 8D:
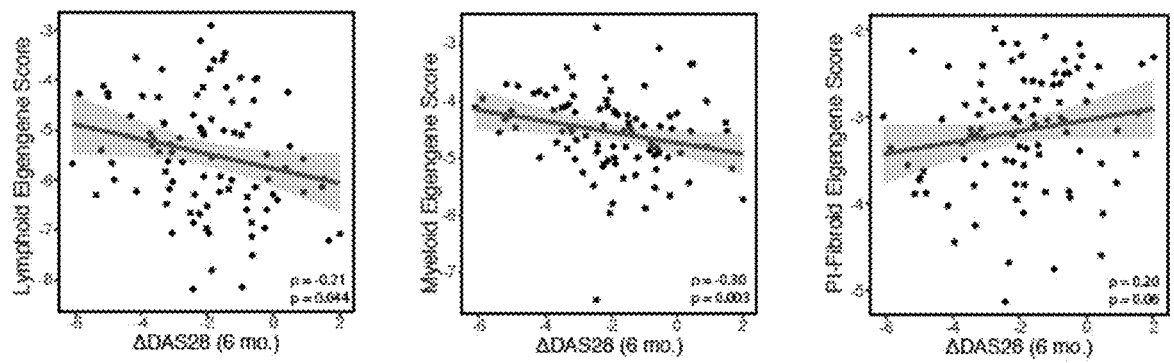
FIG. 8D is a series of plots showing correlation of pre-treatment lymphoid (left panel), myeloid (center panel), and pauciimmune-fibroid (right panel) eigengene scores with change in DAS28-ESR after six months of DMARD treatment. Spearman's correlation coefficient is shown, along with the significance of this value.

Eigengene scores at baseline were then assessed for associations with therapeutic outcome following DMARD therapy. Higher myeloid and lymphoid eigengene expression (but not pauciimmune-fibroid) were associated with larger decreases in DAS28-ESR scores post-treatment (Spearman's rho=−0.3 (M), p=0.003; rho=−0.21 (L), p=0.044; FIG. 8D).

Figure 8E:
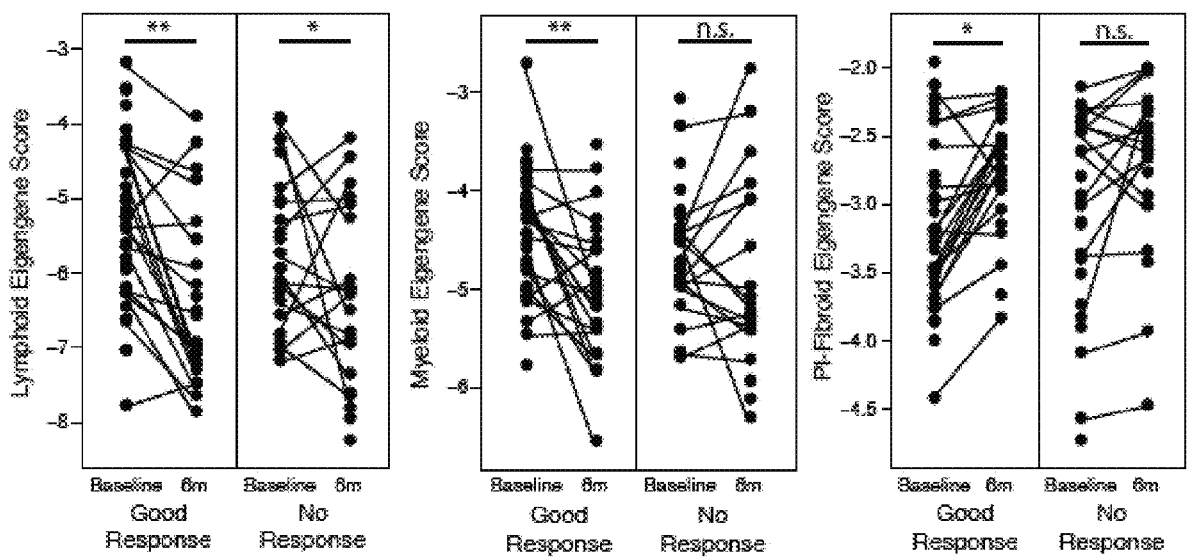
FIG. 8E is a series of paired plots for baseline and six-month lymphoid (left panels), myeloid (center panels), and pauciimmune-fibroid (right panels) eigengene scores in individuals who achieved good or poor clinical responses to DMARD treatment at six months by the EULAR response criteria. Individuals who achieved a good response, or failed to achieve a moderate response, according to EULAR criteria are shown. For each individual, the pre-treatment eigengene scores are connected to the post-treatment eigengene score, for each of the three eigengenes. Asterisks represent significance of the difference between pre- and post-treatment samples using a linear mixed effects model with sample date as a fixed effect and individual as a random effect: *=p<0.05; =p<0.01; and *=p<0.001.

To determine if pathotype eigengene scores were affected by DMARD therapy, baseline and six-month samples were compared separately for individuals that achieved a good response and those that did not respond to DMARD therapy. Individuals that showed a good response to DMARD therapy had very dynamic gene expression, with significant decreases in both lymphoid and myeloid eigengene scores, and a concomitant increase in pauciimmune-fibroid eigengene scores (FIG. 8E). Non-responders exhibited a more muted change in gene expression, with significant decrease in lymphoid eigengene score, but highly variable changes in myeloid and pauciimmune-fibroid eigengene score (FIG. 8E).

Together, these data show that a myeloid eigengene score can serve as a predictive biomarker that is predictive of therapeutic efficacy of a treatment including a DMARD, alone or in combination with a lymphoid eigengene score. Therefore, evaluation of eigengene scores can be used, for example, to identify individuals having RA who may benefit from a treatment including a DMARD, as well as in monitoring the response to a treatment including a DMARD. These results also indicate an ongoing presence of myeloid gene expression in individuals with continuing disease activity despite DMARD therapy.

Example 4. Association Between Serum Gene Expression Levels and Synovial Pathology Circulating serum biomarkers, hypothesized from overexpression in synovial subsets of disease (Dennis et al. *Arthritis Research and Therapy.* 16(2): R90, 2014) were assessed for their potential to serve as reliable measures of disease activity in the PEAC cohort.

Serum Biomarkers Reflect Synovial Pathophysiology

Figure 9A:
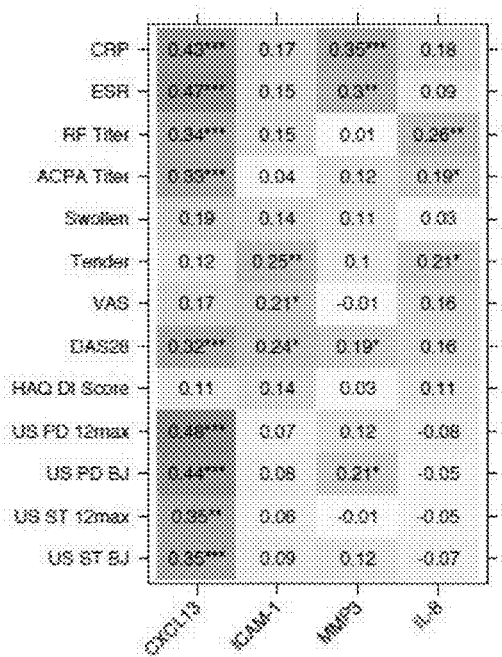
FIG. 9A is a chart showing the correlation of pre-treatment serum CXCL13, sICAM1, MMP3, and IL-8 with clinical disease metrics and ultrasonography scores. Values represent Spearman correlation coefficients between the clinical variables and the individual eigengene scores. Asterisks represent the significance of the correlation coefficient: *=p<0.05; =p<0.01; and *=p<0.001.
Figure 9B:
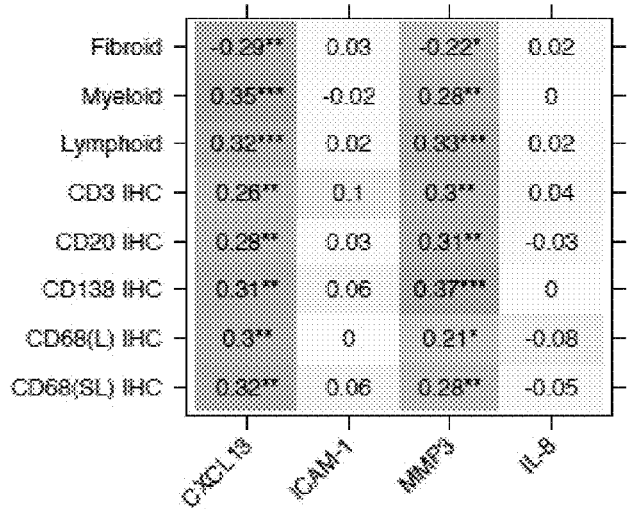
FIG. 9B is a chart showing the correlation of pre-treatment serum CXCL13, sICAM1, MMP3, and IL-8 with synovial histology scores. Values represent Spearman correlation coefficients between the clinical variables and the individual eigengene scores. Asterisks represent the significance of the correlation coefficient: *=p<0.05; =p<0.01; and *=p<0.001.
Figure 9C:
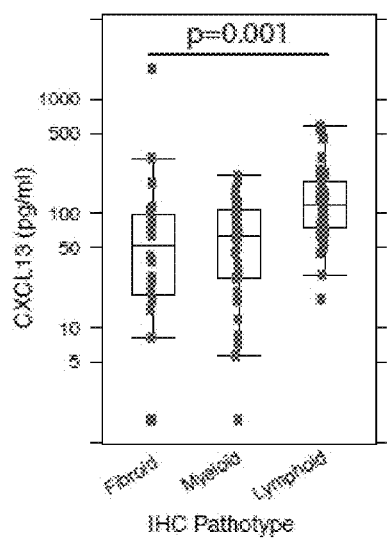
FIG. 9C is a plot of the concentration of serum CXCL13 versus synovial pathotype status, showing elevated levels in lymphoid pathotypes versus myeloid or pauciimmune-fibroid. P-values were calculated using a t-test.
Figure 9D:
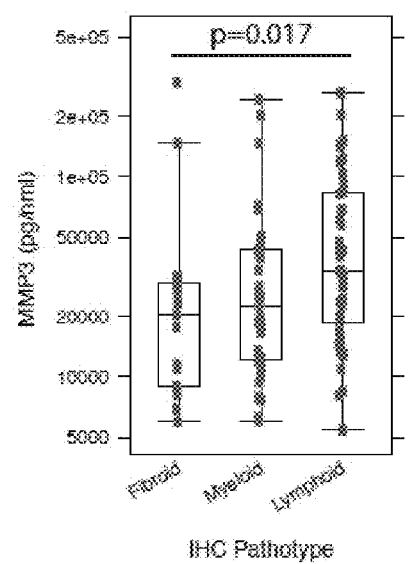
FIG. 9D is a plot of the concentration of serum MMP3 versus synovial pathotype status, showing elevated levels in lymphoid pathotypes versus myeloid or pauciimmune-fibroid. P-values were calculated using a t-test.

Serum samples from 111 individuals at baseline were assessed for levels of soluble intercellular adhesion molecule 1 (sICAM1), C—X—C motif chemokine 13 (CXCL13), interleukin 8 (IL-8), and matrix metalloproteinase-3 (MMP3) using customized electrochemiluminescence assays incorporating sample diluent blocking reagents to minimize interference from heterophilic antibodies. Serum CXCL13 correlated with global disease metrics, including DAS28 score, serological and ultrasonographic measures of disease activity, and synovial histology (FIGS. 9A and 9B). Serum MMP-3 also showed modest yet significant correlation with acute phase reactants and DAS score, as well as synovial histology (FIGS. 9A and 9B). Notably, CXCL13 and MMP3 were both elevated in individuals with a lymphoid pathotype, compared to the other two pathotypes (FIGS. 9C and 9D). In contrast, sICAM1 and IL-8 exhibited modest and variable correlations with clinical indices, such as tender joint scores, acute phase reactants, auto-antibody titers, and tender joint scores (FIGS. 9A and 9B), despite previous reports of elevation in RA individuals (Dennis et al. *Arthritis Research and Therapy.* 16(2): R90, 2014; Cascao et al. *Arthritis Research & Therapy.* 12(5): R196, 2010.

In summary, these data demonstrate that elevation of some, but not all, inflammatory proteins in the serum of RA correlates with synovitis and clinical disease activity.

VI. Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of identifying an individual having rheumatoid arthritis (RA) as one who is more likely to exhibit disease progression of RA when treated with a disease modifying anti-rheumatic drug (DMARD) and treating the individual, the method comprising:
   (i) determining an expression level of CD180, CSF2, CXCL1, DENND1C, MMP10, SDC1, and UBASH3A in a sample from the individual, wherein the individual has an increased expression level of CD180, CSF2, CXCL1, DENND1C, MMP10, SDC1, and UBASH3A relative to a reference expression level, thereby identifying the individual as one who is more likely to exhibit disease progression when treated with a DMARD; and
   (ii) administering a therapeutic agent other than a DMARD to the individual who has been identified as one who is more likely to exhibit disease progression.

2. A method of treating an individual having RA, the individual being identified as having an increased expression level of CD180, CSF2, CXCL1, DENND1C, MMP10, SDC1, and UBASH3A in a sample from the individual relative to a reference expression level, the method comprising administering to the individual a therapeutic agent other than a DMARD.

3. The method of claim 2, wherein the expression level of CD180, CSF2, CXCL1, DENND1C, MMP10, SDC1, and UBASH3A is (a) an average of the expression levels of CD180, CSF2, CXCL1, DENND1C, MMP10, SDC1, and UBASH3A or (b) a median of the expression levels of CD180, CSF2, CXCL1, DENND1C, MMP10, SDC1, and UBASH3A.

4. The method of claim 3, wherein the average of the expression levels of CD180, CSF2, CXCL1, DENND1C, MMP10, SDC1, and UBASH3A is an average of the normalized expression levels of CD180, CSF2, CXCL1, DENND1C, MMP10, SDC1, and UBASH3A or the median of the expression levels of CD180, CSF2, CXCL1, DENND1C, MMP10, SDC1, and UBASH3A is a median of the normalized expression levels of CD180, CSF2, CXCL1, DENND1C, MMP10, SDC1, and UBASH3A.

5. The method of claim 4, wherein the normalized expression levels of CD180, CSF2, CXCL1, DENND1C, MMP10, SDC1, and UBASH3 are the expression levels of CD180, CSF2, CXCL1, DENND1C, MMP10, SDC1, and UBASH3A normalized to a reference gene.

6. The method of claim 5, wherein the reference gene is ACTB, GAPDH, GUSB, HPRT1, PGK1, RPL19, TUBB, TMEM55B, or a combination thereof.

7. The method of claim 2, wherein the reference expression level is a pre-assigned expression level of CD180, CSF2, CXCL1, DENND1C, MMP10, SDC1, and UBASH3A.

8. The method of claim 2, wherein the reference expression level is the expression level of CD180, CSF2, CXCL1, DENND1C, MMP10, SDC1, and UBASH3A in a reference population of individuals having RA who have not previously been treated with a DMARD, the reference population of individuals consisting of a first subset of individuals who exhibited disease progression and a second subset of individuals who did not exhibit disease progression, wherein the reference expression level significantly separates the first and second subsets of individuals based on a significant difference between the expression level of CD180, CSF2, CXCL1, DENND1C, MMP10, SDC1, and UBASH3A in the first subset of individuals compared to that of the second subset of individuals.

9. The method of claim 8, wherein the first subset of individuals exhibited disease progression and the second subset of individuals did not exhibit disease progression after about 12 months.

10. The method of claim 2, further comprising determining one or more clinical covariates of the individual.

11. The method of claim 10, wherein the one or more clinical covariates are one or more of: disease activity score 28-erythrocyte sedimentation rate (DAS28-ESR), disease activity score 28-C reactive protein (DAS28-CRP), rheumatoid factor (RF) titer, disease duration, baseline pathotype, and 12max ultrasound synovial thickening (USST) and ultrasound power Doppler (USPD) scores.

12. The method of claim 2, wherein the expression level is a nucleic acid expression level.

13. The method of claim 12, wherein the nucleic acid expression level is an mRNA expression level.

14. The method of claim 2, wherein the expression level is a protein expression level.

15. The method of claim 2, wherein the sample is a synovial sample.

16. The method of claim 2, wherein the DMARD is methotrexate, hydroxychloroquine, sulfasalazine, leflunomide, azathioprine, cyclophosphamide, cyclosporine, mycophenolate mofetil, or a combination thereof.

17. The method of claim 2, wherein the therapeutic agent other than a DMARD is a B cell antagonist, a Janus kinase (JAK) antagonist, a tumor necrosis factor (TNF) antagonist, a decoy TNF receptor, a T cell costimulatory signal antagonist, an IL-1 receptor antagonist, an IL-6 receptor antagonist, or a combination thereof.

\* \* \* \* \*

SEQUENCE LISTING

```
<160> NUMBER OF SEQ ID NOS: 30

<210> SEQ ID NO 1
<211> LENGTH: 2725
<212> TYPE: DNA
<213> ORGANISM: Homo sapiens

<400> SEQUENCE: 1
agaatgctga gcagtcaaca gcatttcttg ttccaagatc acccttctga gtacctctct      60
ggctgccaaa ttgccagggc cttcacagtt tgattccatt tctcagctcc aagcattagg     120
taaacccacc aagcaatcct agcctgtgat ggcgtttgac gtcagctgct tcttttgggt     180
ggtgctgttt tctgccggct gtaaagtcat cacctcctgg gatcagatgt gcattgagaa     240
agaagccaac aaaacatata actgtgaaaa tttaggtctc agtgaaatcc ctgacactct     300
accaaacaca acagaatttt tggaattcag ctttaatttt ttgcctacaa ttcacaatag     360
aaccttcagc agactcatga atcttacctt tttggattta actaggtgcc agattaactg     420
gatacatgaa gacactttc aaagccatca tcaattaagc acacttgtgt taactggaaa     480
tcccctgata ttcatggcag aaacatcgct taatgggccc aagtcactga agcatctttt     540
cttaatccaa acgggaatat ccaatctcga gtttattcca gtgcacaatc tggaaaactt     600
ggaaagcttg tatcttggaa gcaaccatat ttcctccatt aagttcccca aagacttccc     660
agcacggaat ctgaaagtac tggattttca gaataatgct atacactaca tctctagaga     720
agacatgagg tctctggagc aggccatcaa cctaagcctg aacttcaatg gcaataatgt     780
taaaggtatt gagcttgggg cttttgattc aacgatcttc caaagtttga actttggagg     840
aactccaaat ttgtctgtta tattcaatgg tctgcagaac tctactactc agtctctctg     900
gctgggaaca tttgaggaca ttgatgacga agatattagt tcagccatgc tcaagggact     960
ctgtgaaatg tctgttgaga gcctcaacct gcaggaacac cgcttctctg acatctcatc    1020
caccacattt cagtgcttca cccaactcca agaattggat ctgacagcaa ctcacttgaa    1080
agggttaccc tctgggatga agggtctgaa cttgctcaag aaattagttc tcagtgtaaa    1140
tcatttcgat caattgtgtc aaatcagtgc tgccaatttc ccctccctta cacacctcta    1200
catcagaggc aacgtgaaga aacttcacct tggtgttggc tgcttggaga aactaggaaa    1260
ccttcagaca cttgatttaa gccataatga catagaggct tctgactgct gcagtctgca    1320
actcaaaaac ctgtcccact tgcaaacctt aaacctgagc cacaatgagc ctcttggtct    1380
ccagagtcag gcattcaaag aatgtcctca gctagaactc ctcgatttgg catttaccg    1440
```

```
cttacacatt aatgctccac aaagtcccct ccaaaacctc catttccttc aggttctgaa    1500
tctcacttac tgcttccttg ataccagcaa tcagcatctt ctagcaggcc taccagttct    1560
ccggcatctc aacttaaaag ggaatcactt tcaagatggg actatcacga agaccaacct    1620
acttcagacc gtgggcagct tggaggttct gattttgtcc tcttgtggtc tcctctctat    1680
agaccagcaa gcattccaca gcttgggaaa aatgagccat gtagacttaa gccacaacag    1740
cctgacatgc gacagcattg attctcttag ccatcttaag ggaatctacc tcaatctggc    1800
tgccaacagc attaacatca tctcaccccg tctcctccct atcttgtccc agcagagcac    1860
cattaattta agtcataacc ccctggactg cacttgctcg aatattcatt tcttaacatg    1920
gtacaaagaa aacctgcaca aacttgaagg ctcggaggag accacgtgtg caaacccgcc    1980
atctctaagg ggagttaagc tatctgatgt caagctttcc tgtgggatta cagccatagg    2040
catttccttt ctcatagtat ttctattatt gttggctatt ctgctatttt ttgcagttaa    2100
ataccttctc aggtggaaat accaacacat ttagtgctga aggtttccag agaaagcaaa    2160
taagtgtgct tagcaaaatt gctctaagtg aaagaactgt catctgctgg tgaccagacc    2220
agactttcca gattgcttcc tggaactggg cagggactca ctgtgctttt ctgagcttct    2280
tactcctgtg agtcccagag ctaaagaacc ttctaggcaa gtacaccgaa tgactcagtc    2340
cagagggtca gatgctgctg tgagaggcac agagcccttt ccgcatgtgg aagagtggga    2400
ggaagcagag ggagggactg ggcagggact gccggccccg gagtctccca cagggaggcc    2460
attccccttc tactcaccga catccctccc agcaccacac accccgcccc tgaaaggaga    2520
tcatcagccc ccacaatttg tcagagctga agccagccca ctacccaccc ccactacagc    2580
attgtgcttg ggtctgggtt ctcagtaatg tagccatttg agaaacttac ttggggacaa    2640
agtctcaatc cttattttaa atgaaaaaag aaaagaaaag cataataaat ttaaaagaaa    2700
aggctgagaa atgaaaaaaa aaaaa                                          2725
```

<210> SEQ ID NO 2
<211> LENGTH: 661
<212> TYPE: PRT
<213> ORGANISM: Homo sapiens

<400> SEQUENCE: 2

```
Met Ala Phe Asp Val Ser Cys Phe Phe Trp Val Val Leu Phe Ser Ala
1               5                   10                  15

Gly Cys Lys Val Ile Thr Ser Trp Asp Gln Met Cys Ile Glu Lys Glu
            20                  25                  30

Ala Asn Lys Thr Tyr Asn Cys Glu Asn Leu Gly Leu Ser Glu Ile Pro
        35                  40                  45

Asp Thr Leu Pro Asn Thr Thr Glu Phe Leu Glu Phe Ser Phe Asn Phe
    50                  55                  60

Leu Pro Thr Ile His Asn Arg Thr Phe Ser Arg Leu Met Asn Leu Thr
65                  70                  75                  80

Phe Leu Asp Leu Thr Arg Cys Gln Ile Asn Trp Ile His Glu Asp Thr
                85                  90                  95

Phe Gln Ser His His Gln Leu Ser Thr Leu Val Leu Thr Gly Asn Pro
            100                 105                 110

Leu Ile Phe Met Ala Glu Thr Ser Leu Asn Gly Pro Lys Ser Leu Lys
        115                 120                 125

His Leu Phe Leu Ile Gln Thr Gly Ile Ser Asn Leu Glu Phe Ile Pro
    130                 135                 140
```

```
Val His Asn Leu Glu Asn Leu Glu Ser Leu Tyr Leu Gly Ser Asn His
145                 150                 155                 160

Ile Ser Ser Ile Lys Phe Pro Lys Asp Phe Pro Ala Arg Asn Leu Lys
                165                 170                 175

Val Leu Asp Phe Gln Asn Asn Ala Ile His Tyr Ile Ser Arg Glu Asp
            180                 185                 190

Met Arg Ser Leu Glu Gln Ala Ile Asn Leu Ser Leu Asn Phe Asn Gly
        195                 200                 205

Asn Asn Val Lys Gly Ile Glu Leu Gly Ala Phe Asp Ser Thr Ile Phe
    210                 215                 220

Gln Ser Leu Asn Phe Gly Gly Thr Pro Asn Leu Ser Val Ile Phe Asn
225                 230                 235                 240

Gly Leu Gln Asn Ser Thr Thr Gln Ser Leu Trp Leu Gly Thr Phe Glu
                245                 250                 255

Asp Ile Asp Asp Glu Asp Ile Ser Ser Ala Met Leu Lys Gly Leu Cys
            260                 265                 270

Glu Met Ser Val Glu Ser Leu Asn Leu Gln Glu His Arg Phe Ser Asp
        275                 280                 285

Ile Ser Ser Thr Thr Phe Gln Cys Phe Thr Gln Leu Gln Glu Leu Asp
    290                 295                 300

Leu Thr Ala Thr His Leu Lys Gly Leu Pro Ser Gly Met Lys Gly Leu
305                 310                 315                 320

Asn Leu Leu Lys Lys Leu Val Leu Ser Val Asn His Phe Asp Gln Leu
                325                 330                 335

Cys Gln Ile Ser Ala Ala Asn Phe Pro Ser Leu Thr His Leu Tyr Ile
            340                 345                 350

Arg Gly Asn Val Lys Lys Leu His Leu Gly Val Gly Cys Leu Glu Lys
        355                 360                 365

Leu Gly Asn Leu Gln Thr Leu Asp Leu Ser His Asn Asp Ile Glu Ala
    370                 375                 380

Ser Asp Cys Cys Ser Leu Gln Leu Lys Asn Leu Ser His Leu Gln Thr
385                 390                 395                 400

Leu Asn Leu Ser His Asn Glu Pro Leu Gly Leu Gln Ser Gln Ala Phe
                405                 410                 415

Lys Glu Cys Pro Gln Leu Glu Leu Leu Asp Leu Ala Phe Thr Arg Leu
            420                 425                 430

His Ile Asn Ala Pro Gln Ser Pro Phe Gln Asn Leu His Phe Leu Gln
        435                 440                 445

Val Leu Asn Leu Thr Tyr Cys Phe Leu Asp Thr Ser Asn Gln His Leu
    450                 455                 460

Leu Ala Gly Leu Pro Val Leu Arg His Leu Asn Leu Lys Gly Asn His
465                 470                 475                 480

Phe Gln Asp Gly Thr Ile Thr Lys Thr Asn Leu Leu Gln Thr Val Gly
                485                 490                 495

Ser Leu Glu Val Leu Ile Leu Ser Cys Gly Leu Leu Ser Ile Asp
            500                 505                 510

Gln Gln Ala Phe His Ser Leu Gly Lys Met Ser His Val Asp Leu Ser
        515                 520                 525

His Asn Ser Leu Thr Cys Asp Ser Ile Asp Ser Leu Ser His Leu Lys
    530                 535                 540

Gly Ile Tyr Leu Asn Leu Ala Ala Asn Ser Ile Asn Ile Ile Ser Pro
545                 550                 555                 560

Arg Leu Leu Pro Ile Leu Ser Gln Gln Ser Thr Ile Asn Leu Ser His
```

```
                        565                 570                 575
Asn Pro Leu Asp Cys Thr Cys Ser Asn Ile His Phe Leu Thr Trp Tyr
            580                 585                 590

Lys Glu Asn Leu His Lys Leu Glu Gly Ser Glu Glu Thr Thr Cys Ala
            595                 600                 605

Asn Pro Pro Ser Leu Arg Gly Val Lys Leu Ser Asp Val Lys Leu Ser
            610                 615                 620

Cys Gly Ile Thr Ala Ile Gly Ile Phe Phe Leu Ile Val Phe Leu Leu
625                 630                 635                 640

Leu Leu Ala Ile Leu Leu Phe Phe Ala Val Lys Tyr Leu Leu Arg Trp
                645                 650                 655

Lys Tyr Gln His Ile
            660

<210> SEQ ID NO 3
<211> LENGTH: 800
<212> TYPE: DNA
<213> ORGANISM: Homo sapiens

<400> SEQUENCE: 3
acacagagag aaaggctaaa gttctctgga ggatgtggct gcagagcctg ctgctcttgg      60
gcactgtggc ctgcagcatc tctgcacccg cccgctcgcc cagccccagc acgcagccct     120
gggagcatgt gaatgccatc caggaggccc ggcgtctcct gaacctgagt agagacactg     180
ctgctgagat gaatgaaaca gtagaagtca tctcagaaat gtttgacctc caggagccga     240
cctgcctaca gacccgcctg agctgtaca agcagggcct gcggggcagc ctcaccaagc     300
tcaagggccc cttgaccatg atggccagcc actacaagca gcactgccct ccaaccccgg     360
aaacttcctg tgcaacccag attatcacct ttgaaagttt caagagaaac ctgaaggact     420
ttctgcttgt catccccttt gactgctggg agccagtcca ggagtgagac cggccagatg     480
aggctggcca agccggggag ctgctctctc atgaaacaag agctagaaac tcaggatggt     540
catcttggag ggaccaaggg gtgggccaca gccatggtgg gagtggcctg acctgccct      600 gggccacact gaccctgata caggcatggc agaagaatgg gaatatttta tactgacaga     660
aatcagtaat atttatatat ttatattttt aaaatattta tttatttatt tatttaagtt     720
catattccat atttattcaa gatgttttac cgtaataatt attattaaaa atatgcttct     780
acttgaaaaa aaaaaaaaaa                                                800

<210> SEQ ID NO 4
<211> LENGTH: 144
<212> TYPE: PRT
<213> ORGANISM: Homo sapiens

<400> SEQUENCE: 4

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80
```

Gln Gly Leu Arg Gly Ser Leu Thr Lys Leu Lys Gly Pro Leu Thr Met
      85         90        95

Met Ala Ser His Tyr Lys Gln His Cys Pro Pro Thr Pro Glu Thr Ser
      100       105       110

Cys Ala Thr Gln Ile Ile Thr Phe Glu Ser Phe Lys Glu Asn Leu Lys
   115        120        125

Asp Phe Leu Leu Val Ile Pro Phe Asp Cys Trp Glu Pro Val Gln Glu
 130        135        140

<210> SEQ ID NO 5
<211> LENGTH: 1184
<212> TYPE: DNA
<213> ORGANISM: Homo sapiens

<400> SEQUENCE: 5

```
cacagagccc gggccgcagg cacctcctcg ccagctcttc cgctcctctc acagccgcca      60
gacccgcctg ctgagcccca tggcccgcgc tgctctctcc gccgccccca gcaatccccg     120
gctcctgcga gtggcactgc tgctcctgct cctggtagcc gctggccggc gcgcagcagg     180
agcgtccgtg gccactgaac tgcgctgcca gtgcttgcag accctgcagg gaattcaccc     240
caagaacatc caaagtgtga acgtgaagtc ccccggaccc cactgcgccc aaaccgaagt     300
catagccaca ctcaagaatg gcggaaaagc ttgcctcaat cctgcatccc ccatagttaa     360
gaaaatcatc gaaagatgc tgaacagtga caaatccaac tgaccagaag ggaggaggaa     420
gctcactggt ggctgttcct gaaggaggcc ctgcccttat aggaacagaa gaggaaagag     480
agacacagct gcagaggcca cctggattgt gcctaatgtg tttgagcatc gcttaggaga     540
agtcttctat ttatttattt attcattagt tttgaagatt ctatgttaat attttaggtg     600
taaaataatt aagggtatga ttaactctac ctgcacactg tcctattata ttcattcttt     660
ttgaaatgtc aaccccaagt tagttcaatc tggattcata tttaatttga aggtagaatg     720
ttttcaaatg ttctccagtc attatgttaa tatttctgag gagcctgcaa catgccagcc     780
actgtgatag aggctggcgg atccaagcaa atggccaatg agatcattgt gaaggcaggg     840
gaatgtatgt gcacatctgt tttgtaactg tttagatgaa tgtcagttgt tatttattga     900
aatgatttca cagtgtgtgg tcaacatttc tcatgttgaa actttaagaa ctaaaatgtt     960
ctaaatatcc cttggacatt ttatgtcttt cttgtaaggc atactgcctt gtttaatggt    1020
agttttacag tgtttctggc ttagaacaaa ggggcttaat tattgatgtt tcatagaga    1080
atataaaaat aaagcactta tagaaaaaac tcgtttgatt tttgggggga aacaagggct    1140
accctttactg gaaaatctgg tgatttataa aaaaaaaaaa aaaa                    1184
```

<210> SEQ ID NO 6
<211> LENGTH: 107
<212> TYPE: PRT
<213> ORGANISM: Homo sapiens

<400> SEQUENCE: 6

Met Ala Arg Ala Ala Leu Ser Ala Ala Pro Ser Asn Pro Arg Leu Leu
1       5        10        15

Arg Val Ala Leu Leu Leu Leu Leu Val Ala Ala Gly Arg Arg Ala
     20        25        30

Ala Gly Ala Ser Val Ala Thr Glu Leu Arg Cys Gln Cys Leu Gln Thr
    35         40        45

Leu Gln Gly Ile His Pro Lys Asn Ile Gln Ser Val Asn Val Lys Ser
 50        55        60

```
Pro Gly Pro His Cys Ala Gln Thr Glu Val Ile Ala Thr Leu Lys Asn
 65                  70                  75                  80

Gly Arg Lys Ala Cys Leu Asn Pro Ala Ser Pro Ile Val Lys Lys Ile
                 85                  90                  95

Ile Glu Lys Met Leu Asn Ser Asp Lys Ser Asn
            100                 105
```

<210> SEQ ID NO 7
<211> LENGTH: 2727
<212> TYPE: DNA
<213> ORGANISM: Homo sapiens

<400> SEQUENCE: 7

```
gttaaacttc ctctctcagc cacacaggaa gctgagccgg cttggggccc agcatacaca      60
ggcccccagg acccctgggg agagggcccc gctgggctgg ccctgcaggg accatggaat     120
ccagagctga gaagctatgc agatggtgcc taaattctgc ttcccttttg atgtggaaag     180
ggagccccca gccccgccg tgcagcattt caccttcgcc ctcacagacc ttgccggcaa     240
ccgcagattt ggtttctgcc gcctgcgggc gggtacccag agctgtctct gcatcctcag     300
ccacctgcct tggttcgagg tgttttacaa gctattgaac acagtgggag acctcctagc     360
ccaggaccaa gtcaccgagg cagaggaact tcttcaaaat ctgtttcagc agtccctgtc     420
tgggccccag gcctcagtgg ggcttgagct gggcagcgga gtgacggtct ccagcgggca     480
gggtatcccc cccctaccc gggggaatag caagccgctt tcctgcttcg tggccccgga     540
ctccggccgc ctgccatcca tccctgagaa caggaaccta cggagctggt ggtggccgt     600
gactgacgag aacatcgtgg ggctgttcgc ggcgctcctg gccgagagaa gagtcctgct     660
caccgccagc aaactcagca ccctgacctc gtgcgtccac gcgtcctgcg cgctcctgta     720
ccccatgcgc tgggagcacg tgctgatccc cacgctgccc ccacacctgc tggactactg     780
ctgcgcgccc atgccctacc tcattggagt gcacgccagt ctcgccgaga gagtacgaga     840
aaaagccctg gaggacgtcg tggtgctgaa cgtggacgcc aataccttgg agacgacctt     900
taacgacgtg caggcgctgc ctccagacgt ggtgtccctg ctgaggctcc ggctcaggaa     960
ggtcgccctg cccccgggg aagggtgtc ccgtctcttc ctcaaagccc aggccctgct    1020
cttcgggggg taccgcgacg cactcgtctg cagcccgggc cagccagtga ccttcagtga    1080
ggaagtcttc ttggcccaga gcctggggc acctctgcag gccttccacc ggcgggctgt    1140
gcacctgcag ctgttcaaac agttcatcga gcccggctg gagaagctca acaaggggga    1200
gggcttctca gatcaattcg agcaggagat cactggctgc ggggcctcct caggggccct    1260
tcgatcctat cagctctggg ccgacaatct aaagaaaggt ggtggcgccc tcctgcactc    1320
agtcaaggcc aagacccaac cagccgtcaa gaacatgtac cgctcggcca agagtggctt    1380
gaaggggtg cagagccttc taatgtataa ggatggggac tctgtcctgc agagggggg    1440
ctctctgagg gccccagccc tccccagccg ctcagaccgc ctgcagcaac gcctcccaat    1500
cactcagcac tttggaaaga accggcccct tcgccccagc aggagacgcc agctggaaga    1560
gggaacttcc gagccccag gggcgggac accccactg agccctgagg atgagggtg    1620
cccgtgggca gaagaagctc tggacagcag cttcttgggg tctggagaag aactggattt    1680
gttgagcgag attctggaca gtcttagcat gggagccaag agcgcaggca gcctgagacc    1740
gagccagagt ttagactgct gtcacagagg agacctggac agctgcttca gcctgcccaa    1800
cataccaaga tggcaaccag acgataagaa actaccagag ccggagcccc agccccttc    1860
```

```
cctgccatcc ctgcaaaatg cctcgtctttt ggatgccacc agctcttcaa aggactccag    1920
gtcccagctg ataccctcag agtccgacca agaagtcacg tctccatccc agtcctcaac    1980
agcttctgca gacccaagca tctgggggga ccccaaaccc tctcctctca cagagcccct    2040
aattcttcat ctcaccccttt cccacaaggc agctgaagat tctacagccc aggaaaaccc    2100
cactccctgg ctctccactg cacccactga gcccagccct ccagaaagcc cccaaattct    2160
ggcccccaca aagcccaact ttgatatagc ctggacgtcc cagcccttg atccttcctc     2220 agacccagt tctctggagg accccagagc ccggcctccc aaagccctgc tggcagagcg     2280
cgctcacctc cagccacggg aggaaccagg agccctgaat tcccctgcta cacccaccag    2340
caactgtcaa aagtcccagc ccagcagccg gcccagagtc gctgatctta agaagtgctt    2400
tgagggttaa gaatcagggg tccaagagag accccagtcc ctcaataaag ccacaagagc    2460
ccaaaaaagc tggttttttt cctggtgaat ttctctggtg ccctcactct gctcggaaat    2520
ccatcccacc cacctctgtc cctccaaggg cagcctctct aactggctcc tagcagggaa    2580
ttccaggaag cctcctggtc ttctagaatc ctggcaacct tacaattcct ctcggcattt    2640
gtcacttcca tctcagctaa tgcacccacc agctcaaaca caccaataaa gcttttgtta    2700
catctcacta aaaaaaaaaa aaaaaaa                                        2727
```

<210> SEQ ID NO 8
<211> LENGTH: 801
<212> TYPE: PRT
<213> ORGANISM: Homo sapiens

<400> SEQUENCE: 8

Met Glu Ser Arg Ala Glu Gly Gly Ser Pro Ala Val Phe Asp Trp Phe
1               5                   10                  15

Phe Glu Ala Ala Cys Pro Ala Ser Leu Gln Glu Asp Pro Pro Ile Leu
            20                  25                  30

Arg Gln Phe Pro Pro Asp Phe Arg Asp Gln Glu Ala Met Gln Met Val
        35                  40                  45

Pro Lys Phe Cys Phe Pro Phe Asp Val Glu Arg Glu Pro Pro Ser Pro
    50                  55                  60

Ala Val Gln His Phe Thr Phe Ala Leu Thr Asp Leu Ala Gly Asn Arg
65                  70                  75                  80

Arg Phe Gly Phe Cys Arg Leu Arg Ala Gly Thr Gln Ser Cys Leu Cys
                85                  90                  95

Ile Leu Ser His Leu Pro Trp Phe Glu Val Phe Tyr Lys Leu Leu Asn
            100                 105                 110

Thr Val Gly Asp Leu Leu Ala Gln Asp Gln Val Thr Glu Ala Glu Glu
        115                 120                 125

Leu Leu Gln Asn Leu Phe Gln Gln Ser Leu Ser Gly Pro Gln Ala Ser
    130                 135                 140

Val Gly Leu Glu Leu Gly Ser Gly Val Thr Val Ser Ser Gly Gln Gly
145                 150                 155                 160

Ile Pro Pro Pro Thr Arg Gly Asn Ser Lys Pro Leu Ser Cys Phe Val
                165                 170                 175

Ala Pro Asp Ser Gly Arg Leu Pro Ser Ile Pro Glu Asn Arg Asn Leu
            180                 185                 190

Thr Glu Leu Val Val Ala Val Thr Asp Glu Asn Ile Val Gly Leu Phe
        195                 200                 205

Ala Ala Leu Leu Ala Glu Arg Arg Val Leu Leu Thr Ala Ser Lys Leu

```
            210                 215                 220
Ser Thr Leu Thr Ser Cys Val His Ala Ser Cys Ala Leu Leu Tyr Pro
225                 230                 235                 240

Met Arg Trp Glu His Val Leu Ile Pro Thr Leu Pro Pro His Leu Leu
                245                 250                 255

Asp Tyr Cys Cys Ala Pro Met Pro Tyr Leu Ile Gly Val His Ala Ser
                260                 265                 270

Leu Ala Glu Arg Val Arg Glu Lys Ala Leu Glu Asp Val Val Leu
                275                 280                 285

Asn Val Asp Ala Asn Thr Leu Glu Thr Thr Phe Asn Asp Val Gln Ala
290                 295                 300

Leu Pro Pro Asp Val Val Ser Leu Leu Arg Leu Arg Leu Arg Lys Val
305                 310                 315                 320

Ala Leu Ala Pro Gly Glu Gly Val Ser Arg Leu Phe Leu Lys Ala Gln
                325                 330                 335

Ala Leu Leu Phe Gly Gly Tyr Arg Asp Ala Leu Val Cys Ser Pro Gly
                340                 345                 350

Gln Pro Val Thr Phe Ser Glu Glu Val Phe Leu Ala Gln Lys Pro Gly
                355                 360                 365

Ala Pro Leu Gln Ala Phe His Arg Arg Ala Val His Leu Gln Leu Phe
                370                 375                 380

Lys Gln Phe Ile Glu Ala Arg Leu Glu Lys Leu Asn Lys Gly Glu Gly
385                 390                 395                 400

Phe Ser Asp Gln Phe Glu Gln Glu Ile Thr Gly Cys Gly Ala Ser Ser
                405                 410                 415

Gly Ala Leu Arg Ser Tyr Gln Leu Trp Ala Asp Asn Leu Lys Lys Gly
                420                 425                 430

Gly Gly Ala Leu Leu His Ser Val Lys Ala Lys Thr Gln Pro Ala Val
                435                 440                 445

Lys Asn Met Tyr Arg Ser Ala Lys Ser Gly Leu Lys Gly Val Gln Ser
450                 455                 460

Leu Leu Met Tyr Lys Asp Gly Asp Ser Val Leu Gln Arg Gly Gly Ser
465                 470                 475                 480

Leu Arg Ala Pro Ala Leu Pro Ser Arg Ser Asp Arg Leu Gln Gln Arg
                485                 490                 495

Leu Pro Ile Thr Gln His Phe Gly Lys Asn Arg Pro Leu Arg Pro Ser
                500                 505                 510

Arg Arg Arg Gln Leu Glu Glu Gly Thr Ser Glu Pro Gly Ala Gly
                515                 520                 525

Thr Pro Pro Leu Ser Pro Glu Asp Glu Gly Cys Pro Trp Ala Glu Glu
                530                 535                 540

Ala Leu Asp Ser Ser Phe Leu Gly Ser Gly Glu Leu Asp Leu Leu
545                 550                 555                 560

Ser Glu Ile Leu Asp Ser Leu Ser Met Gly Ala Lys Ser Ala Gly Ser
                565                 570                 575

Leu Arg Pro Ser Gln Ser Leu Asp Cys Cys His Arg Gly Asp Leu Asp
                580                 585                 590

Ser Cys Phe Ser Leu Pro Asn Ile Pro Arg Trp Gln Pro Asp Asp Lys
                595                 600                 605

Lys Leu Pro Glu Pro Glu Pro Gln Pro Leu Ser Leu Pro Ser Leu Gln
                610                 615                 620

Asn Ala Ser Ser Leu Asp Ala Thr Ser Ser Ser Lys Asp Ser Arg Ser
625                 630                 635                 640
```

Gln Leu Ile Pro Ser Glu Ser Asp Gln Glu Val Thr Ser Pro Ser Gln
                645                 650                 655

Ser Ser Thr Ala Ser Ala Asp Pro Ser Ile Trp Gly Asp Pro Lys Pro
            660                 665                 670

Ser Pro Leu Thr Glu Pro Leu Ile Leu His Leu Thr Pro Ser His Lys
        675                 680                 685

Ala Ala Glu Asp Ser Thr Ala Gln Glu Asn Pro Thr Pro Trp Leu Ser
    690                 695                 700

Thr Ala Pro Thr Glu Pro Ser Pro Pro Glu Ser Pro Gln Ile Leu Ala
705                 710                 715                 720

Pro Thr Lys Pro Asn Phe Asp Ile Ala Trp Thr Ser Gln Pro Leu Asp
                725                 730                 735

Pro Ser Ser Asp Pro Ser Ser Leu Glu Asp Pro Arg Ala Arg Pro Pro
            740                 745                 750

Lys Ala Leu Leu Ala Glu Arg Ala His Leu Gln Pro Arg Glu Glu Pro
        755                 760                 765

Gly Ala Leu Asn Ser Pro Ala Thr Pro Thr Ser Asn Cys Gln Lys Ser
    770                 775                 780

Gln Pro Ser Ser Arg Pro Arg Val Ala Asp Leu Lys Lys Cys Phe Glu
785                 790                 795                 800

Gly

<210> SEQ ID NO 9
<211> LENGTH: 1777
<212> TYPE: DNA
<213> ORGANISM: Homo sapiens

<400> SEQUENCE: 9
agaagcccag tagacaaaga aggtaagggc agtgagaatg atgcatcttg cattccttgt      60
gctgttgtgt ctgccagtct gctctgccta tcctctgagt ggggcagcaa aagaggagga     120
ctccaacaag gatcttgccc agcaatacct agaaaagtac tacaacctcg aaaaggatgt     180
gaaacagttt agaagaaagg acagtaatct cattgttaaa aaaatccaag gaatgcagaa     240
gttccttggg ttggaggtga cagggaagct agacactgac actctggagg tgatgcgcaa     300
gcccaggtgt ggagttcctg acgttggtca cttcagctcc tttcctggca tgccgaagtg     360
gaggaaaacc caccttacat acaggattgt gaattataca ccagatttgc caagagatgc     420
tgttgattct gccattgaga aagctctgaa agtctgggaa gaggtgactc cactcacatt     480
ctccaggctg tatgaaggag aggctgatat aatgatctct tttgcagtta agaacatgg      540 agacttttac tcttttgatg gcccaggaca cagtttggct catgcctacc cacctggacc     600
tgggctttat ggagatattc actttgatga tgatgaaaaa tggacagaag atgcatcagg     660
caccaattta ttcctcgttg ctgctcatga acttggccac tccctggggc tctttcactc     720
agccaacact gaagctttga tgtacccact ctacaactca ttcacagagc tcgcccagtt     780
ccgcctttcg caagatgatg tgaatggcat tcagtctctc tacggacctc cccctgcctc     840
tactgaggaa cccctggtgc ccacaaaatc tgttccttcg ggatctgaga tgccagccaa     900
gtgtgatcct gctttgtcct tcgatgccat cagcactctg agggggagaat atctgttctt     960 taaagacaga tattttggc gaagatccca ctggaaccct gaacctgaat tcatttgat     1020 ttctgcattt tggcccctctc ttccatcata tttggatgct gcatatgaag ttaacagcag    1080
ggacaccgtt tttatttta aaggaaatga gttctgggcc atcagaggaa atgaggtaca    1140

```
agcaggttat ccaagaggca tccatacct gggttttcct ccaaccataa ggaaaattga    1200
tgcagctgtt tctgacaagg aaagaagaa aacatacttc tttgcagcgg acaaatactg    1260
gagatttgat gaaaatagcc agtccatgga gcaaggcttc cctagactaa tagctgatga    1320 cttttccagga gttgagccta aggttgatgc tgtattacag gcatttggat ttttctactt    1380
cttcagtgga tcatcacagt ttgagtttga ccccaatgcc aggatggtga cacacatatt    1440
aaagagtaac agctggttac attgctaggc gagataggg gaagacagat atgggtgttt    1500
ttaataaatc taataattat tcatctaatg tattatgagc caaaatggtt aattttttcct    1560 gcatgttctg tgactgaaga agatgagcct tgcagatatc tgcatgtgtc atgaagaatg    1620
tttctggaat tcttcacttg cttttgaatt gcactgaaca gaattaagaa atactcatgt    1680
gcaataggtg agagaatgta ttttcataga tgtgttatta cttcctcaat aaaaagtttt    1740
attttgggcc tgttccttaa aaaaaaaaaa aaaaaaa                             1777
```

<210> SEQ ID NO 10
<211> LENGTH: 476
<212> TYPE: PRT
<213> ORGANISM: Homo sapiens

<400> SEQUENCE: 10

```
Met Met His Leu Ala Phe Leu Val Leu Leu Cys Leu Pro Val Cys Ser
1               5                   10                  15

Ala Tyr Pro Leu Ser Gly Ala Ala Lys Glu Glu Asp Ser Asn Lys Asp
            20                  25                  30

Leu Ala Gln Gln Tyr Leu Glu Lys Tyr Tyr Asn Leu Glu Lys Asp Val
        35                  40                  45

Lys Gln Phe Arg Arg Lys Asp Ser Asn Leu Ile Val Lys Lys Ile Gln
    50                  55                  60

Gly Met Gln Lys Phe Leu Gly Leu Glu Val Thr Gly Lys Leu Asp Thr
65                  70                  75                  80

Asp Thr Leu Glu Val Met Arg Lys Pro Arg Cys Gly Val Pro Asp Val
                85                  90                  95

Gly His Phe Ser Ser Phe Pro Gly Met Pro Lys Trp Arg Lys Thr His
            100                 105                 110

Leu Thr Tyr Arg Ile Val Asn Tyr Thr Pro Asp Leu Pro Arg Asp Ala
        115                 120                 125

Val Asp Ser Ala Ile Glu Lys Ala Leu Lys Val Trp Glu Glu Val Thr
    130                 135                 140

Pro Leu Thr Phe Ser Arg Leu Tyr Glu Gly Glu Ala Asp Ile Met Ile
145                 150                 155                 160

Ser Phe Ala Val Lys Glu His Gly Asp Phe Tyr Ser Phe Asp Gly Pro
                165                 170                 175

Gly His Ser Leu Ala His Ala Tyr Pro Pro Gly Pro Gly Leu Tyr Gly
            180                 185                 190

Asp Ile His Phe Asp Asp Asp Glu Lys Trp Thr Glu Ala Ser Gly
        195                 200                 205

Thr Asn Leu Phe Leu Val Ala Ala His Glu Leu Gly His Ser Leu Gly
    210                 215                 220

Leu Phe His Ser Ala Asn Thr Glu Ala Leu Met Tyr Pro Leu Tyr Asn
225                 230                 235                 240

Ser Phe Thr Glu Leu Ala Gln Phe Arg Leu Ser Gln Asp Asp Val Asn
                245                 250                 255

Gly Ile Gln Ser Leu Tyr Gly Pro Pro Pro Ala Ser Thr Glu Glu Pro
```

```
                   260             265             270
Leu Val Pro Thr Lys Ser Val Pro Ser Gly Ser Glu Met Pro Ala Lys
            275             280             285

Cys Asp Pro Ala Leu Ser Phe Asp Ala Ile Ser Thr Leu Arg Gly Glu
            290             295             300

Tyr Leu Phe Phe Lys Asp Arg Tyr Phe Trp Arg Ser His Trp Asn
305             310             315             320

Pro Glu Pro Glu Phe His Leu Ile Ser Ala Phe Trp Pro Ser Leu Pro
                    325             330             335

Ser Tyr Leu Asp Ala Ala Tyr Glu Val Asn Ser Arg Asp Thr Val Phe
                340             345             350

Ile Phe Lys Gly Asn Glu Phe Trp Ala Ile Arg Gly Asn Glu Val Gln
            355             360             365

Ala Gly Tyr Pro Arg Gly Ile His Thr Leu Gly Phe Pro Pro Thr Ile
            370             375             380

Arg Lys Ile Asp Ala Ala Val Ser Asp Lys Glu Lys Lys Lys Thr Tyr
385             390             395             400

Phe Phe Ala Ala Asp Lys Tyr Trp Arg Phe Asp Glu Asn Ser Gln Ser
                405             410             415

Met Glu Gln Gly Phe Pro Arg Leu Ile Ala Asp Asp Phe Pro Gly Val
                420             425             430

Glu Pro Lys Val Asp Ala Val Leu Gln Ala Phe Gly Phe Phe Tyr Phe
            435             440             445

Phe Ser Gly Ser Ser Gln Phe Glu Phe Asp Pro Asn Ala Arg Met Val
            450             455             460

Thr His Ile Leu Lys Ser Asn Ser Trp Leu His Cys
465             470             475

<210> SEQ ID NO 11
<211> LENGTH: 3309
<212> TYPE: DNA
<213> ORGANISM: Homo sapiens

<400> SEQUENCE: 11
ttcagcccct ctcccgggct gcgcctccgc actccgggcc cgggcagaag ggggtgcgcc      60
tcggccccac cacccaggga gcagccgagc tgaaaggccg ggaaccgcgg cttgcgggga     120
ccacagctcc cgaaagcgac gttcggccac cggaggagcg ggagccaagc aggcggagct     180
cggcgggaga ggtgcgggcc gaatccgagc cgagcggaga ggaatccggc agtagagagc     240
ggactccagc cggcggaccc tgcagccctc gcctgggaca cgcggcgcgct gggcaggcgc     300 ccaagagagc atcgagcagc ggaacccgcg aagccggccc gcagccgcga cccgcgcagc     360
ctgccgctct cccgccgccg gtccgggcag catgaggcgc gcggcgctct ggctctggct     420
gtgcgcgctg gcgctgagcc tgcagccggc cctgccgcaa attgtggcta ctaatttgcc     480
ccctgaagat caagatggct ctggggatga ctctgacaac ttctccggct caggtgcagg     540
tgctttgcaa gatatcacct tgtcacagca dccccctcc acttggaagg acacgcagct     600
cctgacggct attcccacgt ctccagaacc caccggcctg gaggctacag ctgcctccac     660 ctccacccctg ccggctggag aggggcccaa ggagggagag gctgtagtcc tgccagaagt     720
ggagcctggc ctcaccgccc gggagcagga ggccacccccc cgacccaggg agaccacaca     780
gctcccgacc actcatcagg cctcaacgac cacagccacc acggcccagg agcccgccac     840
ctcccacccc cacagggaca tgcagcctgg ccaccatgag acctcaaccc ctgcaggacc     900
```

```
cagccaagct gaccttcaca ctccccacac agaggatgga ggtccttctg ccaccgagag    960
ggctgctgag gatggagcct ccagtcagct cccagcagca gagggctctg ggagcagga    1020
cttcaccttt gaaacctcgg gggagaatac ggctgtagtg gccgtggagc ctgaccgccg   1080
gaaccagtcc ccagtggatc aggggccac ggggcctca cagggcctcc tggacaggaa    1140
agaggtgctg ggaggggtca ttgccggagg cctcgtgggg ctcatctttg ctgtgtgcct   1200
ggtgggtttc atgctgtacc gcatgaagaa gaaggacgaa ggcagctact ccttggagga   1260
gccgaaacaa gccaacggcg gggcctacca gaagcccacc aaacaggagg aattctatgc   1320
ctgacgcggg agccatgcgc cccctccgcc ctgccactca ctaggccccc acttgcctct   1380
tccttgaaga actgcaggcc ctggcctccc ctgccaccag gccacctccc cagcattcca   1440
gcccctctgg tcgctcctgc ccacggagtc gtggggtgtg ctgggagctc cactctgctt   1500
ctctgacttc tgcctggaga cttagggcac caggggtttc tcgcatagga cctttccacc   1560
acagccagca cctggcatcg caccattctg actcggtttc tccaaactga agcagcctct   1620
ccccaggtcc agctctggag gggaggggga tccgactgct ttggacctaa atggcctcat   1680
gtggctggaa gatcctgcgg gtggggcttg gggctcacac acctgtagca cttactggta   1740
ggaccaagca tcttgggggg gtggccgctg agtggcaggg gacaggagtc cactttgttt   1800
cgtggggagg tctaatctag atatcgactt gttttttgcac atgtttcctc tagttctttg   1860
ttcatagccc agtagacctt gttacttctg aggtaagtta agtaagttga ttcggtatcc   1920
ccccatcttg cttccctaat ctatggtcgg gagacagcat cagggttaag aagactttt   1980
tttttttttt ttaaactagg agaaccaaat ctggaagcca aaatgtaggc ttagtttgtg   2040
tgttgtctct tgagtttgtc gctcatgtgt gcaacagggt atggactatc tgtctggtgg   2100
ccccgtttct ggtggtctgt tggcaggctg gccagtccag gctgccgtgg ggccgccgcc   2160
tctttcaagc agtcgtgcct gtgtccatgc gctcagggcc atgctgaggc ctgggccgct   2220
gccacgttgg agaagcccgt gtgagaagtg aatgctggga ctcagccttc agacagagag   2280
gactgtaggg agggcggcag gggcctggag atcctcctgc agaccacgcc cgtcctgcct   2340
gtggcgccgt ctccaggggc tgcttcctcc tggaaattga cgaggggtgt cttgggcaga   2400
gctggctctg agcgcctcca tccaaggcca ggttctccgt tagctcctgt ggccccaccc   2460
tgggccctgg gctggaatca ggaatatttt ccaaagagtg atagtctttt gcttttggca   2520
aaactctact taatccaatg ggttttttccc tgtacagtag attttccaaa tgtaataaac   2580
tttaatataa agtagtcctg tgaatgccac tgccttcgct tcttgcctct gtgctgtgtg   2640
tgacgtgacc ggacttttct gcaaacacca acatgttggg aaacttggct cgaatctctg   2700
tgccttcgtc tttcccatgg ggagggattc tggttccagg gtccctctgt gtatttgctt   2760
ttttgttttg gctgaaattc tcctggaggt cggtaggttc agccaaggtt ttataaggct   2820
gatgtcaatt tctgtgttgc caagctccaa gccccatctt ctaaatggca aaggaaggtg   2880
gatggcccca gcacagcttg acctgaggct gtggtcacag cggaggtgtg gagccgaggc   2940
ctaccccgca gacaccttgg acatcctcct cccacccggc tgcagaggcc agaggccccc   3000
agcccagggc tcctgcactt acttgcttat ttgacaacgt ttcagcgact ccgttggcca   3060
ctccgagagg tgggccagtc tgtggatcag agatgcacca ccaagccaag ggaacctgtg   3120
tccggtattc gatactgcga cttttctgcc tggagtgtatg actgcacatg actcgggggt   3180
ggggaaaggg gtcggctgac catgctcatc tgctggtccg tgggacgtgt cccaagccag   3240
aggctgggtt catttgtgta acgacaataa acggtacttg tcatttcggg caaaaaaaaa   3300
``` aaaaaaaaa 3309

<210> SEQ ID NO 12
<211> LENGTH: 310
<212> TYPE: PRT
<213> ORGANISM: Homo sapiens

<400> SEQUENCE: 12

```
Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Ser Asp Asn Phe Ser Gly Ser Gly
        35                  40                  45

Ala Gly Ala Leu Gln Asp Ile Thr Leu Ser Gln Gln Thr Pro Ser Thr
    50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Leu Ala Ser Thr Thr Ala Thr Thr
    130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310
```

<210> SEQ ID NO 13
<211> LENGTH: 2442
<212> TYPE: DNA
<213> ORGANISM: Homo sapiens

<400> SEQUENCE: 13

```
agcctcagcc ttgcctctcc ccctcttgct ttatctcctc atttctgtgt gcaggcgagc      60
ttcttggcct aagggcagga agagatggca gcggggagag cgcagctcta cgccaaggtc     120
tccaacaagc tcaagagccg cagcagcccc tcgctcctgg agcccctcct ggccatgggc     180
ttcccggtgc acaccgcgct gaaagcgttg gcagccacgg ggaggaagac ggcggaggag     240
gccttggcct ggctgcatga tcattgcaat gacccttccc tagacgaccc catcccccag     300
gagtatgccc ttttcctctg tccaacgggg cccctgctgg aaaaacttca agagttctgg     360
agagagagca agcgccagtg tgcaaagaac agagctcatg aggtcttccc acacgtgaca     420
ctctgtgact tcttcacgtg tgaagaccag aaggtggaat gcctgtacga ggcgctgaag     480
agagctggag acaggctcct gggctccttc cccacggccg tgcctctggc tctccactcc     540
tccatcagct acctcggctt cttcgtcagt ggcagcccg cagacgtcat ccgggaattc     600
gccatgacct tcgccacgga agcatctctc ttagcagact gctccgtgaa gccttgcacc     660
aaacagctgc atctgacctt ggcccacaag ttctaccccc accaccagag gacgctggag     720
cagctggcca gagccatccc cctgggccac agctgccagt ggaccgcagc actctactcc     780
cgagacatgc gctttgtgca ctaccagacc ctgagagccc tattccagta caaaccccag     840
aacgtggatg agctgacgct aagtcctggt gactacatct ttgtggaccc cacgcagcag     900
gacgaagcca gcgagggctg ggtgattggg atctcacagc ggacgggctg ccggggcttc     960
ctgccggaaa actacacgga tcgagccagt gagtctgaca cgtgggtgaa gcacaggatg    1020
tacaccttca gtctagccac agacctgaac tccagaaagg atggtgaagc cagcagcaga    1080
tgcagcgggg aatttcttcc acaaacggca aggagtctta gcagcttaca ggccttgcag    1140
gctaccgttg caaggaagag cgtgctggtg gttcgccacg gggagagagt ggatcagatc    1200
ttcgggaagg catggctgca gcaatgctcc actcctgatg ggaaatacta caggccagac    1260
ctgaatttcc cctgcagtct gccaagacgg agtcgtggga tcaaagactt tgaaaacgat    1320
cccccattat catcgtgtgg catttttccag tccagaattg caggggacgc gctactggac    1380
agtggtatca gaatcagctc tgtgtttgcc tccccagccc tccgctgtgt gcagacggcc    1440
aaactcatcc tggaagaact caaactggag aaaaaaatca agatacgagt ggaacctgga    1500
atctttgaat ggacaaaatg ggaagctggc aaaaccaccc caaccctcat gagcctggaa    1560
gagctgaaag aggcaaattt caacattgac actgattaca ggcccgcgtt tcccctgtcc    1620
gccctcatgc cggccgagag ctaccaggag tacatggaca ggtgcacggc gagcatggtg    1680
caaatcgtca acacctgtcc acaggacacg ggtgtcatcc taattgtgag tcacggctcc    1740
actctggact cctgcacgcg gccactgctc gggctgccgc cccgggaatg tggggatttt    1800
gcccaactcg tgagaaagat cccttccctg gcatgtgct tctgtgaaga aaataaagag    1860
gaaggaaaat gggagttggt gaacccaccg gtgaagaccc tgacccacgg ggcgaacgca    1920
gcatttaact ggaggaactg gatctcaggc aactgagagc cacggtgatg ttgtcataac    1980
ctcagagtgg agaggcagaa accatgtgca gaggctggga gatgctgctg tttcagagg    2040 cgtcttagtc tcacccaatg tgatttgtag aagcacgaga cgcactttta tatcccggaa    2100
tatttccctc cggctttcgc ctttgtaact cccatctgtg gacccatcgt ccaccagccc    2160
agctgcgggg agcacagggc aggtggctgg gtgaggatgc cgccctgcag catgtacacc    2220
gagtgtctgc agctggggac acaactgccc gggactctaa cttccaggaa ttaaagactc    2280
accacacacg aaggatctaa ccacttcatt ttccatggtc taatcattaa attcccaatc    2340
gttttttctt tttctgggtc catcactctt tagccatatc cacatgggct aaaacaggtg    2400
```
taatagtcaa taaaatggtc ccagaaaacc atcgaccagg tc                              2442

<210> SEQ ID NO 14
<211> LENGTH: 661
<212> TYPE: PRT
<213> ORGANISM: Homo sapiens

<400> SEQUENCE: 14

Met Ala Ala Gly Glu Thr Gln Leu Tyr Ala Lys Val Ser Asn Lys Leu
1               5                   10                  15

Lys Ser Arg Ser Ser Pro Ser Leu Leu Glu Pro Leu Leu Ala Met Gly
                20                  25                  30

Phe Pro Val His Thr Ala Leu Lys Ala Leu Ala Ala Thr Gly Arg Lys
            35                  40                  45

Thr Ala Glu Glu Ala Leu Ala Trp Leu His Asp His Cys Asn Asp Pro
        50                  55                  60

Ser Leu Asp Asp Pro Ile Pro Gln Glu Tyr Ala Leu Phe Leu Cys Pro
65                  70                  75                  80

Thr Gly Pro Leu Leu Glu Lys Leu Gln Glu Phe Trp Arg Glu Ser Lys
                85                  90                  95

Arg Gln Cys Ala Lys Asn Arg Ala His Glu Val Phe Pro His Val Thr
            100                 105                 110

Leu Cys Asp Phe Phe Thr Cys Glu Asp Gln Lys Val Glu Cys Leu Tyr
        115                 120                 125

Glu Ala Leu Lys Arg Ala Gly Asp Arg Leu Leu Gly Ser Phe Pro Thr
    130                 135                 140

Ala Val Pro Leu Ala Leu His Ser Ser Ile Ser Tyr Leu Gly Phe Phe
145                 150                 155                 160

Val Ser Gly Ser Pro Ala Asp Val Ile Arg Glu Phe Ala Met Thr Phe
                165                 170                 175

Ala Thr Glu Ala Ser Leu Leu Ala Gly Thr Ser Val Ser Arg Phe Trp
            180                 185                 190

Ile Phe Ser Gln Val Pro Gly His Gly Pro Asn Leu Arg Leu Ser Asn
        195                 200                 205

Leu Thr Arg Ala Ser Phe Val Ser His Tyr Ile Leu Gln Lys Tyr Cys
    210                 215                 220

Ser Val Lys Pro Cys Thr Lys Gln Leu His Leu Thr Leu Ala His Lys
225                 230                 235                 240

Phe Tyr Pro His His Gln Arg Thr Leu Glu Gln Leu Ala Arg Ala Ile
                245                 250                 255

Pro Leu Gly His Ser Cys Gln Trp Thr Ala Ala Leu Tyr Ser Arg Asp
            260                 265                 270

Met Arg Phe Val His Tyr Gln Thr Leu Arg Ala Leu Phe Gln Tyr Lys
        275                 280                 285

Pro Gln Asn Val Asp Glu Leu Thr Leu Ser Pro Gly Asp Tyr Ile Phe
    290                 295                 300

Val Asp Pro Thr Gln Gln Asp Glu Ala Ser Glu Gly Trp Val Ile Gly
305                 310                 315                 320

Ile Ser Gln Arg Thr Gly Cys Arg Gly Phe Leu Pro Glu Asn Tyr Thr
                325                 330                 335

Asp Arg Ala Ser Glu Ser Asp Thr Trp Val Lys His Arg Met Tyr Thr
            340                 345                 350

Phe Ser Leu Ala Thr Asp Leu Asn Ser Arg Lys Asp Gly Glu Ala Ser
        355                 360                 365

```
Ser Arg Cys Ser Gly Glu Phe Leu Pro Gln Thr Ala Arg Ser Leu Ser
    370                 375                 380

Ser Leu Gln Ala Leu Gln Ala Thr Val Ala Arg Lys Ser Val Leu Val
385                 390                 395                 400

Val Arg His Gly Glu Arg Val Asp Gln Ile Phe Gly Lys Ala Trp Leu
                405                 410                 415

Gln Gln Cys Ser Thr Pro Asp Gly Lys Tyr Tyr Arg Pro Asp Leu Asn
            420                 425                 430

Phe Pro Cys Ser Leu Pro Arg Arg Ser Arg Gly Ile Lys Asp Phe Glu
        435                 440                 445

Asn Asp Pro Pro Leu Ser Ser Cys Gly Ile Phe Gln Ser Arg Ile Ala
    450                 455                 460

Gly Asp Ala Leu Leu Asp Ser Gly Ile Arg Ile Ser Ser Val Phe Ala
465                 470                 475                 480

Ser Pro Ala Leu Arg Cys Val Gln Thr Ala Lys Leu Ile Leu Glu Glu
                485                 490                 495

Leu Lys Leu Glu Lys Lys Ile Lys Ile Arg Val Glu Pro Gly Ile Phe
            500                 505                 510

Glu Trp Thr Lys Trp Glu Ala Gly Lys Thr Thr Pro Thr Leu Met Ser
        515                 520                 525

Leu Glu Glu Leu Lys Glu Ala Asn Phe Asn Ile Asp Thr Asp Tyr Arg
530                 535                 540

Pro Ala Phe Pro Leu Ser Ala Leu Met Pro Ala Glu Ser Tyr Gln Glu
545                 550                 555                 560

Tyr Met Asp Arg Cys Thr Ala Ser Met Val Gln Ile Val Asn Thr Cys
                565                 570                 575

Pro Gln Asp Thr Gly Val Ile Leu Ile Val Ser His Gly Ser Thr Leu
            580                 585                 590

Asp Ser Cys Thr Arg Pro Leu Leu Gly Leu Pro Pro Arg Glu Cys Gly
        595                 600                 605

Asp Phe Ala Gln Leu Val Arg Lys Ile Pro Ser Leu Gly Met Cys Phe
    610                 615                 620

Cys Glu Glu Asn Lys Glu Glu Gly Lys Trp Glu Leu Val Asn Pro Pro
625                 630                 635                 640

Val Lys Thr Leu Thr His Gly Ala Asn Ala Ala Phe Asn Trp Arg Asn
                645                 650                 655

Trp Ile Ser Gly Asn
                660

<210> SEQ ID NO 15
<211> LENGTH: 1940
<212> TYPE: DNA
<213> ORGANISM: Homo sapiens

<400> SEQUENCE: 15
gagtgagcgg cgcggggcca atcagcgtgc gccgttccga aagttgcctt ttatggctcg      60
agcggccgcg gcggcgccct ataaaaccca gcggcgcgac gcgccaccac cgccgagacc     120
gcgtccgccc cgcgagcaca gagcctcgcc tttgccgatc cgccgcccgt ccacacccgc     180
cgccagctca ccatggatga tgatatcgcc gcgctcgtcg tcgacaacgg ctccggcatg     240
tgcaaggccg gcttcgcggg cgacgatgcc ccccgggccg tcttcccctc catcgtgggg     300
cgccccaggc accagggcgt gatggtgggc atgggtcaga aggattccta tgtgggcgac     360
gaggcccaga gcaagagagg catcctcacc ctgaagtacc ccatcgagca cggcatcgtc     420
```

```
accaactggg acgacatgga gaaaatctgg caccacacct tctacaatga gctgcgtgtg    480
gctcccgagg agcaccccgt gctgctgacc gaggcccccc tgaacccaa ggccaaccgc    540
gagaagatga cccagatcat gtttgagacc ttcaacaccc cagccatgta cgttgctatc    600
caggctgtgc tatccctgta cgcctctggc cgtaccactg catcgtgat ggactccggt    660
gacggggtca cccacactgt gcccatctac gaggggtatg ccctccccca tgccatcctg    720
cgtctggacc tggctggccg ggacctgact gactacctca tgaagatcct caccgagcgc    780
ggctacagct tcaccaccac ggccgagcgg gaaatcgtgc gtgacattaa ggagaagctg    840
tgctacgtcg ccctggactt cgagcaagag atggccacgg ctgcttccag ctcctccctg    900
gagaagagct acgagctgcc tgacggccag gtcatcacca ttggcaatga gcggttccgc    960
tgccctgagg cactcttcca gccttccttc ctgggcatgg agtcctgtgg catccacgaa   1020
actaccttca actccatcat gaagtgtgac gtggacatcc gcaaagacct gtacgccaac   1080
acagtgctgt ctggcggcac caccatgtac cctggcattg ccgacaggat gcagaaggag   1140
atcactgccc tggcacccag cacaatgaag atcaagatca ttgctcctcc tgagcgcaag   1200
tactccgtgt ggatcggcgg ctccatcctg gcctcgctgt ccaccttcca gcagatgtgg   1260
atcagcaagc aggagtatga cgagtccggc ccctccatcg tccaccgcaa atgcttctag   1320
gcggactatg acttagttgc gttacaccct tccttgacaa aacctaactt gcgcagaaaa   1380
caagatgaga ttggcatggc tttatttgtt ttttttgttt tgttttggtt ttttttttt   1440
ttttggcttg actcaggatt taaaaactgg aacggtgaag gtgacagcag tcggttggag   1500
cgagcatccc ccaaagttca caatgtggcc gaggactttg attgcacatt gttgtttttt   1560
taatagtcat tccaaatatg agatgcgttg ttacaggaag tcccttgcca tcctaaaagc   1620
cacccccactt ctctctaagg agaatggccc agtcctctcc caagtccaca caggggaggt   1680
gatagcattg ctttcgtgta aattatgtaa tgcaaaattt ttttaatctt cgccttaata   1740
cttttttatt ttgttttatt ttgaatgatg agccttcgtg ccccccttc ccctttttt   1800
gtcccccaac ttgagatgta tgaaggcttt tggtctccct gggagtgggt ggaggcagcc   1860
agggcttacc tgtacactga cttgagacca gttgaataaa agtgcacacc ttaaaaatga   1920
ggaaaaaaaa aaaaaaaaa                                              1940
```

<210> SEQ ID NO 16
<211> LENGTH: 375
<212> TYPE: PRT
<213> ORGANISM: Homo sapiens

<400> SEQUENCE: 16

```
Met Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
                20                  25                  30

Ser Ile Val Gly Arg Pro Arg His Gln Gly Val Met Val Gly Met Gly
            35                  40                  45

Gln Lys Asp Ser Tyr Val Gly Asp Glu Ala Gln Ser Lys Arg Gly Ile
        50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95
```

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Met Ala Thr Ala Ala Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285

Ile Arg Lys Asp Leu Tyr Ala Asn Thr Val Leu Ser Gly Gly Thr Thr
    290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
        355                 360                 365

Ile Val His Arg Lys Cys Phe
    370                 375

<210> SEQ ID NO 17
<211> LENGTH: 1309
<212> TYPE: DNA
<213> ORGANISM: Homo sapiens

<400> SEQUENCE: 17
gctctctgct cctcctgttc gacagtcagc cgcatcttct tttgcgtcgc cagccgagcc    60
acatcgctca gacaccatgg ggaaggtgaa ggtcggagtc aacggatttg gtcgtattgg   120
gcgcctggtc accagggctg cttttaactc tggtaaagtg gatattgttg ccatcaatga   180
ccccttcatt gacctcaact acatggttta catgttccaa tatgattcca cccatggcaa   240
attccatggc accgtcaagg ctgagaacgg gaagcttgtc atcaatggaa atccatcac    300 catcttccag gagcgagatc cctccaaaat caagtggggc gatgctggcg ctgagtacgt   360
cgtggagtcc actggcgtct tcaccaccat ggagaaggct ggggctcatt tgcaggggg    420 agccaaaagg gtcatcatct ctgccccctc tgctgatgcc cccatgttcg tcatgggtgt   480
gaaccatgag aagtatgaca cagcctcaa gatcatcagc aatgcctcct gcaccaccaa   540

```
ctgcttagca  ccctggcca   aggtcatcca  tgacaacttt  ggtatcgtgg  aaggactcat    600
gaccacagtc  catgccatca  ctgccaccca  gaagactgtg  gatggcccct  ccgggaaact    660
gtggcgtgat  ggccgcgggg  ctctccagaa  catcatccct  gcctctactg  gcgctgccaa    720
ggctgtgggc  aaggtcatcc  tgagctgaac  gggaagctc   actggcatgg  ccttccgtgt    780
ccccactgcc  aacgtgtcag  tggtggacct  gacctgccgt  ctagaaaaac  ctgccaaata    840
tgatgacatc  aagaaggtgg  tgaagcaggc  gtcggagggc  cccctcaagg  gcatcctggg    900
ctacactgag  caccaggtgg  tctcctctga  cttcaacagc  gacacccact  cctccacctt    960
tgacgctggg  gctggcattg  ccctcaacga  ccactttgtc  aagctcattt  cctggtatga   1020
caacgaattt  ggctacagca  acagggtggt  ggacctcatg  gcccacatgg  cctccaagga   1080
gtaagacccc  tggaccacca  gcccagcaa   gagcacaaga  ggaagagaga  gaccctcact   1140
gctggggagt  ccctgccaca  ctcagtcccc  caccacactg  aatctcccct  cctcacagtt   1200
gccatgtaga  cccttgaag   aggggagggg  cctaggagc   cgcaccttgt  catgtaccat   1260
caataaagta  ccctgtgctc  aaccagttaa  aaaaaaaaa   aaaaaaaaa                 1309
```

<210> SEQ ID NO 18
<211> LENGTH: 335
<212> TYPE: PRT
<213> ORGANISM: Homo sapiens

<400> SEQUENCE: 18

Met Gly Lys Val Lys Val Gly Val Asn Gly Phe Gly Arg Ile Gly Arg
1               5                   10                  15

Leu Val Thr Arg Ala Ala Phe Asn Ser Gly Lys Val Asp Ile Val Ala
                20                  25                  30

Ile Asn Asp Pro Phe Ile Asp Leu Asn Tyr Met Val Tyr Met Phe Gln
            35                  40                  45

Tyr Asp Ser Thr His Gly Lys Phe His Gly Thr Val Lys Ala Glu Asn
        50                  55                  60

Gly Lys Leu Val Ile Asn Gly Asn Pro Ile Thr Ile Phe Gln Glu Arg
65                  70                  75                  80

Asp Pro Ser Lys Ile Lys Trp Gly Asp Ala Gly Ala Glu Tyr Val Val
                85                  90                  95

Glu Ser Thr Gly Val Phe Thr Thr Met Glu Lys Ala Gly Ala His Leu
            100                 105                 110

Gln Gly Gly Ala Lys Arg Val Ile Ile Ser Ala Pro Ser Ala Asp Ala
        115                 120                 125

Pro Met Phe Val Met Gly Val Asn His Glu Lys Tyr Asp Asn Ser Leu
    130                 135                 140

Lys Ile Ile Ser Asn Ala Ser Cys Thr Thr Asn Cys Leu Ala Pro Leu
145                 150                 155                 160

Ala Lys Val Ile His Asp Asn Phe Gly Ile Val Glu Gly Leu Met Thr
                165                 170                 175

Thr Val His Ala Ile Thr Ala Thr Gln Lys Thr Val Asp Gly Pro Ser
            180                 185                 190

Gly Lys Leu Trp Arg Asp Gly Arg Gly Ala Leu Gln Asn Ile Ile Pro
        195                 200                 205

Ala Ser Thr Gly Ala Ala Lys Ala Val Gly Lys Val Ile Pro Glu Leu
    210                 215                 220

Asn Gly Lys Leu Thr Gly Met Ala Phe Arg Val Pro Thr Ala Asn Val
225                 230                 235                 240

```
Ser Val Val Asp Leu Thr Cys Arg Leu Glu Lys Pro Ala Lys Tyr Asp
            245                 250                 255

Asp Ile Lys Lys Val Val Lys Gln Ala Ser Glu Gly Pro Leu Lys Gly
        260                 265                 270

Ile Leu Gly Tyr Thr Glu His Gln Val Val Ser Ser Asp Phe Asn Ser
        275                 280                 285

Asp Thr His Ser Ser Thr Phe Asp Ala Gly Ala Gly Ile Ala Leu Asn
        290                 295                 300

Asp His Phe Val Lys Leu Ile Ser Trp Tyr Asp Asn Glu Phe Gly Tyr
305                 310                 315                 320

Ser Asn Arg Val Val Asp Leu Met Ala His Met Ala Ser Lys Glu
            325                 330                 335

<210> SEQ ID NO 19
<211> LENGTH: 2321
<212> TYPE: DNA
<213> ORGANISM: Homo sapiens

<400> SEQUENCE: 19
gtcctcaacc aagatggcgc ggatggcttc aggcgcatca cgacaccggc gcgtcacgcg      60
acccgcccta cgggcacctc ccgcgctttt cttagcgccg cagacggtgg ccgagcgggg     120
gaccgggaag catggcccgg gggtcggcgg ttgcctgggc ggcgctcggg ccgttgttgt     180
ggggctgcgc gctggggctg cagggcggga tgctgtaccc ccaggagagc ccgtcgcggg     240
agtgcaagga gctggacggc ctctggagct ccgcgccga cttctctgac aaccgacgcc      300
ggggcttcga ggagcagtgg taccggcggc cgctgtggga gtcaggcccc accgtggaca     360
tgccagttcc ctccagcttc aatgacatca gccaggactg gcgtctgcgg cattttgtcg     420
gctgggtgtg gtacgaacgg gaggtgatcc tgccggagcg atggacccag gacctgcgca     480
caagagtggt gctgaggatt ggcagtgccc attcctatgc catcgtgtgg ggtgaatgggg     540 tcgacacgct agagcatgag gggggctacc tcccccttcga ggccgacatc agcaacctgg    600
tccaggtggg gcccctgccc tcccggctcc gaatcactat cgccatcaac aacacactca     660
cccccaccac cctgccacca gggaccatcc aatacctgac tgacacctcc aagtatccca     720
agggttactt tgtccagaac acatattttg acttttttcaa ctacgctgga ctgcagcggt     780
ctgtacttct gtacacgaca cccaccaccct acatcgatga catcaccgtc accaccagcg     840
tggagcaaga cagtgggctg gtgaattacc agatctctgt caagggcagt aacctgttca     900
agttggaagt gcgtctttg gatgcagaaa acaaagtcgt ggcgaatggg actgggaccc      960
agggccaact taaggtgcca ggtgtcagcc tctggtggcc gtacctgatg cacgaacgcc    1020
ctgcctatct gtattcattg gaggtgcagc tgactgcaca gacgtcactg gggcctgtgt    1080
ctgacttcta cacactccct gtggggatcc gcactgtggc tgtcaccaag agccagttcc    1140
tcatcaatgg gaaacctttc tatttccacg gtgtcaacaa gcatgaggat gcggacatcc    1200
gagggaaggg cttcgactgg ccgctgctgg tgaaggactt caacctgctt cgctggcttg    1260
gtgccaacgc tttccgtacc agccactacc cctatgcaga ggaagtgatg cagatgtgtg    1320
accgctatgg gattgtggtc atcgatgagt gtcccggcgt gggcctggcg ctgccgcagt    1380
tcttcaacaa cgtttctctg catcaccaca tgcaggtgat ggaagaagtg gtgcgtaggg    1440
acaagaacca ccccgcggtc gtgatgtggt ctgtggccaa cgagcctgcg tcccacctag    1500
aatctgctgg ctactacttg aagatggtga tcgctcacac caaatccttg gaccccctccc    1560
```

```
ggcctgtgac ctttgtgagc aactctaact atgcagcaga caagggggct ccgtatgtgg    1620
atgtgatctg tttgaacagc tactactctt ggtatcacga ctacgggcac ctggagttga    1680
ttcagctgca gctggccacc cagtttgaga actggtataa gaagtatcag aagcccatta    1740
ttcagagcga gtatggagca gaaacgattg cagggtttca ccaggatcca cctctgatgt    1800
tcactgaaga gtaccagaaa agtctgctag agcagtacca tctgggtctg gatcaaaaac    1860
gcagaaaata cgtggttgga gagctcattt ggaattttgc cgatttcatg actgaacagt    1920
caccgacgag agtgctgggg aataaaaagg ggatcttcac tcggcagaga caaccaaaaa    1980
gtgcagcgtt cctttttgcga gagagatact ggaagattgc caatgaaacc aggtatcccc    2040
actcagtagc caagtcacaa tgtttggaaa acagcctgtt tacttgagca agactgatac    2100
cacctgcgtg tcccttcctc cccgagtcag ggcgacttcc acagcagcag aacaagtgcc    2160
tcctggactg ttcacggcag accagaacgt ttctggcctg ggttttgtgg tcatctattc    2220
tagcagggaa cactaaaggt ggaaataaaa gattttctat tatggaaata aagagttggc    2280
atgaaagtgg ctactgaaaa aaaaaaaaaa aaaaaaaaa a    2321
```

<210> SEQ ID NO 20
<211> LENGTH: 651
<212> TYPE: PRT
<213> ORGANISM: Homo sapiens

<400> SEQUENCE: 20

```
Met Ala Arg Gly Ser Ala Val Ala Trp Ala Ala Leu Gly Pro Leu Leu
1               5                   10                  15

Trp Gly Cys Ala Leu Gly Leu Gln Gly Gly Met Leu Tyr Pro Gln Glu
                20                  25                  30

Ser Pro Ser Arg Glu Cys Lys Glu Leu Asp Gly Leu Trp Ser Phe Arg
            35                  40                  45

Ala Asp Phe Ser Asp Asn Arg Arg Gly Phe Glu Glu Gln Trp Tyr
        50                  55                  60

Arg Arg Pro Leu Trp Glu Ser Gly Pro Thr Val Asp Met Pro Val Pro
65                  70                  75                  80

Ser Ser Phe Asn Asp Ile Ser Gln Asp Trp Arg Leu Arg His Phe Val
                85                  90                  95

Gly Trp Val Trp Tyr Glu Arg Glu Val Ile Leu Pro Glu Arg Trp Thr
            100                 105                 110

Gln Asp Leu Arg Thr Arg Val Val Leu Arg Ile Gly Ser Ala His Ser
        115                 120                 125

Tyr Ala Ile Val Trp Val Asn Gly Val Asp Thr Leu Glu His Glu Gly
    130                 135                 140

Gly Tyr Leu Pro Phe Glu Ala Asp Ile Ser Asn Leu Val Gln Val Gly
145                 150                 155                 160

Pro Leu Pro Ser Arg Leu Arg Ile Thr Ile Ala Ile Asn Asn Thr Leu
                165                 170                 175

Thr Pro Thr Thr Leu Pro Pro Gly Thr Ile Gln Tyr Leu Thr Asp Thr
            180                 185                 190

Ser Lys Tyr Pro Lys Gly Tyr Phe Val Gln Asn Thr Tyr Phe Asp Phe
        195                 200                 205

Phe Asn Tyr Ala Gly Leu Gln Arg Ser Val Leu Leu Tyr Thr Thr Pro
    210                 215                 220

Thr Thr Tyr Ile Asp Asp Ile Thr Val Thr Thr Ser Val Glu Gln Asp
225                 230                 235                 240
```

```
Ser Gly Leu Val Asn Tyr Gln Ile Ser Val Lys Gly Ser Asn Leu Phe
                245                 250                 255

Lys Leu Glu Val Arg Leu Leu Asp Ala Glu Asn Lys Val Val Ala Asn
            260                 265                 270

Gly Thr Gly Thr Gln Gly Gln Leu Lys Val Pro Gly Val Ser Leu Trp
        275                 280                 285

Trp Pro Tyr Leu Met His Glu Arg Pro Ala Tyr Leu Tyr Ser Leu Glu
    290                 295                 300

Val Gln Leu Thr Ala Gln Thr Ser Leu Gly Pro Val Ser Asp Phe Tyr
305                 310                 315                 320

Thr Leu Pro Val Gly Ile Arg Thr Val Ala Val Thr Lys Ser Gln Phe
                325                 330                 335

Leu Ile Asn Gly Lys Pro Phe Tyr Phe His Gly Val Asn Lys His Glu
            340                 345                 350

Asp Ala Asp Ile Arg Gly Lys Gly Phe Asp Trp Pro Leu Leu Val Lys
        355                 360                 365

Asp Phe Asn Leu Leu Arg Trp Leu Gly Ala Asn Ala Phe Arg Thr Ser
    370                 375                 380

His Tyr Pro Tyr Ala Glu Glu Val Met Gln Met Cys Asp Arg Tyr Gly
385                 390                 395                 400

Ile Val Val Ile Asp Glu Cys Pro Gly Val Gly Leu Ala Leu Pro Gln
                405                 410                 415

Phe Phe Asn Asn Val Ser Leu His His His Met Gln Val Met Glu Glu
            420                 425                 430

Val Val Arg Arg Asp Lys Asn His Pro Ala Val Val Met Trp Ser Val
        435                 440                 445

Ala Asn Glu Pro Ala Ser His Leu Glu Ser Ala Gly Tyr Tyr Leu Lys
    450                 455                 460

Met Val Ile Ala His Thr Lys Ser Leu Asp Pro Ser Arg Pro Val Thr
465                 470                 475                 480

Phe Val Ser Asn Ser Asn Tyr Ala Ala Asp Lys Gly Ala Pro Tyr Val
                485                 490                 495

Asp Val Ile Cys Leu Asn Ser Tyr Tyr Ser Trp Tyr His Asp Tyr Gly
            500                 505                 510

His Leu Glu Leu Ile Gln Leu Gln Leu Ala Thr Gln Phe Glu Asn Trp
        515                 520                 525

Tyr Lys Lys Tyr Gln Lys Pro Ile Ile Gln Ser Glu Tyr Gly Ala Glu
    530                 535                 540

Thr Ile Ala Gly Phe His Gln Asp Pro Pro Leu Met Phe Thr Glu Glu
545                 550                 555                 560

Tyr Gln Lys Ser Leu Leu Glu Gln Tyr His Leu Gly Leu Asp Gln Lys
                565                 570                 575

Arg Arg Lys Tyr Val Val Gly Glu Leu Ile Trp Asn Phe Ala Asp Phe
            580                 585                 590

Met Thr Glu Gln Ser Pro Thr Arg Val Leu Gly Asn Lys Lys Gly Ile
        595                 600                 605

Phe Thr Arg Gln Arg Gln Pro Lys Ser Ala Ala Phe Leu Leu Arg Glu
    610                 615                 620

Arg Tyr Trp Lys Ile Ala Asn Glu Thr Arg Tyr Pro His Ser Val Ala
625                 630                 635                 640

Lys Ser Gln Cys Leu Glu Asn Ser Leu Phe Thr
                645                 650
```

```
<210> SEQ ID NO 21
<211> LENGTH: 1435
<212> TYPE: DNA
<213> ORGANISM: Homo sapiens

<400> SEQUENCE: 21
ggcggggcct gcttctcctc agcttcaggc ggctgcgacg agccctcagg cgaacctctc      60
ggctttcccg cgcggcgccg cctcttgctg cgcctccgcc tcctcctctg ctccgccacc     120
ggcttcctcc tcctgagcag tcagcccgcg cgccggccgg ctccgttatg cgacccgca     180
gccctggcgt cgtgattagt gatgatgaac caggttatga ccttgattta ttttgcatac     240
ctaatcatta tgctgaggat ttggaaaggg tgtttattcc tcatggacta attatggaca     300
ggactgaacg tcttgctcga gatgtgatga aggagatggg aggccatcac attgtagccc     360
tctgtgtgct caaggggggc tataaattct ttgctgacct gctggattac atcaaagcac     420
tgaatagaaa tagtgataga tccattccta tgactgtaga ttttatcaga ctgaagagct     480
attgtaatga ccagtcaaca ggggacataa agtaattgg tggagatgat ctctcaactt     540
taactggaaa gaatgtcttg attgtggaag atataattga cactggcaaa acaatgcaga     600
ctttgctttc cttggtcagg cagtataatc caaagatggt caaggtcgca agcttgctgg     660
tgaaaaggac cccacgaagt gttggatata agccagactt tgttggattt gaaattccag     720
acaagtttgt tgtaggatat gcccttgact ataatgaata cttcagggat ttgaatcatg     780
tttgtgtcat tagtgaaact ggaaaagcaa aatacaaagc ctaagatgag agttcaagtt     840
gagtttggaa acatctggag tcctattgac atcgccagta aaattatcaa tgttctagtt     900
ctgtggccat ctgcttagta gagcttttg catgtatctt ctaagaattt tatctgtttt     960
gtactttaga aatgtcagtt gctgcattcc taaactgttt atttgcacta tgagcctata    1020
gactatcagt tcccttgggg cggattgttg tttaacttgt aaatgaaaaa attctcttaa    1080
accacagcac tattgagtga acattgaac tcatatctgt aagaaataaa gagaagatat    1140
attagttttt taattggtat tttaattttt atatatgcag gaaagaatag aagtgattga    1200
atattgttaa ttataccacc gtgtgttaga aaagtaagaa gcagtcaatt ttcacatcaa    1260
agacagcatc taagaagttt tgttctgtcc tggaattatt ttagtagtgt ttcagtaatg    1320
ttgactgtat tttccaactt gttcaaatta ttaccagtga atctttgtca gcagttccct    1380
tttaaatgca aatcaataaa ttcccaaaaa tttaaaaaaa aaaaaaaaaa aaaaa          1435

<210> SEQ ID NO 22
<211> LENGTH: 218
<212> TYPE: PRT
<213> ORGANISM: Homo sapiens

<400> SEQUENCE: 22

Met Ala Thr Arg Ser Pro Gly Val Val Ile Ser Asp Asp Glu Pro Gly
1               5                  10                  15

Tyr Asp Leu Asp Leu Phe Cys Ile Pro Asn His Tyr Ala Glu Asp Leu
            20                  25                  30

Glu Arg Val Phe Ile Pro His Gly Leu Ile Met Asp Arg Thr Glu Arg
        35                  40                  45

Leu Ala Arg Asp Val Met Lys Glu Met Gly Gly His His Ile Val Ala
    50                  55                  60

Leu Cys Val Leu Lys Gly Gly Tyr Lys Phe Phe Ala Asp Leu Leu Asp
65                  70                  75                  80

Tyr Ile Lys Ala Leu Asn Arg Asn Ser Asp Arg Ser Ile Pro Met Thr
```

```
                    85                  90                  95
Val Asp Phe Ile Arg Leu Lys Ser Tyr Cys Asn Asp Gln Ser Thr Gly
                100                 105                 110

Asp Ile Lys Val Ile Gly Gly Asp Asp Leu Ser Thr Leu Thr Gly Lys
            115                 120                 125

Asn Val Leu Ile Val Glu Asp Ile Ile Asp Thr Gly Lys Thr Met Gln
        130                 135                 140

Thr Leu Leu Ser Leu Val Arg Gln Tyr Asn Pro Lys Met Val Lys Val
145                 150                 155                 160

Ala Ser Leu Leu Val Lys Arg Thr Pro Arg Ser Val Gly Tyr Lys Pro
                165                 170                 175

Asp Phe Val Gly Phe Glu Ile Pro Asp Lys Phe Val Val Gly Tyr Ala
            180                 185                 190

Leu Asp Tyr Asn Glu Tyr Phe Arg Asp Leu Asn His Val Cys Val Ile
        195                 200                 205

Ser Glu Thr Gly Lys Ala Lys Tyr Lys Ala
    210                 215
```

<210> SEQ ID NO 23
<211> LENGTH: 2439
<212> TYPE: DNA
<213> ORGANISM: Homo sapiens

<400> SEQUENCE: 23

```
gagagcagcg gccgggaagg ggcggtgcgg gaggcggggt gtggggcggt agtgtgggcc      60
ctgttcctgc ccgcgcggtg ttccgcattc tgcaagcctc cggagcgcac gtcggcagtc     120
ggctccctcg ttgaccgaat caccgacctc tctccccagc tgtatttcca aaatgtcgct     180
ttctaacaag ctgacgctgg acaagctgga cgttaaaggg aagcgggtcg ttatgagagt     240
cgacttcaat gttcctatga agaacaacca gataacaaac aaccagagga ttaaggctgc     300
tgtcccaagc atcaaattct gcttggacaa tggagccaag tcggtagtcc ttatgagcca     360
cctaggccgg cctgatggtg tgcccatgcc tgacaagtac tccttagagc cagttgctgt     420
agaactcaaa tctctgctgg gcaaggatgt tctgttcttg aaggactgtg taggcccaga     480
agtggagaaa gcctgtgcca cccagctgc tgggtctgtc atcctgctgg agaacctccg     540
ctttcatgtg gaggaagaag ggaagggaaa agatgcttct gggaacaagg ttaaagccga     600
gccagccaaa atagaagctt tccgagcttc actttccaag ctaggggatg tctatgtcaa     660
tgatgctttt ggcactgctc acagagccca cagctccatg gtaggagtca atctgccaca     720
gaaggctggt gggttttttga tgaagaagga gctgaactac tttgcaaagg ccttggagag     780
cccagagcga cccttcctgg ccatcctggg cggagctaaa gttgcagaca gatccagct     840
catcaataat atgctggaca agtcaatga tgatgattatt ggtggtggaa tggcttttac     900
cttccttaag gtgctcaaca acatggagat tggcacttct ctgtttgatg aagagggagc     960
caagattgtc aaagacctaa tgtccaaagc tgagaagaat ggtgtgaaga ttaccttgcc    1020
tgttgacttt gtcactgctg acaagtttga tgagaatgcc aagactggcc aagccactgt    1080
ggcttctggc atacctgctg ctggatgggc ttggactgt ggtcctgaaa gcagcaagaa    1140
gtatgctgag gctgtcactc gggctaagca gattgtgtgg aatggtcctg tgggggtatt    1200
tgaatgggaa gcttttgccc ggggaaccaa agctctcatg gatgaggtgg tgaaagccac    1260
ttctaggggc tgcatcacca tcataggtgg tggagacact gccacttgct gtgccaaatg    1320
gaacacggag gataaagtca gccatgtgag cactggggt ggtgccagtt tggagctcct    1380
```

```
ggaaggtaaa gtccttcctg gggtggatgc tctcagcaat atttagtact tcctgcctt    1440 ttagttcctg tgcacagccc ctaagtcaac ttagcatttt ctgcatctcc acttggcatt    1500
agctaaaacc ttccatgtca agattcagct agtggccaag agatgcagtg ccaggaaccc    1560
ttaaacagtt gcacagcatc tcagctcatc ttcactgcac cctggatttg catacattct    1620
tcaagatccc atttgaattt tttagtgact aaaccattgt gcattctaga gtgcatatat    1680
ttatattttg cctgttaaaa agaaagtgag cagtgttagc ttagttctct tttgatgtag    1740
gttattatga ttagctttgt cactgtttca ctactcagca tggaaacaag atgaaattcc    1800
atttgtaggt agtgagacaa aattgatgat ccattaagta aacaataaaa gtgtccattg    1860
aaaccgtgat ttttttttt tcctgtcat actttgttag aagggtgag aatagaatct    1920 tgaggaacgg atcagatgtc tatattgctg aatgcaagaa gtggggcagc agcagtggag    1980
agatgggaca attagataaa tgtccattct ttatcaaggg cctactttat ggcagacatt    2040
gtgctagtgc ttttattcta acttttattt ttatcagtta cacatgatca taatttaaaa    2100
agtcaaggct tataacaaaa aagccccagc ccattcctcc cattcaagat tcccactccc    2160
cagaggtgac cactttcaac tcttgagttt ttcaggtata tacctccatg tttctaagta    2220
atatgcttat attgttcact tctttttttt ttatttttta aagaaatcta tttcatacca    2280
tggaggaagg ctctgttcca catatatttc cacttcttca ttctctcggt atagttttgt    2340
cacaattata gattagatca aaagtctaca taactaatac agctgagcta tgtagtatgc    2400
tatgattaaa tttacttatg taaaaaaaaa aaaaaaaa                           2439

<210> SEQ ID NO 24
<211> LENGTH: 417
<212> TYPE: PRT
<213> ORGANISM: Homo sapiens

<400> SEQUENCE: 24

Met Ser Leu Ser Asn Lys Leu Thr Leu Asp Lys Leu Asp Val Lys Gly
1               5                   10                  15

Lys Arg Val Val Met Arg Val Asp Phe Asn Val Pro Met Lys Asn Asn
            20                  25                  30

Gln Ile Thr Asn Asn Gln Arg Ile Lys Ala Ala Val Pro Ser Ile Lys
        35                  40                  45

Phe Cys Leu Asp Asn Gly Ala Lys Ser Val Val Leu Met Ser His Leu
    50                  55                  60

Gly Arg Pro Asp Gly Val Pro Met Pro Asp Lys Tyr Ser Leu Glu Pro
65                  70                  75                  80

Val Ala Val Glu Leu Lys Ser Leu Leu Gly Lys Asp Val Leu Phe Leu
                85                  90                  95

Lys Asp Cys Val Gly Pro Glu Val Glu Lys Ala Cys Ala Asn Pro Ala
            100                 105                 110

Ala Gly Ser Val Ile Leu Leu Glu Asn Leu Arg Phe His Val Glu Glu
        115                 120                 125

Glu Gly Lys Gly Lys Asp Ala Ser Gly Asn Lys Val Lys Ala Glu Pro
    130                 135                 140

Ala Lys Ile Glu Ala Phe Arg Ala Ser Leu Ser Lys Leu Gly Asp Val
145                 150                 155                 160

Tyr Val Asn Asp Ala Phe Gly Thr Ala His Arg Ala His Ser Ser Met
                165                 170                 175

Val Gly Val Asn Leu Pro Gln Lys Ala Gly Gly Phe Leu Met Lys Lys
```

```
                       180                 185                 190
Glu Leu Asn Tyr Phe Ala Lys Ala Leu Glu Ser Pro Glu Arg Pro Phe
                195                 200                 205

Leu Ala Ile Leu Gly Gly Ala Lys Val Ala Asp Lys Ile Gln Leu Ile
            210                 215                 220

Asn Asn Met Leu Asp Lys Val Asn Glu Met Ile Gly Gly Gly Met
225                 230                 235                 240

Ala Phe Thr Phe Leu Lys Val Leu Asn Asn Met Glu Ile Gly Thr Ser
                245                 250                 255

Leu Phe Asp Glu Glu Gly Ala Lys Ile Val Lys Asp Leu Met Ser Lys
            260                 265                 270

Ala Glu Lys Asn Gly Val Lys Ile Thr Leu Pro Val Asp Phe Val Thr
        275                 280                 285

Ala Asp Lys Phe Asp Glu Asn Ala Lys Thr Gly Gln Ala Thr Val Ala
        290                 295                 300

Ser Gly Ile Pro Ala Gly Trp Met Gly Leu Asp Cys Gly Pro Glu Ser
305                 310                 315                 320

Ser Lys Lys Tyr Ala Glu Ala Val Thr Arg Ala Lys Gln Ile Val Trp
                325                 330                 335

Asn Gly Pro Val Gly Val Phe Glu Trp Glu Ala Phe Ala Arg Gly Thr
            340                 345                 350

Lys Ala Leu Met Asp Glu Val Val Lys Ala Thr Ser Arg Gly Cys Ile
        355                 360                 365

Thr Ile Ile Gly Gly Gly Asp Thr Ala Thr Cys Cys Ala Lys Trp Asn
        370                 375                 380

Thr Glu Asp Lys Val Ser His Val Ser Thr Gly Gly Gly Ala Ser Leu
385                 390                 395                 400

Glu Leu Leu Glu Gly Lys Val Leu Pro Gly Val Asp Ala Leu Ser Asn
                405                 410                 415

Ile

<210> SEQ ID NO 25
<211> LENGTH: 748
<212> TYPE: DNA
<213> ORGANISM: Homo sapiens

<400> SEQUENCE: 25
gcagataatg ggaggagccg ggcccgagcg agctctttcc tttcgctgct gcggccgcag      60
ccatgagtat gctcaggctt cagaagaggc tcgcctctag tgtcctccgc tgtggcaaga     120
agaaggtctg gttagacccc aatgagacca atgaaatcgc caatgccaac tcccgtcagc     180
agatccggaa gctcatcaaa gatgggctga tcatccgcaa gcctgtgacg gtccattccc     240
gggctcgatg ccggaaaaac accttggccc gccggaaggg caggcacatg gcataggta      300 agcggaaggg tacagccaat gcccgaatgc cagagaaggt cacatggatg aggagaatga     360
ggattttgcg ccggctgctc agaagatacc gtgaatctaa gaagatcgat cgccacatgt     420
atcacagcct gtacctgaag gtgaagggga atgtgttcaa aaacaagcgg attctcatgg     480
aacacatcca caagctgaag gcagacaagg cccgcaagaa gctcctggct gaccaggctg     540
aggcccgcag gtctaagacc aaggaagcac gcaagcgccg tgaagagcgc ctccaggcca     600
agaaggagga gatcatcaag actttatcca aggaggaaga gaccaagaaa taaaacctcc     660
cactttgtct gtacatactg gcctctgtga ttacatagat cagccattaa aataaaacaa     720
gccttaatct gcaaaaaaaa aaaaaaaa                                         748
```

<210> SEQ ID NO 26
<211> LENGTH: 196
<212> TYPE: PRT
<213> ORGANISM: Homo sapiens

<400> SEQUENCE: 26

Met Ser Met Leu Arg Leu Gln Lys Arg Leu Ala Ser Ser Val Leu Arg
1               5                   10                  15

Cys Gly Lys Lys Lys Val Trp Leu Asp Pro Asn Glu Thr Asn Glu Ile
            20                  25                  30

Ala Asn Ala Asn Ser Arg Gln Gln Ile Arg Lys Leu Ile Lys Asp Gly
        35                  40                  45

Leu Ile Ile Arg Lys Pro Val Thr Val His Ser Arg Ala Arg Cys Arg
    50                  55                  60

Lys Asn Thr Leu Ala Arg Arg Lys Gly Arg His Met Gly Ile Gly Lys
65                  70                  75                  80

Arg Lys Gly Thr Ala Asn Ala Arg Met Pro Glu Lys Val Thr Trp Met
                85                  90                  95

Arg Arg Met Arg Ile Leu Arg Arg Leu Leu Arg Arg Tyr Arg Glu Ser
            100                 105                 110

Lys Lys Ile Asp Arg His Met Tyr His Ser Leu Tyr Leu Lys Val Lys
        115                 120                 125

Gly Asn Val Phe Lys Asn Lys Arg Ile Leu Met Glu His Ile His Lys
    130                 135                 140

Leu Lys Ala Asp Lys Ala Arg Lys Lys Leu Leu Ala Asp Gln Ala Glu
145                 150                 155                 160

Ala Arg Arg Ser Lys Thr Lys Glu Ala Arg Lys Arg Arg Glu Glu Arg
                165                 170                 175

Leu Gln Ala Lys Lys Glu Glu Ile Ile Lys Thr Leu Ser Lys Glu Glu
            180                 185                 190

Glu Thr Lys Lys
        195

<210> SEQ ID NO 27
<211> LENGTH: 2772
<212> TYPE: DNA
<213> ORGANISM: Homo sapiens

<400> SEQUENCE: 27
agtcttttgt cggcggctcg acctgcgcgt gcgccgcagt cacgtggagg gcgggggggg      60
tggtcgactg cggcggcagc tctttcctca gaccccagc cttttgtgcg ccgcgcggtg     120
gggcggtgcc cagcttgggg gaaggagagc ggcgcttatc gaagtgtggt cgacctccat     180
ccgcccaccg agcacttggg acccgctgca catatccaga gcagggaaag ctgtggcttt     240 ctcggggggag cgagtgtcta ggggaagggt gtggcaggcc cacggatgc catgccctag     300 aacaacggcc tgagcgcttg tggaattaaa atgggagatg tggggccgag gtgggcgaat     360
tgggatccct ccaggtcagg ggttcgagac catcctgggc aacaaagcga gaccctcccc     420
catgccacgt ttctacaaaa aataaaattc tgggaggtga tcagtgatga acatggcatc     480
gaccccaccg gcacctacca cggggacagc gacctgcagc tggaccgcat ctctgtgtac     540
tacaatgaag ccacaggtgg caaatatgtt cctcgtgcca tcctggtgga tctagaacct     600
gggaccatgg actctgttcg ctcaggtcct tttggccaga tctttagacc agacaacttt     660
gtatttggtc agtctggggc aggtaacaac tgggccaaag gccactacac agagggcgcc     720

```
gagctggttg attctgtcct ggatgtggta cggaaggagg cagagagctg tgactgcctg    780
cagggcttcc agctgaccca ctcactgggc gggggcacag gctctggaat gggcactctc    840
cttatcagca agatccgaga agaatacccct gatcgcatca tgaataccctt cagtgtggtg   900 ccttcaccca aagtgtctga caccgtggtc gagccctaca atgccaccct ctccgtccat   960
cagttggtag agaatactga tgagacctat tgcattgaca acgaggccct ctatgatatc  1020
tgcttccgca ctctgaagct gaccacacca acctacgggg atctgaacca ccttgtctca  1080
gccaccatga gtggtgtcac cacctgcctc cgtttccctg gccagctcaa tgctgacctc  1140
cgcaagttgg cagtcaacat ggtccccttc ccacgtctcc atttctttat gcctggcttt  1200
gcccctctca ccagccgtgg aagccagcag tatcgagctc tcacagtgcc ggaactcacc  1260
cagcaggtct tcgatgccaa gaacatgatg gctgcctgtg accccgcca cggccgatac   1320 ctcaccgtgg ctgctgtctt ccgtggtcgg atgtccatga aggaggtcga tgagcagatg  1380
cttaacgtgc agaacaagaa cagcagctac tttgtggaat ggatccccaa caatgtcaag  1440
acagccgtct gtgacatccc acctcgtggc ctcaagatgg cagtcacctt cattggcaat  1500
agcacagcca tccaggagct cttcaagcgc atctcggagc agttcactgc catgttccgc  1560
cggaaggcct tcctccactg gtacacaggc gagggcatgg acgagatgga gttcaccgag  1620
gctgagagca acatgaacga cctcgtctct gagtatcagc agtaccagga tgccaccgca  1680
gaagaggagg aggatttcgg tgaggaggcc gaagaggagg cctaaggcag agcccccatc  1740
acctcaggct tctcagttcc cttagccgtc ttactcaact gcccctttcc tctccctcag  1800
aatttgtgtt tgctgcctct atcttgtttt ttgttttttc ttctgggggg ggtctagaac  1860
agtgcctggc acatagtagg cgctcaataa atacttgttt gttgaatgtc tcctctctct  1920
ttccactctg ggaaacctag gtttctgcca ttctgggtga ccctgtattt ctttctggtg  1980
cccattccat ttgtccagtt aatacttcct cttaaaaatc tccaagaagc tgggtctcca  2040
gatcccattt agaaccaacc aggtgctgaa acacatgta gataatggcc atcatcctaa    2100
gcccaaagta gaaaatggta gaaggtagtg ggtagaagtc actatataag gaaggggatg  2160
ggattttcca ttctaaaagt tttggagagg gaaatccagg ctattaaagt cactaaatttt  2220 ctaagtatgt ccatttccca tctcagcttc aagggaggtg tcagcagtat tatctccact  2280
ttcaatctcc ctccaagctc tactctggag gagtctgtcc cactctgtca agtggaatcc  2340 ttcccttttcc aactctacct cccctcactca gctcctttcc cctgatcaga gaaagggatc  2400
aagggggttg ggagggggga aagagaccag ccttggtccc taagcctcca gaaacgtctt  2460
cttaatcccc accttttctt actcccaaaa aagaatgaac acccctgact ctggagtggt  2520
gtatactgcc acatcagtgt ttgagtcagt ccccagagga gagggaaacc ctcctccatc  2580 tttttttgcaa catctcattt cttccttttg ctgttgcttc ccccctcaca cacttggttt  2640
tgttctatcc tacatttgag atttctattt tatgttgaac ttgctgcttt ttttcatatt  2700
gaaaagatga catcgcccca agagccaaaa ataaatggga attgaaaaaa gctgaaaaaa  2760
aaaaaaaaaa aa                                                       2772
```

<210> SEQ ID NO 28
<211> LENGTH: 444
<212> TYPE: PRT
<213> ORGANISM: Homo sapiens

<400> SEQUENCE: 28

```
Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Asp Arg Ile Ser
                35                  40                  45

Val Tyr Tyr Asn Glu Ala Thr Gly Gly Lys Tyr Val Pro Arg Ala Ile
    50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
                100                 105                 110

Val Asp Ser Val Leu Asp Val Val Arg Lys Glu Ala Glu Ser Cys Asp
            115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
    195                 200                 205

Asp Ile Cys Phe Arg Thr Leu Lys Leu Thr Thr Pro Thr Tyr Gly Asp
210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
    275                 280                 285

Leu Thr Gln Gln Val Phe Asp Ala Lys Asn Met Met Ala Ala Cys Asp
290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ala Val Thr Phe Ile
    355                 360                 365

Gly Asn Ser Thr Ala Ile Gln Glu Leu Phe Lys Arg Ile Ser Glu Gln
370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
```

```
            420           425           430
Glu Glu Asp Phe Gly Glu Glu Ala Glu Glu Glu Ala
        435                 440
```

<210> SEQ ID NO 29
<211> LENGTH: 1864
<212> TYPE: DNA
<213> ORGANISM: Homo sapiens

<400> SEQUENCE: 29

```
tgtgcgtcgc tccccaatgg aaaaggagag ctgccttcac aggaccagga attggtttat    60
ctacgcgaat aatagcatga cccgggcggg gatagcctat cacgtgctgc tagacggaac   120
ggggcgggc aggccactgg ttgcggagtg agctgggcgc gcggcgcgca ggcgccctgg   180
ggacccggta gcggcggtgg cggtggcggc ggtggcggtg gctgcggcga cggcagaggc   240
gaagggagcc ggatcgccga cctgagcggg aggcggcggt ggcggccatg gcggcagatg   300
gagagcgttc cccgctgctg tctgagccca tcgacggtgg cgcgggcggc aacggtttag   360
tggggcccgg cgggagtggg gctgggcccg ggggaggcct gaccccctcc gcaccaccgt   420
acggagccgg taaacatgcc ccgccccagg catttccccc gtttcccgag ggcatccag   480
ccgtgttgcc tggggaggac ccacccccct attcacccctt aactagcccg gacagtggga   540
gtgcccctat gatcacctgc cgagtctgcc aatctctcat caacgtggaa ggcaagatgc   600
atcagcatgt agtcaaatgt ggtgtctgca atgaagccac cccaatcaag aatgcacccc   660
cagggaaaaa atatgttcga tgcccctgta actgtctcct tatctgcaaa gtgacatccc   720
aacggattgc atgccctcgg ccctactgca aaagaatcat caacctgggg cctgtgcatc   780
ccggacctct gagtccagaa ccccaaccca tgggtgtcag ggttatctgt ggacattgca   840
agaatacttt tctgtggaca gagttcacag accgcacttt ggcacgttgt cctcactgca   900
ggaaagtgtc atctattggg cgcagatacc cacgtaagag atgtatctgc tgcttcttgc   960
ttggcttgct tttggcagtc actgccactg gccttgcctt tggcacatgg aagcatgcac   1020
ggcgatatgg aggcatctat gcagcctggg catttgtcat cctgttggct gtgctgtgtt   1080
tgggccgggc tctttattgg gcctgtatga aggtcagcca ccctgtccag aacttctcct   1140
gagcctgatg acccacagac tgtgcctggc ccctccctgg tggggacagt gacactacga   1200
agggagctgg ggtagttaaa ggctcccggg gcttctagaa ggaagccaag cagctgcctt   1260
cctttccct ggggagaggt aggaaggaac caggccctca cttaggtttg gaggggcaga   1320
taagagcact gctgaccatc tgctttcctc caagggttgc tgtgtctagg gtgaagtagg   1380
caaaacgttg cccttaaaac tgggccctga agacggttcc agccttgtcc ttcctgtgtg   1440
ctccctgaga gccattcctg tcccttacac attccagggc agggtggggg tgggtagccc   1500
tgggggttcc cctccctctt gtgcaccatt aggactttgc tgctgctatt gcacttcacc   1560
agaggttggc tctggcctca gtaccctcag tctcctctcc ccacattgtg tcctgtgggg   1620
gtggggtcag ccgctgctct gtacagaacc acaggaactg atgtgtatat aactatttaa   1680
tgtgggatat gttcccctat tcctgtattt ccctaattc ctcctcccga cctttttac   1740
ccccccagtt gcagtattta actgggctgg gtagggttgc tcagtctttg ggggaggtta   1800
gggacttatc ctgtgcttgt aaataaataa ggtcatgact ctacgcttaa aaaaaaaaa   1860
aaaa                                                                1864
```

<210> SEQ ID NO 30

```
<211> LENGTH: 277
<212> TYPE: PRT
<213> ORGANISM: Homo sapiens

<400> SEQUENCE: 30

Met Ala Ala Asp Gly Glu Arg Ser Pro Leu Leu Ser Glu Pro Ile Asp
1               5                   10                  15

Gly Gly Ala Gly Gly Asn Gly Leu Val Gly Pro Gly Gly Ser Gly Ala
            20                  25                  30

Gly Pro Gly Gly Gly Leu Thr Pro Ser Ala Pro Pro Tyr Gly Ala Ala
            35                  40                  45

Phe Pro Pro Phe Pro Glu Gly His Pro Ala Val Leu Pro Gly Glu Asp
    50                  55                  60

Pro Pro Pro Tyr Ser Pro Leu Thr Ser Pro Asp Ser Gly Ser Ala Pro
65                  70                  75                  80

Met Ile Thr Cys Arg Val Cys Gln Ser Leu Ile Asn Val Glu Gly Lys
                85                  90                  95

Met His Gln His Val Val Lys Cys Gly Val Cys Asn Glu Ala Thr Pro
            100                 105                 110

Ile Lys Asn Ala Pro Pro Gly Lys Lys Tyr Val Arg Cys Pro Cys Asn
        115                 120                 125

Cys Leu Leu Ile Cys Lys Val Thr Ser Gln Arg Ile Ala Cys Pro Arg
    130                 135                 140

Pro Tyr Cys Lys Arg Ile Ile Asn Leu Gly Pro Val His Pro Gly Pro
145                 150                 155                 160

Leu Ser Pro Glu Pro Gln Pro Met Gly Val Arg Val Ile Cys Gly His
                165                 170                 175

Cys Lys Asn Thr Phe Leu Trp Thr Glu Phe Thr Asp Arg Thr Leu Ala
            180                 185                 190

Arg Cys Pro His Cys Arg Lys Val Ser Ser Ile Gly Arg Arg Tyr Pro
        195                 200                 205

Arg Lys Arg Cys Ile Cys Cys Phe Leu Leu Gly Leu Leu Leu Ala Val
    210                 215                 220

Thr Ala Thr Gly Leu Ala Phe Gly Thr Trp Lys His Ala Arg Arg Tyr
225                 230                 235                 240

Gly Gly Ile Tyr Ala Ala Trp Ala Phe Val Ile Leu Leu Ala Val Leu
                245                 250                 255

Cys Leu Gly Arg Ala Leu Tyr Trp Ala Cys Met Lys Val Ser His Pro
            260                 265                 270

Val Gln Asn Phe Ser
            275
```